United States Patent
Peretz et al.

(10) Patent No.: US 9,301,998 B2
(45) Date of Patent: Apr. 5, 2016

(54) ALLOGENEIC TUMOR CELL VACCINATION

(71) Applicant: HADASIT MEDICAL RESEARCH SERVICES AND DEVELOPMENT LTD.., Jerusalem (IL)

(72) Inventors: Tamar Peretz, Jerusalem (IL); Michal Lotem, Reut (IL); Arthur Machlenkin, Mazkeret Batya (IL); Shoshana Frankenburg, Jerusalem (IL); Inna Ben David, Jerusalem (IL); Anna Kuznetz, Jerusalem (IL); Yael Gelfand, Givat Ze'ev (IL); Galit Eisenberg, Modiin (IL); Merav Darash Yahana, Jerusalem (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 138 days.

(21) Appl. No.: 14/081,761

(22) Filed: Nov. 15, 2013

(65) Prior Publication Data

US 2014/0141045 A1 May 22, 2014

Related U.S. Application Data

(63) Continuation of application No. PCT/IL2012/000197, filed on May 17, 2012.

(60) Provisional application No. 61/501,797, filed on Jun. 28, 2011, provisional application No. 61/487,218, filed on May 17, 2011.

(51) Int. Cl.
| | |
|---|---|
| *A61K 39/00* | (2006.01) |
| *C12N 5/09* | (2010.01) |
| *C12Q 1/68* | (2006.01) |
| *G01N 33/574* | (2006.01) |

(52) U.S. Cl.
CPC .......... *A61K 39/0011* (2013.01); *C12N 5/0693* (2013.01); *C12Q 1/6886* (2013.01); *G01N 33/57492* (2013.01); *A61K 2039/5152* (2013.01)

(58) Field of Classification Search
None
See application file for complete search history.

(56) References Cited

U.S. PATENT DOCUMENTS

| 5,882,654 A | 3/1999 | Morton |
| 2010/0055136 A1 | 3/2010 | Stathopoulos |
| 2010/0119537 A1 | 5/2010 | Podack |

FOREIGN PATENT DOCUMENTS

| EP | 2404614 A1 | 1/2012 |
| WO | 9003183 A1 | 4/1990 |
| WO | 02053176 A2 | 7/2002 |

OTHER PUBLICATIONS

Escudier et al (Journal of Translational Medicine, 2005, vol. 3, pp. 1-13.*
Cortes et al, Leukemia, 1998, vol. 12, pp. 455-462.*
Abstract of Zhang et al, Shanghai Dier Yike Daxue Xuebao, 1996, vol. 16, pp. 397-399.*
Abstract of Arshdeep et al, Pharmaceutical Biology, 2012, vol. 50, pp. 1473-1591.*
Abstract of Fontan, Allergologia et Immunopathologia, 2001, vol. 29, pp. 101-107.*
Abstract of Magil et al, Kidney International, 1988, vol. 34, pp. 511-517.*
Abstract of Katori et al, Inflammation Research, 2000, vol. 49, pp. 367-392.*
Abstract of Ichikawa, American Journal of Hematology, 1999, vol. 66, pp. 305-308.*
Abstract of Claffey et al, Cancer Metastasis Reviews, 1996, vol. 15, pp. 165-176.*
Abstract of Harris et al, Clinical Orthopaedics and Related Research, 1975, vol. 110, pp. 303-316.*
Wheeler (Salud p'ublica de M'exico, 1997, vol. 39, pp. 283-237).*
Efferson et al (Anticancer Research, 2005, vol. 25, pp. 715-724).*
Bachman et al (Journal of Immunology, 2005, vol. 175, pp. 4677-4685).*
Michael et al (Clinical Cancer Research, 2005, vol. 11, pp. 4469-4478).*
Correale (JNCI, 1997, vol. 89, pp. 293-300).*
McCoy et al (Biotechnology Progress, 2009, vol. 25, pp. 1448-1458).*
Serotec mAb clone 60442007; Edition Nov. 8, 2011, Retrieved from: http://www.funakoshi.co.jp/data/datasheet/ABD/6044-2007.pdf.
Barth et al., (1994) Polyvalent melanoma cell vaccine induces delayed-type hypersensitivity and in vitro cellular immune response. Cancer Res 54(13): 3342-3345.
Bioley et al., (2009) HLA class I—associated immunodominance affects CTL responsiveness to an ESO recombinant protein tumor antigen vaccine. Clin Cancer Res 15(1): 299-306.
Brossart et al., (1999) Identification of HLA-A2-restricted T-cell epitopes derived from the MUC1 tumor antigen for broadly applicable vaccine therapies. Blood 93(12): 4309-4317.
Bystryn et al., (1992) Relationship between immune response to melanoma vaccine immunization and clinical outcome in stage II malignant melanoma. Cancer 69(5): 1157-1164.
Chapman (2007) Melanoma vaccines. Semin oncol 34(6): 516-523.
Cheuk et al., (2004) Role of 4-1BB:4-1BB ligand in cancer immunotherapy. Cancer Gene Therapy 11(3): 215-226.
Duffy (1999) CA 15-3 and Related Mucins as Circulating Markers in Breast Cancer. Ann Clin Biochem 36(5): 579-586.
Duk et al., (1989) Tumor markers CA 125, squamous cell carcinoma antigen, and carcinoembryonic antigen in patients with adenocarcinoma of the uterine cervix. Obstet Gynecol 73(4): 661-668.

(Continued)

*Primary Examiner* — Karen Canella
(74) *Attorney, Agent, or Firm* — Vorys, Sater, Seymour & Pease LLP

(57) ABSTRACT

The present invention relates to cancer immunotherapy, specifically to allogeneic tumor cell vaccines. According to some embodiments, the invention provides novel cell lines useful as therapeutic cell vaccine compositions. The invention further provides advantageous screening methods and means for identifying patients amenable for treatment with partially Human Leukocyte Antigen (HLA) matched allogeneic cell vaccines. Therapeutic compositions and methods for use in proliferative disorders are further provided.

24 Claims, 14 Drawing Sheets

(56) References Cited

OTHER PUBLICATIONS

Eggermont et al., (2008) Adjuvant therapy with pegylated interferon alfa-2b versus observation alone in resected stage Iii melanoma: final results of EORTC 18991, a randomised phase III trial. Lancet 372(9633): 117-126.

Hiratsuka et al., (2006) Competitive allele-specific short oligonucleotide hybridization (CASSOH) with enzyme-linked immunosorbent assay (ELISA) for the detection of pharmacogenetic single nucleotide polymorphisms (SNPs). J Biochem Biophys Methods 67(2-3): 87-94.

Hoon et al., (1998) Is the survival of melanoma patients receiving polyvalent melanoma cell vaccine linked to the human leukocyte antigen phenotype of patients? J Clin Oncol 16(4): 1430-1437.

Kirkwood et al., (2001) High-dose interferon alfa-2b significantly prolongs relapse-free and overall survival compared with the GM2-KLH/QS-21 vaccine in patients with resected stage IIB-III melanoma: results of intergroup trial E1694/S9512/C509801. J Clin Oncol 19(9): 2370-2380.

Kvistborg et al., (2008) Characterization of a single peptide derived from cytochrome P450 1B1 that elicits spontaneous human leukocyte antigen (HLA)-A1 as well as HLA-B35 restricted CD8 T-cell responses in cancer patients. Hum Immunol 69(4-5): 266-272.

Liang et al., (2004) High efficiency gene transfer into mammalian kidney cells using baculovirus vectors. Arch Virol 149 (1): 51-60.

Lotem et al., (2002) Autologous cell vaccine as a post operative adjuvant treatment for high-risk melanoma patients (AJCC stages III and IV). The new American Joint Committee on Cancer. Br J Cancer 86(10): 1534-1539.

Lotem et al., (2009) Autologous melanoma vaccine induces antitumor and self-reactive immune responses that affect patient survival and depend on MHC class II expression on vaccine cells. Clin Cancer Res 15(15): 4968-4977.

Lotem et al., (2011) HLA-B35 correlates with a favorable outcome following adjuvant administration of an HLA-matched allogeneic melanoma vaccine. Tissue Antigens 78(3): 203-207.

Machlenkin et al., (2005) Combined dendritic cell cryotherapy of tumor induces systemic antimetastatic immunity. Clin Cancer Res 11(13): 4955-4961.

Marsh et al., (2005) Nomenclature for factors of the HLA system, 2004. Tissue Antigens 65(4): 301-369.

Miller and Claman (1976) The induction of hapten-specific T cell tolerance by using hapten-modified lymphoid cells. I. Characteristics of tolerance induction. J Immunol 117(5 Pt 1): 1519-1526.

Mitchell et al., (2007) Randomized trial of an allogeneic melanoma lysate vaccine with low-dose interferon Alfa-2b compared with high-dose interferon Alfa-2b for Resected stage III cutaneous melanoma. J Clin Oncol 25(15): 2078-2085.

Morel et al., (1999) A tyrosinase peptide presented by HLA-B35 is recognized on a human melanoma by autologous cytotoxic T lymphocytes. Int J Cancer 83(6): 755-759.

Morelli (2006) The immune regulatory effect of apoptotic cells and exosomes on dendritic cells: its impact on transplantation. Am J Transplant 6(2): 254-261.

Morton et al., (1992) Prolongation of survival in metastatic melanoma after active specific immunotherapy with a new polyvalent melanoma vaccine. Ann Surg 216(4): 463-482; Erratum in: Ann Surg Mar. 1993;217(3):309.

Morton et al., (2002) Prolonged survival of patients receiving active immunotherapy with Canvaxin therapeutic polyvalent vaccine after complete resection of melanoma metastatic to regional lymph nodes. Ann Surg 236(4): 438-448; discussion 448-449.

Nasi et al., (1997) Anti-melanoma effects of R24, a monoclonal antibody against GD3 ganglioside. Melanoma Res 7 (Suppl 2): 3155-3162.

Orchard (2000) Comparison of immunohistochemical labelling of melanocyte differentiation antibodies melan-A, tyrosinase and HMB 45 with NKIC3 and S100 protein in the evaluation of benign naevi and malignant melanoma. Histochem J 32(8): 475-481.

Pectasides et al., (2009) Randomized phase ILL study of 1 month versus 1 year of adjuvant high-dose interferon alfa-2b in patients with resected high-risk melanoma. J Clin Oncol 27(6): 939-944.

Rapanotti et al., (2009) Melanoma-associated markers expression in blood: MUC-18 is associated with advanced stages in melanoma patients. Br J Dermatol 160(2): 338-344.

Re et al., (2006) Killer cell Ig-like receptors ligand-mismatched, alloreactive natural killer cells lyse primary solid tumors. Cancer 107(3): 640-648.

Reker et al., (2004) HLA-B35-restricted immune responses against survivin in cancer patients. Int J Cancer 108(6): 937-941.

Riker et al., (2007) Immunotherapy of melanoma: a critical review of current concepts and future strategies. Expert Opin Biol Ther 7(3): 345-358.

Schultz et al., (2001) A MAGE-3 peptide recognized on HLA-B35 and 1-ILA-A1 by cytolytic T lymphocytes. Tissue Antigens 57(2): 103-109.

Sharpe (2009) Mechanisms of costimulation. Immunol Rev 229(1): 5.11.

Sugita et al., (1996) Melanocyte lysis by cytotoxic T lymphocytes recognizing the MART-1 melanoma antigen in HLA-A2 patients with Vogt-Koyanagi-Harada disease. Int Immunol 8(5): 799-803.

Touloukian et al., (2003) Normal tissue depresses while tumor tissue enhances human T cell responses in vivo to a novel self/tumor melanoma antigen, OA1. J Immunol 170(3): 1579-1585.

Vigneron et al., (2005) A peptide derived from melanocytic protein gp100 and presented by HLA-B35 is recognized by autologous cytolytic T lymphocytes on melanoma cells. Tissue Antigens 65(2): 156-162.

Wen et al., (2002) 4-1BB ligand-mediated costimulation of human T cells induces CD4 and CD8 T cell expansion, cytokine production, and the development of cytolytic effector function. J Immunol 168(10): 4897-4906.

Ca-125-sec Acc. No. Q8WXI7; Retrieved on May 3, 2011 from: http://www.uniprot.org/uniprot/Q8WXI7.

CD146 Acc. No. P43121; Retrieved on Apr. 5, 2011 from: http://www.uniprot.org/uniprot/P43121.

CEA Acc. No. P06731; Retrieved on May 3, 2011 from: http://www.uniprot.org/uniprot/P06731.

Dako anti-S100 antibody Cat. No. N1573; Edition Aug. 13, 2003, Retrieved from: http://www.dako.com/dist/download.pdf?objectid=104721004.

HMB45 Acc. No. P40967; Retrieved on Apr. 5, 2011 from: http://www.uniprot.org/uniprot/P40967.

HMW Acc. No. NM_001897; Dated Dec. 1, 2013 Retrieved from: http://www.ncbi.nlm.nih.gov/nuccore/NM_001897.4.

Invitrogen anti-cytokeratin mAb Clone: AE1/AE3 (Cat. No. 08-4132); Edition 2008, Retrieved from: http://tools.lifetechnologies.com/content/sfs/manuals/084132_Rev0808.pdf.

MAGE-A1 Acc. No. P43355; Retrieved on Apr. 5, 2011 from: http://www.uniprot.org/uniprot/P43355.

MAGE-A3 Acc. No. P43357; Retrieved on Apr. 5, 2011 from: http://www.uniprot.org/uniprot/P43357.

Melan A/MART-I Uniprot: Q16655; Retrieved on Apr. 5, 2011 from: http://www.uniprot.org/uniprot/Q16655.

MUC-1 Acc. No. P15941; Retrieved on May 3, 2011 from: http://www.uniprot.org/uniprot/P15941.

NY-ESO-1 Acc. No. P78358; Retrieved on Apr. 5, 2011 from: http://www.uniprot.org/uniprot/P78358.

\* cited by examiner

R-24 (anti GD3)    Anti Melan A/Mart I

HMB45 (anti gp100)    S100

SEQUENCE LISTING

<160> NUMBER OF SEQ ID NOS: 15

<210> SEQ ID NO 1
<211> LENGTH: 362
<212> TYPE: PRT
<213> ORGANISM: Homo sapiens

<400> SEQUENCE: 1

```
Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Pro Arg Thr Glu Pro Arg Ala Pro Trp Ile Glu Gln Glu Gly
65                  70                  75                  80

Pro Glu Tyr Trp Asp Arg Asn Thr Gln Ile Phe Lys Thr Asn Thr Gln
                85                  90                  95

Thr Tyr Arg Glu Ser Leu Arg Asn Leu Arg Gly Tyr Tyr Asn Gln Ser
            100                 105                 110

Glu Ala Gly Ser His Ile Ile Gln Arg Met Tyr Gly Cys Asp Leu Gly
        115                 120                 125

Pro Asp Gly Arg Leu Leu Arg Gly His Asp Gln Ser Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Ile Pro Ile Val Gly Ile Val Ala Gly Leu Ala Val Leu Ala Val
305                 310                 315                 320

Val Val Ile Gly Ala Val Val Ala Thr Val Met Cys Arg Arg Lys Ser
                325                 330                 335

Ser Gly Gly Lys Gly Gly Ser Tyr Ser Gln Ala Ala Ser Ser Asp Ser
            340                 345                 350

Ala Gln Gly Ser Asp Val Ser Leu Thr Ala
        355                 360
```

<210> SEQ ID NO 2
<211> LENGTH: 1009
<212> TYPE: DNA
<213> ORGANISM: Homo sapiens

<400> SEQUENCE: 2

| | | | | | |
|---|---|---|---|---|---|
| ctccatgagg | tatttctaca | ccgccatgtc | ccggcccggc | cgcggggagc | cccgcttcat | 60 |
| cgcagtgggc | tacgtggacg | acacccagtt | cgtgaggttc | gacagcgacg | ccgcgagtcc | 120 |
| gaggacggag | ccccgggcgc | catggataga | gcaggagggg | ccggagtatt | gggaccggaa | 180 |
| cacacagatc | ttcaagacca | acacacagac | ttaccgagag | agcctgcgga | acctgcgcgg | 240 |
| ctactacaac | cagagcgagg | ccgggtctca | catcatccag | aggatgtatg | gctgcgacct | 300 |
| ggggcccgac | gggcgcctcc | tccgcggca | tgaccagtcc | gcctacgacg | gcaaggatta | 360 |
| catcgccctg | aacgaggacc | tgagctcctg | gaccgcggcg | gacaccgcgg | ctcagatcac | 420 |
| ccagcgcaag | tgggaggcgg | cccgtgtggc | ggagcagctg | agagcctacc | tggagggcct | 480 |
| gtgcgtggag | tggctccgca | gataacctgga | gaacgggaag | gagacgctgc | agcgcgcgga | 540 |
| cccccccaaag | acacacgtga | cccaccaccc | cgtctctgac | catgaggcca | ccctgaggtg | 600 |
| ctgggccctg | ggcttctacc | tgcggagat | cacactgacc | tggcagcggg | atggcgagga | 660 |
| ccaaactcag | gacactgagc | ttgtggagac | cagaccagca | ggagatagaa | ccttccagaa | 720 |
| gtgggcagct | gtggtggtgc | cttctggaga | agagcagaga | tacacatgcc | atgtacagca | 780 |
| tgagggggctg | ccgaagcccc | tcaccctgag | atgggagcca | tcttcccagt | ccaccatccc | 840 |
| catcgtgggc | attgttgctg | gcctggctgt | cctagcagtt | gtggtcatcg | gagctgtggt | 900 |
| cgctactgtg | atgtgtagga | ggaagagctc | aggtggaaaa | ggagggagct | actctcaggc | 960 |
| tgcgtccagc | gacagtgccc | agggctctga | tgtgtctctc | acagcttga | | 1009 |

<210> SEQ ID NO 3
<211> LENGTH: 3327
<212> TYPE: DNA
<213> ORGANISM: Homo sapiens

<400> SEQUENCE: 3

| | | | | | |
|---|---|---|---|---|---|
| gatcaggacg | aagtcccagg | ccccgggcgg | ggctctcagg | gtctcaggct | ccgagagcct | 60 |
| tgtctgcatt | ggggaggcgc | agcgttgggg | attccccact | cccacgagtt | tcacttcttc | 120 |
| tcccaaccta | tgtcgggtcc | ttcttccagg | atactcgtga | cgcgtcccca | tttcccactc | 180 |
| ccattgggtg | tcggatatct | agagaagcca | atcagtgtcg | ccggggtccc | agttctaaag | 240 |
| tccccacgca | cccacccgga | ctcagaatct | cctcagacgc | cgagatgcgg | gtcacggcgc | 300 |
| cccgaaccgt | cctcctgctg | ctctgggggg | cagtggccct | gaccgagacc | tgggccggtg | 360 |
| agtgcggggt | cggagagggaa | atggcctctg | tggggaggag | cgagggggacc | gcaggcgggg | 420 |
| gcgcaggacc | tgaggagccg | cgccgggagg | agggtcgggc | gggtctcagc | ccctcctcgc | 480 |
| ccccaggctc | ccactccatg | aggtatttct | acaccgccat | gtcccggccc | ggccgcgggg | 540 |
| agccccgctt | catcgcagtg | ggctacgtgg | acgacaccca | gttcgtgagg | ttcgacagcg | 600 |
| acgccgcgag | tccgaggacg | gagccccggg | cgccatggat | agagcaggag | gggccggagt | 660 |
| attgggaccg | gaacacacag | atcttcaaga | ccaacacaca | gacttaccga | gagagcctgc | 720 |
| ggaacctgcg | cggctactac | aaccagagcg | aggccggtga | gtgaccccgg | ccggggcgc | 780 |
| aggtcacgac | tccccatccc | ccacgtacgg | cccgggtcgc | cccgagtctc | cgggtccgag | 840 |
| atccgcctcc | ctgaggccgc | gggacccgcc | cagaccctcg | accggcgaga | gcccaggcg | 900 |

```
cgtttacccg gtttcatttt cagttgaggc caaaatcccc gcgggttggt cggggcgggg      960
cggggctcgg gggacggggc tgaccgcggg gccggggcca gggtctcaca tcatccagag     1020
gatgtatggc tgcgacctgg ggcccgacgg gcgcctcctc cgcgggcatg accagtccgc     1080
ctacgacggc aaggattaca tcgccctgaa cgaggacctg agctcctgga ccgcggcgga     1140
caccgcggct cagatcaccc agcgcaagtg ggaggcggcc cgtgtggcgg agcagctgag     1200
agcctacctg gagggcctgt gcgtggagtg gctccgcaga tacctggaga cgggaaggga     1260
gacgctgcag cgcgcgggta ccaggggcag tggggagcct tccccatctc ctataggtcg     1320
ccggggatgg cctcccacga gaagaggagg aaaatgggat cagcgctaga atgtcgccct     1380
cccttgaatg gagaatggca tgagttttcc tgagtttcct ctgagggccc cctcttctct     1440
ctaggacaat taagggatga cgtctctgag gaaatggagg ggaagacagt ccctagaata     1500
ctgatcaggg gtccccttg accctgcag cagccttggg aaccgtgact tttcctctca     1560
ggccttgttc tctgcctcac actcagtgtg tttggggctc tgattccagc acttctgagt     1620
cactttacct ccactcagat caggagcaga agtccctgtt ccccgctcag agactcgaac     1680
tttccaatga ataggagatt atcccaggtg cctgcgtcca ggctggtgtc tgggttctgt     1740
gccccttccc cacaccaggt gtcctgtcca ttctcaggct ggtcacatgg gtggtcctag     1800
ggtgtcccat gagagatgca aagcgcctga attttctgac tcttcccatc agaccccca     1860 aagacacacg tgacccacca ccccgtctct gaccatgagg ccaccctgag gtgctgggcc     1920
ctgggcttct accctgcgga gatcacactg acctggcagc gggatggcga ggaccaaact     1980
caggacactg agcttgtgga gaccagacca gcaggagata gaaccttcca gaagtgggca     2040
gctgtggtgg tgccttctgg agaagagcag agatacacat gccatgtaca gcatgagggg     2100
ctgccgaagc ccctcaccct gagatggggt aaggagggg atgagggtc atatctcttc     2160 tcagggaaag caggagccct tctggagccc ttcagcaggg tcaggccccc tcgtcttccc     2220 ctccttcc agagccatct tcccagtcca ccatccccat cgtgggcatt gttgctggcc     2280
tggctgtcct agcagttgtg gtcatcggag ctgtggtcgc tactgtgatg tgtaggagga     2340
agagctcagg tagggaaggg gtgaggggtg gggtctgggt tttcttgtcc cactgggggt     2400
ttcaagcccc aggtagaagt gttccctgcc tcattactgg gaagcagcat ccacacaggg     2460
gctaacgcag cctgggaccc tgtgtgccag cacttactct tttgtgcagc acatgtgaca     2520
atgaaggacg gatgtatcac cttgatggtt gtggtgttgg ggtcctgatt tcagcattca     2580
tgagtcaggg gaaggtccct gctaaggaca gaccttagga gggcagttgg tccaggaccc     2640
acacttgctt tcctcgtgtt tcctgatcct gccttgggtc tgtagtcata cttctggaaa     2700
ttccttttgg gtccaagacg aggaggttcc tctaagatct catggccctg cttcctccca     2760
gtcccctcac aggacatttt cttcccacag gtggaaaagg agggagctac tctcaggctg     2820
cgtgtaagtg gtgggggtgg gagtgtggag gagctcaccc accccataat tcctcctgtc     2880
ccacgtctcc tgcgggctct gaccaggtcc tgttttgtt ctactccagc cagcgacagt     2940
gcccagggct ctgatgtgtc tctcacagct tgaaaggtg agattcttgg ggtctagagt     3000 gggcggggg ggcgggagg gggcagaggg gaaaggcctg ggtaatggag attctttgat     3060
tgggatgttt cgcgtgtgtc gtgggctgtt cagagtgtca tcacttacca tgactaacca     3120
gaatttgttc atgactgttg ttttctgtag cctgagacag ctgtcttgtg agggactgag     3180
atgcaggatt tcttcactcc tcccctttgt gacttcaagg gcctctggca tctctttctg     3240
```

```
caaaggcacc tgaatgtgtc tgcgtccctg ttagcctaat gtgaggaggt ggagagacag    3300 cccaccccg tgtccactgt gaccct                                          3327
```

<210> SEQ ID NO 4
<211> LENGTH: 365
<212> TYPE: PRT
<213> ORGANISM: Homo sapiens

<400> SEQUENCE: 4

```
Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
```

<210> SEQ ID NO 5
<211> LENGTH: 1098
<212> TYPE: DNA
<213> ORGANISM: Homo sapiens

<400> SEQUENCE: 5

| | | | | | |
|---|---|---|---|---|---|
| atggccgtca | tggcgccccg | aaccctcgtc | ctgctactct | cggggggctct | ggccctgacc | 60 |
| cagacctggg | cgggctctca | ctccatgagg | tatttcttca | catccgtgtc | ccggcccggc | 120 |
| cgcggggagc | cccgcttcat | cgcagtgggc | tacgtggacg | acacgcagtt | cgtgcggttc | 180 |
| gacagcgacg | ccgcgagcca | gaggatggag | ccgcgggcgc | cgtggataga | gcaggagggt | 240 |
| ccggagtatt | gggacgggga | gacacggaaa | gtgaaggccc | actcacagac | tcaccgagtg | 300 |
| gacctgggga | ccctgcgcgg | ctactacaac | cagagcgagg | ccggttctca | caccgtccag | 360 |
| aggatgtatg | gctgcgacgt | ggggtcggac | tggcgcttcc | tccgcgggta | ccaccagtac | 420 |
| gcctacgacg | gcaaggatta | catcgccctg | aaagaggacc | tgcgctcttg | gaccgcggcg | 480 |
| gacatggcag | ctcagaccac | caagcacaag | tgggaggcgg | cccatgtggc | ggagcagttg | 540 |
| agagcctacc | tggagggcac | gtgcgtggag | tggctccgca | gatacctgga | gaacgggaag | 600 |
| gagacgctgc | agcgcacgga | cgcccccaaa | acgcatatga | ctcaccacgc | tgtctctgac | 660 |
| catgaagcca | ccctgaggtg | ctgggccctg | agcttctacc | ctgcggagat | cacactgacc | 720 |
| tggcagcggg | atggggagga | ccagacccag | gacacggagc | tcgtggagac | caggcctgca | 780 |
| ggggatggaa | ccttccagaa | gtgggcggct | gtggtggtgc | cttctggaca | ggagcagaga | 840 |
| tacacctgcc | atgtgcagca | tgagggtttg | cccaagcccc | tcaccctgag | atgggagccg | 900 |
| tcttcccagc | ccaccatccc | catcgtgggc | atcattgctg | gcctggttct | ctttggagct | 960 |
| gtgatcactg | gagctgtggt | cgctgctgtg | atgtggagga | ggaagagctc | agatagaaaa | 1020 |
| ggagggagct | actctcaggc | tgcaagcagt | gacagtgccc | agggctctga | tgtgtctctc | 1080 |
| acagcttgta | aagtgtga | | | | | 1098 |

<210> SEQ ID NO 6
<211> LENGTH: 254
<212> TYPE: PRT
<213> ORGANISM: Homo sapiens

<400> SEQUENCE: 6

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Cys Ala Val Phe
        35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
            85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

```
Asp Thr Lys Glu Leu Val Val Ala Lys Ala Gly Val Tyr Tyr Val Phe
    130                 135                 140
Phe Gln Leu Glu Leu Arg Arg Val Val Ala Gly Glu Gly Ser Gly Ser
145                 150                 155                 160
Val Ser Leu Ala Leu His Leu Gln Pro Leu Arg Ser Ala Ala Gly Ala
                165                 170                 175
Ala Ala Leu Ala Leu Thr Val Asp Leu Pro Pro Ala Ser Ser Glu Ala
                180                 185                 190
Arg Asn Ser Ala Phe Gly Phe Gln Gly Arg Leu Leu His Leu Ser Ala
                195                 200                 205
Gly Gln Arg Leu Gly Val His Leu His Thr Glu Ala Arg Ala Arg His
    210                 215                 220
Ala Trp Gln Leu Thr Gln Gly Ala Thr Val Leu Gly Leu Phe Arg Val
225                 230                 235                 240
Thr Pro Glu Ile Pro Ala Gly Leu Pro Ser Pro Arg Ser Glu
                245                 250

<210> SEQ ID NO 7
<211> LENGTH: 1619
<212> TYPE: DNA
<213> ORGANISM: Homo sapiens

<400> SEQUENCE: 7
gtcatggaat acgcctctga cgcttcactg gaccccgaag ccccgtggcc tcccgcgccc     60
cgcgctcgcg cctgccgcgt actgccttgg gccctggtcg cggggctgct gctgctgctg    120
ctgctcgctg ccgcctgcgc cgtcttcctc gcctgcccct gggccgtgtc cggggctcgc    180
gcctcgcccg gctccgcggc cagcccgaga ctccgcgagg gtcccgagct tcgcccgac     240 gatcccgccg gcctcttgga cctgcggcag ggcatgtttg cgcagctggt ggcccaaaat    300
gttctgctga tcgatgggcc cctgagctgg tacagtgacc caggcctggc aggcgtgtcc    360
ctgacggggg gcctgagcta caagaggac acgaaggagc tggtggtggc caaggctgga    420
gtctactatg tcttctttca actagagctg cggcgcgtgg tggccggcga gggctcaggc    480
tccgtttcac ttgcgctgca cctgcagcca ctgcgctctg ctgctgggc cgccgccctg    540 gctttgaccg tggacctgcc acccgcctcc tccgaggctc ggaactcggc cttcggtttc    600
cagggccgct tgctgcacct gagtgccggc agcgcctgg gcgtccatct tcacactgag    660
gccagggcac gccatgcctg gcagcttacc cagggcgcca cagtcttggg actcttccgg    720 gtgaccccg aaatcccagc cggactccct tcaccgaggt cggaataacg cccagcctgg    780
gtgcagccca cctggacaga gtccgaatcc tactccatcc ttcatggaga cccctggtgc    840
tgggtccctg ctgctttctc tacctcaagg ggcttggcag gggtccctgc tgctgacctc    900
cccttgagga ccctcctcac ccactccttc cccaagttgg accttgatat ttattctgag    960
cctgagctca gataatatat tatatatatt atatatatat atatatttct atttaaagag   1020
gatcctgagt ttgtgaatgg actttttag aggagttgtt ttgggggggg ggtcttcgac    1080
attgccgagg ctggtcttga actcctggac ttagacgatc ctcctgcctc agcctcccaa   1140
gcaactggga ttcatccttt ctattaattc attgtactta tttgcctatt tgtgtgtatt   1200
gagcatctgt aatgtgccag cattgtgccc aggctagggg gctatagaaa catctagaaa   1260
tagactgaaa gaaatctga gttatggtaa tacgtgagga atttaaagac tcatccccag   1320
cctccacctc ctgtgtgata cttggggct agcttttttc tttctttctt tttttgaga   1380
```

```
tggtcttgtt ctgtcaacca ggctagaatg cagcggtgca atcatgagtc aatgcagcct    1440
ccagcctcga cctcccgagg ctcaggtgat cctcccatct cagcctctcg agtagctggg    1500
accacagttg tgtgccacca cacttggcta acttttttaat tttttttgcgg agacggtatt   1560 gctatgttgc caaggttgtt tacatgccag tacaatttat aataaacact cattttttcc    1619

<210> SEQ ID NO 8
<211> LENGTH: 20
<212> TYPE: DNA
<213> ORGANISM: Homo sapiens

<400> SEQUENCE: 8
actaccatca acttcactcg                                                   20

<210> SEQ ID NO 9
<211> LENGTH: 18
<212> TYPE: DNA
<213> ORGANISM: Homo sapiens

<400> SEQUENCE: 9
ctcccatcat acacctcc                                                     18

<210> SEQ ID NO 10
<211> LENGTH: 18
<212> TYPE: DNA
<213> ORGANISM: Homo sapiens

<400> SEQUENCE: 10
tggaggacca gaggcccc                                                     18

<210> SEQ ID NO 11
<211> LENGTH: 22
<212> TYPE: DNA
<213> ORGANISM: Homo sapiens

<400> SEQUENCE: 11
ggacgattat caggaggcct gc                                                22

<210> SEQ ID NO 12
<211> LENGTH: 21
<212> TYPE: DNA
<213> ORGANISM: Homo sapiens

<400> SEQUENCE: 12
gttctacctc gccatgcctt t                                                 21

<210> SEQ ID NO 13
<211> LENGTH: 21
<212> TYPE: DNA
<213> ORGANISM: Homo sapiens

<400> SEQUENCE: 13
gcagtcagtc ggatagtcag t                                                 21

<210> SEQ ID NO 14
<211> LENGTH: 765
<212> TYPE: DNA
<213> ORGANISM: Homo sapiens

<400> SEQUENCE: 14
atggaatatg catccgatgc ctcccttgac cctgaagcac cttggcctcc cgcccccaga     60
gcacgagctt gtagagttct cccttgggcc cttgtcgctg gacttctcct tctcctcctt    120
```

```
ctcgccgccg cctgtgcagt gttccttgca tgtccttggg ccgtttctgg tgccagagcc    180
tcacctggaa gtgcagcatc tccccgactt cgcgaaggtc cagaactttc ccccgatgat    240
cctgccggac tccttgactt gcgccaaggc atgtttgctc agctcgtagc acagaatgtc    300
ctcctcattg acggtcccct ttcatggtat tctgatccag gcctcgctgg cgtttccctt    360
actggcggtc tgtcctataa agaagatacc aaagaacttg tcgttgctaa ggccggtgtt    420
tactacgttt ttttcagct cgaactccgc agagtcgtcg ccggcgaagg atccggttct    480
gttagtctcg cacttcatct ccagcccctc agatcagccg caggagctgc cgccctcgcc    540
ctcactgttg acctcccacc tgcctcctca gaagctagaa attccgcgtt tggttttcag    600
ggaagactcc ttcatctgtc cgctggccaa cgattgggtg tccatctcca taccgaagct    660
cgcgcgcgac acgcatggca actcacacag ggcgctactg tacttggcct ctttagagta    720
acacccgaaa ttcctgccgg tttgccctcc ccccgatccg aataa    765

<210> SEQ ID NO 15
<211> LENGTH: 8058
<212> TYPE: DNA
<213> ORGANISM: Artificial Sequence
<220> FEATURE:
<223> OTHER INFORMATION: Expression vector

<400> SEQUENCE: 15
ccatggccgt catggcgccc cgaaccctcg tcctgctact ctcgggggct ctggccctga     60
cccagacctg gcggggctct cactccatga ggtatttcta cacctccgtg tcccggcccg    120
gccgcgggga gccccgcttc atcgcagtgg gctacgtgga acacacgcag ttcgtgcggt    180
tcgacagcga cgccgcgagc cagaggatgg agccgcgggc gccgtggata gagcaggagg    240
gtccggagta ttgggacggg agagacacgg aagtgaaggc ccactcacag actcaccgag    300
tggacctggg gaccctgcgc ggctactaca accagagcga ggccggttct cacaccgtcc    360
agaggatgta tggctgcgac gtggggtcgg actggcgctt cctccgcggg taccaccagt    420
acgcctacga cggcaaggat tacatcgccc tgaaagagga cctgcgctct tggaccgcgg    480
cggacatggc agctcagacc accaagcaca gtgggaggc ggcccatgtg gcggagcagt    540
tgagagccta cctggagggc acgtgcgtgg agtggctccg cagatacctg gagaacggga    600
aggagacgct gcagcgcacg gacgcccca aaacgcatat gactcaccac gctgtctctg    660
accatgaagc cacctgagg tgctgggccc tgagcttcta ccctgcggag atcacactga    720
cctggcagcg ggatggggag gaccagaccc aggacacgga gctcgtggag accaggcctg    780
caggggatgg aaccttccag aagtgggcgg ctgtggtggt gccttctgga caggagcaga    840
gatacacctg ccatgtgcag catgagggtt tgcccaagcc cctcaccctg agatgggagc    900
cgtcttccca gcccaccatc cccatcgtgg gcatcattgc tggcctggtt ctctttggag    960
ctgtgatcac tggagctgtg gtcgctgctg tgatgtggag gaggaagagc tcagatagaa   1020
aaggagggag ctactctcag gctgcaagca gtgacagtgc ccaggctct gatgtgtctc   1080 tcacagcttg taaagtgtga gcggccgctc gactgcagga attaattccg cccctctccc   1140 tcccccccc ctaacgttac tggccgaagc cgcttggaat aaggccggtg tgtgtttgtc   1200
tatatgtgat tttccaccat attgccgtct tttggcaatg tgagggcccg gaaacctggc   1260
cctgtcttct tgacgagcat cctagggggt ctttcccctc tcgccaaagg aatgcaaggt   1320
ctgttgaatg tcgtgaagga agcagttcct ctggaagctt cttgaagaca aacaacgtct   1380
```

```
gtagcgaccc tttgcaggca gcggaacccc ccacctggcg acaggtgcct ctgcggccaa      1440
aagccacgtg tataagatac acctgcaaag gcggcacaac cccagtgcca cgttgtgagt      1500
tggatagttg tggaaagagt caaatggctc tcctcaagcg tagtcaacaa ggggctgaag      1560
gatgcccaga aggtacccca ttgtatggga atctgatctg gggcctcggt gcacatgctt      1620
tacatgtgtt tagtcgaggt taaaaaagct ctaggccccc cgaaccacgg ggacgtggtt      1680
ttcctttgaa aaacacgatg ataagcttgc cacaaccatg ggatcggcca ttgaacaaga      1740
tggattgcac gcaggttctc cggccgcttg ggtggagagg ctattcggct atgactgggc      1800
acaacagaca atcggctgct ctgatgccgc cgtgttccgg ctgtcagcgc aggggcgccc      1860
ggttcttttt gtcaagaccg acctgtccgg tgccctgaat gaactgcagg acgaggcagc      1920
gcggctatcg tggctggcca cgacgggcgt tccttgcgca gctgtgctcg acgttgtcac      1980
tgaagcggga agggactggc tgctattggg cgaagtgccg gggcaggatc tcctgtcatc      2040
tcaccttgct cctgccgaga agtatccat catggctgat gcaatgcggc ggctgcatac      2100
gcttgatccg gctacctgcc cattcgacca ccaagcgaaa catcgcatcg agcgagcacg      2160
tactcggatg gaagccggtc ttgtcgatca ggatgatctg gacgaagagc atcaggggct      2220
cgcgccagcc gaactgttcg ccaggctcaa ggcgcgcatg cccgacggcg aggatctcgt      2280
cgtgacccat ggcgatgcct gcttgccgaa tatcatggtg aaaatggcc gcttttctgg      2340 attcatcgac tgtggccggc tgggtgtggc ggaccgctat caggacatag cgttggctac      2400
ccgtgatatt gctgaagagc ttggcggcga atgggctgac cgcttcctcg tgctttacgg      2460
tatcgccgct cccgattcgc agcgcatcgc cttctatcgc cttcttgacg agttcttctg      2520
agggatccga taaataaaa gattttattt agtctccaga aaagggggg aatgaaagac      2580 cccacctgta ggtttggcaa gctagcttaa gtaacgccat tttgcaaggc atggaaaata      2640
cataactgag aatagagaag ttcagatcaa ggttaggaac agagagacag cagaatatgg      2700
gccaaacagg atatctgtgg taagcagttc ctgccccgc tcagggccaa gaacagatgg      2760
tccccagatg cggtcccgcc ctcagcagtt tctagagaac catcagatgt ttccagggtg      2820
ccccaaggac ctgaaaatga ccctgtgcct tatttgaact aaccaatcag ttcgcttctc      2880
gcttctgttc gcgcgcttct gctccccgag ctcaataaaa gagcccacaa ccctcactc      2940 ggcgcgccag tcctccgata gactgcgtcg cccgggtacc cgtgtatcca ataaaccctc      3000
ttgcagttgc atccgacttg tggtctcgct gttccttggg agggtctcct ctgagtgatt      3060 gactaccgt cagcggggt ctttcatggg taacagtttc ttgaagttgg agaacaacat      3120
tctgagggta ggagtcgaat attaagtaat cctgactcaa ttagccactg ttttgaatcc      3180
acatactcca atactcctga aatccatcga tggagttcat tatggacagc gcagaaagag      3240
ctggggagaa ttgtgaaatt gttatccgct cacaattcca cacaacatac gagccggaag      3300
cataaagtgt aaagcctggg gtgcctaatg agtgagctaa ctcacattaa ttgcgttgcg      3360
ctcactgccc gctttccagt cgggaaacct gtcgtgccag ctgcattaat gaatcggcca      3420
acgcgcgggg agaggcggtt tgcgtattgg gcgctcttcc gcttcctcgc tcactgactc      3480
gctgcgctcg tcgttcggc tgcggcgagc ggtatcagct cactcaaagg cggtaatacg      3540
gttatccaca gaatcagggg ataacgcagg aaagaacatg tgagcaaaag gccagcaaaa      3600
ggccaggaac cgtaaaaagg ccgcgttgct ggcgtttttc cataggctcc gcccccctga      3660
cgagcatcac aaaaatcgac gctcaagtca gaggtggcga aacccgacag gactataaag      3720
ataccaggcg tttccccctg gaagctccct cgtgcgctct cctgttccga ccctgccgct      3780
```

```
taccggatac ctgtccgcct ttctcccttc gggaagcgtg gcgctttctc atagctcacg   3840
ctgtaggtat ctcagttcgg tgtaggtcgt tcgctccaag ctgggctgtg tgcacgaacc   3900
ccccgttcag cccgaccgct gcgccttatc cggtaactat cgtcttgagt ccaacccggt   3960
aagacacgac ttatcgccac tggcagcagc cactggtaac aggattagca gagcgaggta   4020
tgtaggcggt gctacagagt tcttgaagtg gtggcctaac tacggctaca ctagaaggac   4080
agtatttggt atctgcgctc tgctgaagcc agttaccttc ggaaaaagag ttggtagctc   4140
ttgatccggc aaacaaacca ccgctggtag cggtggtttt tttgtttgca agcagcagat   4200
tacgcgcaga aaaaaggat ctcaagaaga tcctttgatc ttttctacgg ggtctgacgc   4260
tcagtggaac gaaaactcac gttaagggat tttggtcatg agattatcaa aaaggatctt   4320
cacctagatc cttttaaatt aaaaatgaag ttttaaatca atctaaagta tatatgagta   4380
aacttggtct gacagttacc aatgcttaat cagtgaggca cctatctcag cgatctgtct   4440
atttcgttca tccatagttg cctgactccc cgtcgtgtag ataactacga tacgggaggg   4500
cttaccatct ggccccagtg ctgcaatgat accgcgagac ccacgctcac cggctccaga   4560
tttatcagca ataaaccagc cagccggaag ggccgagcgc agaagtggtc ctgcaacttt   4620
atccgcctcc atccagtcta ttaattgttg ccgggaagct agagtaagta gttcgccagt   4680
taatagtttg cgcaacgttg ttgccattgc tacaggcatc gtggtgtcac gctcgtcgtt   4740
tggtatggct tcattcagct ccggttccca acgatcaagg cgagttacat gatccccat   4800 gttgtgcaaa aaagcggtta gctccttcgg tcctccgatc gttgtcagaa gtaagttggc   4860
cgcagtgtta tcactcatgg ttatggcagc actgcataat tctcttactg tcatgccatc   4920
cgtaagatgc ttttctgtga ctggtgagta ctcaaccaag tcattctgag aatagtgtat   4980
gcggcgaccg agttgctctt gcccggcgtc aatacgggat aataccgcgc cacatagcag   5040
aactttaaaa gtgctcatca ttggaaaacg ttcttcgggg cgaaaactct caaggatctt   5100
accgctgttg agatccagtt cgatgtaacc cactcgtgca cccaactgat cttcagcatc   5160
ttttactttc accagcgttt ctgggtgagc aaaaacagga aggcaaaatg ccgcaaaaaa   5220
gggaataagg gcgacacgga aatgttgaat actcatactc ttcctttttc aatattattg   5280
aagcatttat cagggttatt gtctcatgag cggatacata tttgaatgta tttagaaaaa   5340
taaacaaata ggggttccgc gcacatttcc ccgaaaagtg ccacctgacg tctaagaaac   5400
cattattatc atgacattaa cctataaaaa taggcgtatc acgaggccct ttcgtctcgc   5460
gcgtttcggt gatgacggtg aaaacctctg acacatgcag ctcccggaga cggtcacagc   5520
ttgtctgtaa gcggatgccg ggagcagaca gcccgtcag ggcgcgtcag cgggtgttgg   5580
cgggtgtcgg gctggctta actatgcggc atcagagcag attgtactga gagtgcacca   5640
tatgcggtgt gaaataccgc acagatgcgt aaggagaaaa taccgcatca ggcgccattc   5700
gccattcagg ctgcgcaact gttgggaagg cgatcggtg cgggcctctt cgctattacg   5760
ccagctggcg aaagggggat gtgctgcaag gcgattaagt tgggtaacgc cagggttttc   5820
ccagtcacga cgttgtaaaa cgacggccag tgccacgctc tcccttatgc gactcctgca   5880
ttaggaagca gcccagtagt aggttgaggc cgttgagcac cgccgccgca aggaatggtg   5940
catgcaagga gatggcgccc aacagtcccc cggccacggg gcctgccacc atacccacgc   6000
cgaaacaagc gctcatgagc ccgaagtggc gagcccgatc ttccccatcg gtgatgtcgg   6060
cgatataggc gccagcaacc gcacctgtgg cgccggtgat gccggccacg atgcgtccgg   6120
```

```
cgtagaggcg atttaaagac aggatatcag tggtccaggc tctagttttg actcaacaat    6180
atcaccagct gaagcctata gagtacgagc catagataaa ataaaagatt ttatttagtc    6240
tccagaaaaa gggggaatg aaagacccca cctgtaggtt tggcaagcta gcttaagtaa     6300
cgccattttg caaggcatgg aaaatacata actgagaata gagaagttca gatcaaggtt    6360
aggaacagag agacagcaga atatgggcca aacaggatat ctgtggtaag cagttcctgc    6420
cccggctcag ggccaagaac agatggtccc cagatgcggt cccgccctca gcagtttcta    6480
gagaaccatc agatgtttcc agggtgcccc aaggacctga aaatgaccct gtgccttatt    6540
tgaactaacc aatcagttcg cttctcgctt ctgttcgcgc gcttctgctc cccgagctca    6600
ataaaagagc ccacaacccc tcactcggcg cgccagtcct ccgatagact gcgtcgcccg    6660
ggtacccgta ttcccaataa agcctcttgc tgtttgcatc cgaatcgtgg actcgctgat    6720
ccttgggagg gtctcctcag attgattgac tgcccacctc gggggtcttt catttggagg    6780
ttccaccgag atttggagac ccctgcctag ggaccaccga cccccccgcc gggaggtaag    6840
ctggccagcg gtcgtttcgt gtctgtctct gtctttgtgc gtgtttgtgc cggcatctaa    6900
tgtttgcgcc tgcgtctgta ctagttagct aactagctct gtatctggcg gacccgtggt    6960
ggaactgacg agttcggaac acccggccgc aaccctggga gacgtccag ggacttcggg     7020 ggccgttttt gtggcccgac ctgagtccaa aaatcccgat cgttttggac tctttggtgc    7080 accccccctta gaggagggat atgtggttct ggtaggagac gagaacctaa aacagttccc    7140
gcctccgtct gaatttttgc tttcggtttg ggaccgaagc cgcgccgcgc gtcttgtctg    7200
ctgcagcatc gttctgtgtt gtctctgtct gactgtgttt ctgtatttgt ctgagaatat    7260
gggcccgggc tagcctgtta ccactccctt aagtttgacc ttaggtcact ggaaagatgt    7320
cgagcggatc gctcacaacc agtcggtaga tgtcaagaag agacgttggg ttaccttctg    7380
ctctgcagaa tggccaacct ttaacgtcgg atggccgcga gacggcacct ttaaccgaga    7440
cctcatcacc caggttaaga tcaaggtctt ttcacctggc ccgcatggac acccagacca    7500
ggtcccctac atcgtgacct gggaagcctt ggcttttgac ccccctccct gggtcaagcc    7560
ctttgtacac cctaagcctc cgcctcctct tcctccatcc gccccgtctc tcccccttga    7620
acctcctcgt tcgaccccgc ctcgatcctc cctttatcca gccctcactc cttctctagg    7680
cgcccatatg agatcttata tggggcaccc ccgcccttg taaacttccc tgaccctgac     7740
atgacaagag ttactaacag cccctctctc caagctcact tacaggctct ctacttagtc    7800
cagcacgaag tctggagacc tctggcggca gcctaccaag aacaactgga ccgaccggtg    7860
gtacctcacc cttaccgagt cggcgacaca gtgtgggtcc gccgacacca gactaagaac    7920
ctagaacctc gctggaaagg accttacaca gtcctgctga ccaccccac cgccctcaaa     7980 gtagacggca tcgcagcttg gatacacgcc gcccacgtga aggctgccga ccccggggt    8040 ggaccatcct ctagaccg                                                  8058
```

ALLOGENEIC TUMOR CELL VACCINATION

FIELD OF THE INVENTION

The present invention relates to cancer immunotherapy, specifically to allogeneic tumor cell vaccines, and provides therapeutic and diagnostic compositions and methods for use in proliferative disorders.

BACKGROUND OF THE INVENTION

Cell vaccines are prepared from tumor cell lines that are cultured in vitro. The vaccine product is designed to contain one or more antigens that are unique to cells; some preparations also contain "adjuvants" thought to enhance the immunogenicity of the preparation.

Whole cell vaccines have several advantages for tumor immunity. They are composed of a large array of antigens, identified ones as well as not yet defined ones, and they are relatively easy to produce. The inventors previously showed that an autologous vaccine of dinitrophenyl (DNP)-modified melanoma cells, improved disease-free (DFS) and overall survival (OS) in post-operative high risk adjuvant patients who successfully attained anti-melanoma reactivity as detected by positive delayed type hypersensitivity reactions to unmodified melanoma cells (Lotem et al., 2009). One drawback of the autologous vaccine is the fact that cancer patients often lack an available source of tumor for the growth of tumor cell lines. A vaccine derived from allogeneic tumor cell lines could overcome this obstacle. This approach led in the past to the production of an allogeneic vaccine that compared favorably with the adjuvant effect of maximally-tolerated doses of interferon alpha (Mitchell et al., 2007), with significantly lower treatment-related toxicity.

Most allogeneic vaccines used thus far did not take into consideration the need for HLA (human leukocyte antigen molecules) matching between the tumor of the donor and the recipient (Chapman et al., (2007). HLA antigens play a crucial role in presenting peptides derived from self and foreign proteins in a form that is recognized by T cells. Thus, matching the HLA phenotype of the donor cells and the recipient is essential for efficient cell-mediated cytotoxicity in response to vaccine treatment. In the absence of HLA compatibility, vaccines rely for their immune effect on the mediation of secondary antigen presenting cells (APC) to process and present antigens in conjunction with the host's HLA. Antigen presentation by APC may favor CD4 responses, inducing regulatory T cells side by side with helper T cell populations (Morelli et al., 2006). Nevertheless, it should be noted that APC presentation may also facilitate CD8 responses.

Various approaches for developing tumor cell vaccines have been disclosed. For example, EP2404614 discloses a composition for stimulating an immune response in patients having different types of cancer comprising a combination of allogeneic tumor cells and/or tumor stem cells that are selected on the basis of secreting at least one immunosuppressive agent, e.g., TGF-β, and that are genetically modified to reduce or inhibit the expression of said at least one immunosuppressive agent, and that collectively express a spectrum of tumor associated antigens, and a physiologically acceptable carrier.

US Patent Publication No. 2010/055136 discloses a composition for the treatment or prevention of a tumor, comprising: (i) allogeneic or xenogeneic tumor cells; (ii) a lysate of a syngeneic tumor cell; and (iii) a pharmaceutically acceptable excipient.

US Patent Publication No. 2010/119537 discloses a method of producing a protective immune response in a human subject comprising administering to the subject an effective amount of lung cancer cells transfected with a eukaryotic expression vector derived from the bovine papilloma virus comprising a nucleic acid encoding CD80 (B7.1) and with a eukaryotic expression vector derived from the bovine papilloma virus comprising a nucleic acid encoding an HLA antigen.

U.S. Pat. No. 5,882,654 discloses a pharmaceutically acceptable polyvalent melanoma cell composition for injection, the composition comprising viable cells of one or more allogeneic melanoma call lines which cells have been rendered incapable of proliferation in vivo and which provide to the composition an amount of melanoma associated antigens effective to stimulate an antitumor immune response, the composition including the specific melanoma associated antigens GD2 ganglioside, GM2 ganglioside, M-TAA, M-fetal antigen and M-urinary antigen in amounts effective to stimulate an immune response against each of said specific antigens.

WO9003183 discloses an immunotherapeutic melanoma tumor vaccine comprising: a melanoma cell lysate produced from allogeneic melanoma tumor cells; and an adjuvant comprising a refined detoxified endotoxin and at least one biological immunostimulant selected from the group consisting of mycobacterial cell wall skeleton, trehalose dimycolate, pyridine soluble extract of a microorganism, and mixtures thereof.

Initial attempts to develop allogeneic cell vaccines for clinical use in melanoma patients have been reported. Specifically, polyvalent melanoma whole cell vaccines have been evaluated (Morton et al., 1992; Morton et al., 2002; Barth et al., 1994; Bystryn et al., 1992). Hoon et al. report the survival data of melanoma patients receiving a polyvalent melanoma cell vaccine comprising three irradiated cell lines. The publication reports that expression of the HLA B35 by the recipient patients was correlated with a poor survival outcome following vaccination (Hoon et al., 1998). A genetically modified allogeneic cancer vaccine, GVAX, has been developed by Cell Genesys. GVAX is an allogeneic cancer vaccine composed of lethally irradiated whole cancer cells that are genetically modified to secrete granulocyte-macrophage colony-stimulating factor (GM-CSF). This platform is currently undergoing multiple clinical trials. Initial clinical results with Canvaxin, a polyvalent, whole-cell vaccine derived from three melanoma cell lines were encouraging, demonstrating prolonged survival in a subset of patients receiving the vaccine (Morton et al. 1992, 2002). However, phase III study of Canvaxin versus Bacillus Calmette-Guerin (BCG) closed prematurely after interim analysis (Riker et al., 2007). Thus, additional means for improving the efficacy of tumor cell vaccines including melanoma cell vaccines are clearly required.

There remains an unmet medical need for providing improved immunotherapy for treatment of proliferative disorders, specifically metastatic cancer. Development of new and effective whole cell vaccines, and of assays useful for selecting patients that are likely benefit from treatment with such vaccines, would be highly advantageous.

SUMMARY OF THE INVENTION

The present invention relates to cancer immunotherapy, specifically to allogeneic tumor cell vaccines. According to some embodiments, the invention provides novel cell lines useful as therapeutic cell vaccine compositions. The invention further provides advantageous screening methods and means for identifying patients amenable for treatment with partially Human Leukocyte Antigen (HLA) matched allogeneic cell vaccines. Therapeutic compositions and methods for use in proliferative disorders are further provided.

The invention is based, in part, on the surprising discovery of a positive correlation between a favorable disease outcome and a specific HLA phenotype, in cancer patients receiving allogeneic tumor cell vaccines. The present invention discloses the survival data of forty two melanoma patients at high risk for disease recurrence who received an allogeneic vaccine composed of a combination of three melanoma cell lines, each matching at least one allele of the recipient's HLA-A and -B loci. Surprisingly, patients bearing HLA-B35 had significantly better overall survival (OS) and disease free survival (DFS) than those bearing other HLA alleles (OS of 100% and DFS of 90% versus 56% and 23% respectively for the non-B35 patients).

Consequently, the invention is further based, in part, on the development and isolation of novel cancer cell lines that advantageously express the B35 HLA allele, having particularly favorable properties for use as whole cell cancer immunotherapy. These cells display unique profiles of HLA alleles and tumor associated antigens (TAA) at high expression levels, and have enhanced immunogenicity compared to other cell lines. In addition, embodiments of the invention are further based in part on the unexpected discovery that genetically modified melanoma cells displaying HLA B35 and A2 and expressing a 4-1 BB ligand (4-1BBL) transgene, showed an improved ability to stimulate tumor infiltrating lymphocytes as determined by IFN-γ secretion.

A first aspect of the invention is directed to methods for assessing or evaluating the prognosis of a subject afflicted with cancer following allogeneic tumor cell vaccination, and of identifying subjects amenable for treatment with allogeneic tumor cell vaccination. The methods according to this aspect comprise assessing the presence of the B35 HLA phenotype in the subject, wherein the presence of the B35 HLA phenotype indicates a favorable disease outcome following allogeneic tumor cell vaccination.

Thus, according to some embodiments there is provided a method for predicting a favorable disease outcome following an allogeneic tumor cell vaccination, which method for predicting comprises assessing the presence of the B35 HLA phenotype in a sample of the subject, wherein the presence of the B35 HLA phenotype indicates a favorable disease outcome following vaccination.

According to other embodiments provided is a method for identifying a subject that will respond therapeutically to a method of treating cancer comprising administering one or more tumor cell lines allogeneic to the subject, which method for identifying comprises: determining the expression of the B35 HLA allele in a sample obtained from said subject, wherein expression of the B35 HLA allele indicates that said subject will respond therapeutically to the method of treating cancer.

According to embodiments of these methods said subject may be afflicted with a carcinoma, optionally a metastatic carcinoma. In a particular embodiment the subject is afflicted with melanoma.

The method of treating or tumor cell vaccination may be affected by administering to said subject one or more cell lines that are allogeneic to said subject. In some embodiments, the one or more cell lines express at least one HLA allele identical to the HLA alleles of said subject. According to alternate or additional embodiments, the one or more cell lines further express at least one HLA allele that is not identical to the HLA alleles of said subject. In other embodiments, the one or more cell lines endogenously or exogenously express the HLA-B35 allele. In further embodiments, the one or more cell lines endogenously or exogenously express the HLA-B35 and A2 alleles. According to additional embodiments, said one or more cell lines endogenously or exogenously express 4-1 BB ligand (4-1BBL). In other embodiments, the one or more cell lines are selected from the novel tumor cell lines of the invention as described hereinbelow.

In another embodiment, the invention relates to a method of treating cancer in a subject in need thereof, comprising identifying the subject that will respond therapeutically to the method of treating cancer (or a subject predicted to have a favorable disease outcome following an allogeneic tumor cell vaccination) as defined herein, and administering to said subject an immunogenic composition comprising one or more tumor cell lines allogeneic to said subject. In certain embodiments, the one or more cell lines are selected from the novel tumor cell lines of the invention as described hereinbelow.

The invention relates, in another aspect, to novel tumor cell lines having advantageous properties for use as tumor cell vaccines and immunogenic therapeutic compositions for adjuvant cancer treatment. The novel tumor cell lines of the invention include cell lines designated SH-M-20, SH-M-20-A2, SH-M-21, SH-O-30 and SH-L-40 as detailed hereinbelow, and cell lines derived therefrom that may stably express additional exogenous HLA alleles and/or co-stimulatory surface molecules, as described herein. Advantageously, the tumor cell lines of the invention may further express HLA-B35, HLA-A2 and/or 4-1 BB ligand (4-1BBL).

In one embodiment there is provided a melanoma cell line expressing HLA antigens A24, A33, B35, B49, CW04/12 and the tumor associated antigens GD3, S-100, HMB45, Melan A/MART-I, HMW, MSCA, CD146, MAGE-A1 and MAGE-A3 said cell line designated SH-M-20 and deposited under the accession number 11052602. In another embodiment, said cell line further expresses (e.g. exogenously) the HLA-A2 antigen. In a particular embodiment, said cell line further expressing the HLA-A2 antigen is designated SH-M-20-A2 and deposited under the accession number 11052604. In another embodiment said cell line further expresses (e.g. exogenously) 4-1BBL.

In another embodiment there is provided a melanoma cell line expressing HLA antigens A2/24, B35 and the tumor associated antigens S-100, GD3, MAGE-A1, MAGE-A3 and NY-ESO, said cell line designated SH-M-21 and deposited under the accession number 11052601. In another embodiment said cell line further expresses 4-1BBL.

In another embodiment there is provided a carcinoma cell line expressing HLA alleles A26, A28, B14, B35, DRB01, DRB104 and the tumor associated antigens CEA, MAGE, and MUC-1, said cell line designated SH-L-40 and deposited under the accession number 11052605. In another embodiment, said cell line further expresses the HLA-A2 antigen. In another embodiment said cell line further expresses 4-1BBL.

In another embodiment the invention provides an ovary carcinoma cell line expressing HLA antigens A03/25, B08/18, DRB1 and the tumor associated antigens CEA Ca-125-sec and CEA-sec, said cell line designated SH-O-30 and deposited under the accession number 11052603. In another embodiment, said cell line further expresses the HLA-A2 antigen. In another embodiment said cell line further expresses 4-1BBL.

In another embodiment there is provided an immunogenic composition comprising as an active ingredient at least one tumor cell line of the invention, and optionally pharmaceutically acceptable carrier, excipients, adjuvants and/or diluents.

It is to be understood, that the compositions of the invention that are formulated for human cancer therapy, including therapeutic and vaccine compositions, are produced such that the administered cells are irradiated, chemically attenuated or otherwise incapable of proliferating in the body of the human recipient.

In another aspect there is provided a therapeutic composition for treating, preventing, ameliorating, reducing or delaying the onset of a proliferative disease in a mammalian subject, said therapeutic composition comprising one or more cell lines allogeneic to the subject, wherein at least one of said cell lines expresses at least one HLA allele identical to the HLA alleles of said subject, and wherein at least one of said cell lines endogenously or exogenously express the HLA-B35 and HLA-A2 alleles and 4-1BBL, said composition further comprising one or more pharmaceutically acceptable carrier, diluent, excipient, hapten, adjuvant or additive.

The composition may comprise at least two cell lines allogeneic to said subject. Optionally, at least one of said cell lines may expresses at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1. According to particular embodiments, the at least one of said cell lines may be a tumor cell line of the invention as defined herein.

In another aspect there is provided a therapeutic composition for treating, preventing, ameliorating, reducing or delaying the onset of a proliferative disease in a mammalian subject, said therapeutic composition comprising at least two allogeneic cell lines, wherein at least one of said cell lines expresses at least one HLA allele identical to the HLA alleles of said subject, and wherein at least one of said cell lines endogenously or exogenously express the HLA-B35 allele or any other HLA A or B allele that correlates with improved disease outcome, said composition further comprising a pharmaceutically acceptable carrier, diluent, excipient, hapten, adjuvant or additive.

The methods of the invention advantageously utilize tumor cell lines expressing at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1.

In one embodiment said cell line expresses the HLA antigens A24, A33, B35, B49, CW04/12 and the tumor associated antigens GD3, S-100, gp 100, Melan A/MART-1, HMW, MSCA, CD146, MAGE-A1 and MAGE-A3. In a particular embodiment, said cell line is a melanoma cell line designated SH-M-20 and deposited under the accession number 11052602. In another embodiment, said cell line further expresses the HLA-A2 antigen. In a particular embodiment, said cell line is a melanoma cell line designated SH-M-20-A2 and deposited under the accession number 11052604.

In another embodiment, said cell line expresses the HLA antigen A2/24, B35 and the tumor associated antigens S-100, GD3, MAGE-A1, MAGE-A3 and NY-ESO. In a particular embodiment, said cell line is a melanoma cell line designated SH-M-21 and deposited under the accession number 11052601.

In another embodiment, said cell line expresses the HLA antigens A26, A28, B14, B35, DRB01, DRB104 and the tumor associated antigens, PAN cytokeratin, CEA, MAGE, and MUC-1. In a particular embodiment, said cell line is a lung metastasis carcinoma cell line designated SH-L-40 and deposited under the accession number 11052605.

In another embodiment, said cell line expresses the HLA antigens A03/25, B08/18, DRB1 and the tumor associated antigens CEA Ca-125-sec and CEA-sec. In a particular embodiment said cell line is an ovary carcinoma cell line designated SH-O-30 and deposited under the accession number 11052603.

The therapeutic compositions according to the invention may further comprise an additional therapeutic agent.

According to certain other aspects, the invention relates to a method of treating cancer, said method comprising administering to a subject in need thereof an immunogenic (or therapeutic) composition of the invention, thereby treating cancer in the subject. According to certain other aspects, the invention relates to a method of enhancing an immune response to a tumor in a subject in need thereof, said method comprising administering to the subject an immunogenic (or therapeutic) composition of the invention, thereby enhancing the immune response in said subject.

In some embodiments, the cancer may be a carcinoma, e.g. a metastatic carcinoma including, but not limited to melanoma, ovarian carcinoma and lung carcinoma.

In another embodiment the one or more cell lines express at least one HLA allele identical to the HLA alleles of the subject in need. In another embodiment the one or more cell lines express at least one HLA allele that is not identical to the HLA alleles of the subject in need. In another embodiment the one or more cell lines endogenously or exogenously express the HLA-B35 allele. In another embodiment the one or more cell lines express at least one HLA allele identical to the HLA alleles of the subject in need, and endogenously or exogenously express the HLA-B35 allele. In another embodiment the one or more cell lines endogenously or exogenously express the HLA-B35 and A2 alleles. In another embodiment said one or more cell lines endogenously or exogenously express 4-1 BB ligand (4-1BBL). According to particular embodiments, the method comprises administering to said subject at least one of cell lines of the invention as defined herein. In another embodiment, the method comprises administering to said subject a therapeutic composition of the invention as defined herein. In another embodiment said cell lines further expresses at least one tumor antigen or any peptides or fragments thereof. In another embodiment at least one of said cell lines optionally endogenously or exogenously expresses a co-stimulatory or otherwise enhancing molecule.

In another aspect the invention provides a method for treating, preventing, ameliorating, reducing or delaying the onset of a proliferative disease in a mammalian subject, wherein said method comprise the step of administering to said subject a therapeutically effective amount of at least two allogeneic cell lines, or of any composition comprising the same, wherein at least one of said cell lines expressed at least one HLA allele identical to the HLA alleles of said subject and wherein at least one of said cell lines endogenously or exogenously express the HLA-B35 allele or any other HLA A or B allele that correlates with improved disease outcome.

In one embodiment said proliferative disorder is a malignant disorder, said disorder is any one of melanoma, carcinoma, leukemia, sarcoma, myeloma and lymphoma. In a particular embodiment said malignant disorder is melanoma.

In another embodiment said method leads to an increase of at least one of the OS (overall survival) and DFS (disease free survival) of said subject. In another embodiment said method leads to the activation of CD8-mediated cytotoxic response against said proliferative disorder in said subject.

In another embodiment said at least one of said cell lines express at least one HLA antigens and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1.

In another embodiment said cell line expresses the HLA antigens A24, A33, B35, B49, CW04/12 and the tumor associated antigens GD3, S-100, HMB45, Melan A/MART-I, HMW, MSCA, CD146, MAGE-A1 and MAGE-A3. In a particular embodiment said cell line is a melanoma cell line designated SH-M-20. In another embodiment said cell line further expresses the HLA-A2. In a particular embodiment said cell line is a melanoma cell line designated SH-M-20-A2.

In another embodiment, said cell line expresses the HLA antigen A2/24, B35 and the tumor associated antigens S-100, GD3, MAGE-A1, MAGE-A3 and NY-ESO. In a particular embodiment, said cell line is a melanoma cell line designated SH-M-21 and deposited under the accession number 11052601.

In another embodiment, said cell line expresses the HLA antigens A26, A28, B14, B35, DRB01, DRB104 and the tumor associated antigens, PAN cytokeratin, CEA, MAGE, and MUC-1. In a particular embodiment, said cell line is a lung metastasis carcinoma cell line designated SH-L-40 and deposited under the accession number 11052605.

In another embodiment, said cell line expresses the HLA antigens A03/25, B08/18, DRB1 and the tumor associated antigens CEA Ca-125-sec and CEA-sec. In a particular embodiment said cell line is an ovary carcinoma cell line designated SH-O-30 and deposited under the accession number 11052603.

In another embodiment said subject expresses the B35 HLA allele. In another embodiment the method further comprises the step of assessing the presence of the B35 HLA phenotype in the subject, and if said subject displays the B35 HLA phenotype, administering said composition to said subject.

In another aspect the invention relates to a combination of at least two allogeneic cell lines for use in treating, preventing, ameliorating, reducing or delaying the onset of proliferative diseases in a subject in need thereof, wherein at least one of said cell lines endogenously or exogenously express the HLA B35 allele, and wherein at least one of said cell lines expressed at least one HLA allele identical to the HLA alleles of said subject. In some embodiments, said cell lines are tumor cell lines of the invention as defined herein.

Other objects, features and advantages of the present invention will become clear from the following description and drawings.

BRIEF DESCRIPTION OF THE DRAWINGS

FIG. 1A: correlation of overall survival and HLA-B35. FIG. 1B: correlation of disease free survival and HLA-B35. FIG. 1C: correlation of OS and HLA-B07. Full line: patients not expressing the allele; dotted line: patients expressing the allele.

FIG. 2 shows staining of the SH-M-20 cell line for the indicated different melanoma associated antigens, using the alkaline phosphatase anti alkaline phosphatase (APAAP) reaction. Brown/gray (if submitted black and white) color indicate positive staining.

FIG. 3A: FACS analysis of High Molecular Weight Melanoma Associated Antigen (histogram I) and HLA-A, B, C (histogram II) expression. Filled histogram is secondary antibody (Ab) only. FIG. 3B: FACS analysis of Melanoma Cell Surface Antigen (MCSA, histogram I) and CD146 (histogram II) expression on SH-M-20 melanoma. Histogram III is secondary Ab only.

FIG. 12A-SH-O-30.10 derived lines. FIG. 12B-SH-L-40 derived lines.

DETAILED DESCRIPTION OF THE INVENTION

Figure 1A:
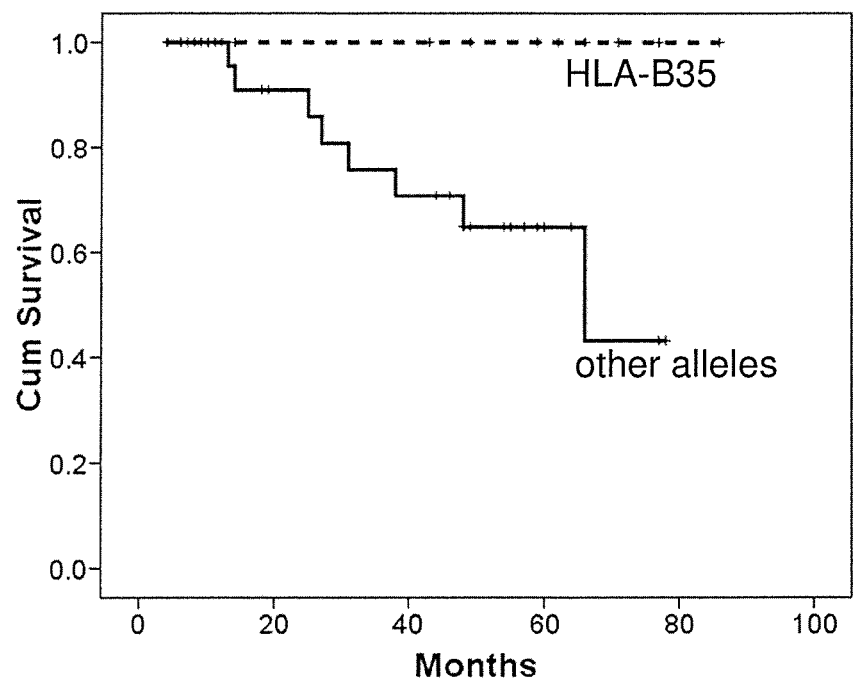
FIGS. 1A-1C: Correlation of HLA phenotype and disease outcome.

The present invention relates to cancer immunotherapy, specifically to allogeneic tumor cell vaccines. The present invention discloses the survival data of forty two melanoma patients at high risk for disease recurrence who received an allogeneic vaccine composed of a combination of three melanoma cell lines, each matching at least one allele of the recipient's HLA-A and -B loci. The partial HLA class I matching may direct activation of T cells by the vaccine, without the need for antigen presenting cell mediation.

The present invention shows a significant correlation between the B35 phenotype and improved survival of melanoma patients.

It is therefore an object of the present invention to provide allogeneic vaccination comprising a combination of allogeneic cell line expressing the HLA-B35 phenotype for the adjuvant treatment of proliferative disorders, specifically, metastatic cancer.

It is a further object of the present invention to provide a partially HLA-matched allogeneic melanoma vaccine for the adjuvant treatment of high risk melanoma patients.

A further object of the present invention is to provide an improved immunotherapy treatment for metastatic melanoma patients.

Yet another object of the invention is to provide a partially HLA-matched allogeneic epithelial cell vaccine for the adjuvant treatment of high risk carcinoma patients providing an improved immunotherapy treatment for metastatic carcinoma patients, specifically, lung and ovary carcinoma.

It was previously shown that an adjuvant autologous cell vaccine is associated with improved survival in high-risk melanoma patients who develop strong delayed type hypersensitivity (DTH) response to unmodified melanoma cells (Lotem et al., 2002). The present invention provides according to some embodiments a vaccine comprising of tumor cell lines which is administered to subjects with unavailable autologous tumor, by the use of HLA-matched melanoma cell lines. Embodiments of the present invention relate to a vaccine comprising three cell lines, each matching the recipient's HLA-A and -B loci, with at least one identical allele. Without wishing to be bound by a theory or mechanism of action, the partial HLA class I matching may allow direct activation of T cells by the vaccine, without the need for antigen presenting cell mediation.

HLA-B35 is one of the largest B serotype groups; it currently has 97 known nucleotide variants and 86 polypeptide isoforms. HLA-B35 is present in 10-40% of Caucasoid populations and 30% of Israeli Jews (http://www.allelefrequencies.net). The B35 phenotype is correlated with expression of certain specific TAA epitopes, including those derived from gp100, tyrosinase, MAGE-3, NY-ESO-1, cytochrome P450 1B1 and survivin (Vigneron et al., 2005; Morel et al., 1999; Schultz et al., 2001; Bioley et al., 2009; Kvistborg et al., 2008; Reker et al., 2004).

Noteworthy, it was previously shown that melanoma patients expressing the HLA B35 phenotype had a poor survival outcome following mismatched allogeneic vaccination (Hoon et al., 1998).

As indicate above, in contrast to the prior publication, the inventors surprisingly found a correlation between a favorable disease outcome and the B35 HLA phenotype. This advantage was not due to one particularly immunogenic donor line, as patients were vaccinated with different cell lines with the B35 phenotype (Table 5). The correlation between the B35 phenotype and improved survival described in this invention, in the context of the correlation between this phenotype and cytotoxic responses against melanoma, enhances the critical role of CD8-mediated cytotoxicity in the outcome of melanoma.

The invention provides novel cell lines useful as therapeutic cell vaccine compositions. The invention further provides advantageous screening methods and means for identifying patients amenable for treatment with partially Human Leukocyte Antigen (HLA) matched allogeneic cell vaccines. Therapeutic compositions and methods for use in proliferative disorders are further provided.

These and other objects of the invention will become apparent as the description proceeds.

Definitions

The "Human Leukocyte Antigen" or "HLA" represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC.

HLA antigens (HLA molecules) corresponding to MHC class I (A, B and C) present peptides from inside the cell (including viral peptides if present). These peptides are produced from digested proteins that are broken down in the proteasomes. The peptides are generally small polymers, about 9 amino acids in length. HLA class I molecules are recognized by CD8 T-cells, which are the principal effector cells of the adaptive immune response.

HLA antigens corresponding to MHC class II (DP, DM, DOA, DOB, DQ and DR) present antigens from outside of the cell to T-lymphocytes. These particular antigens stimulate T-helper cells to multiply, and these T-helper cells then stimulate antibody-producing B-cells to produce antibodies to that specific antigen. Self-antigens are suppressed by suppressor T-cells.

MHC class II molecules are HLA-DP, HLA-DM, HLA-DOA, HLA-DOB, HLA-DQ and HLA-DR, and are mainly expressed on the surface of antigen presenting cells (APCs), the most important of which appears to be the dendritic cells. APCs stimulate naïve T-cells, as well as other cells in the immune system. Specifically, they stimulate both CD8 T-cells and CD4 T-cells.

HLA antigens corresponding to MHC class III encode components of the complement system.

Sequences for MHC class I antigens, including, but not limited to HLA-A2 and HLA-B35, are known in the art, and may be found in publicly available databases, such as NCBI, e.g. at: http://www.ncbi.nlm.nih.gov/entrez/viewer.fcgi?db=nucleotide&val=375 18361.

As used herein the term "endogenously" means that the specific HLA antigen or any enhancing molecule has been produced or synthesized from within an organism or a tissue or a cell. The term "exogenously" means that this antigen or enhancing molecule has been introduced from outside of the cell or tissue. More specifically, the specific HLA antigen may have been introduced to the cells by a transfection, specifically, a stable transfection.

The term "transfection" as used herein refers to the introduction of a transgene into a cell. The term "transgene" as used herein refers to any nucleic acid sequence which is introduced into the genome of a cell by experimental manipulations. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, retroviral infection, biolistics (i.e., particle bombardment) and the like. According to certain embodiments, viral vectors (e.g. retroviral vectors) may be used for stably transfecting e.g. an HLA or co-stimulatory molecule into epithelial carcinoma cells of the invention.

The term "stable transfection" refers to the introduction and integration of a transgene into the genome of the transfected cell. Transient transfection refers to the introduction of one or more transgenes into a transfected cell in the absence of integration of the transgene into the host cell's genome. A cell stably expresses an endogenous gene product, or an exogenous gene product as a result of stable transfection of the corresponding nucleic acid sequence encoding the product.

In the context of the present invention the term "allogeneic" means that the tumor cells are derived from an individual who is different from the individual to whom the cell lines according to the present invention shall be later administered.

More specifically, in the context of the present invention the term "allogeneic cell lines" further comprises cell lines, including e.g., tumor cell lines, or cell lines or cultures from primary material and the like, which are not originating from the individual to which the cells shall be administered.

The term "tumor-associated antigen" refers to any protein, peptide or antigen associated with (carried by, expressed by, produced by, secreted by, etc) a tumor or tumor cell(s). Tumor-associated antigens may be (nearly) exclusively associated with a tumor or tumor cell(s) and not with healthy normal cells or may be over expressed (e.g., 2 times, 5 times, 10 times, 50 times, 100 times, 1000 times or more) in a tumor tissue or tumor cell(s) compared to healthy normal tissue or cells. More particularly, a tumor-associated antigen is an antigen capable of being presented (in processed form) by MHC determinants of the tumor cell. Hence, tumor-associated antigens are likely to be associated only with tumors or tumor cells expressing MHC molecules.

The composition of the present invention is intended for the treatment of a proliferative disorder, specifically, a malignant disorder. As used herein to describe the present invention, "proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the compositions and methods of the present invention may be used in the treatment of non-solid and solid tumors.

The term "cancer" or "cancer cell" is used herein to denote a tissue or cell found in a neoplasm which possesses characteristics which differentiate it from normal tissue or tissue cells.

Overall survival (OS) as used herein is defined as the percentage of patients who survived at a given time after surgery to remove their tumor. In this case, the Kaplan-Meier curve simply represents the x % of patients survived after y amount of time.

Disease-free survival (DFS) is defined as the percentage of patients staying free of disease at a given time after surgery to remove their tumor. In this case, the Kaplan-Meier curve simply represents the x % of free of disease patients surviving after y amount of time.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

"Administering" means the actual physical introduction of the composition into or onto (as appropriate) the host. Any and all methods of introducing the composition into the host are contemplated according to the invention; the method is not dependent on any particular means of introduction and is not to be so construed. Means of introduction are well-known to those skilled in the art, and also are exemplified herein.

By "cell lines derived therefrom" is meant "variants" or "sub-clones" of the cell line. A "variant" of such cell line is meant to refer to a naturally occurring cell line by different passages or different treatments. These variants and sub-clones are functionally similar to the original cell line.

By "functionally similar" is meant having same biological function, for example, having identical ability to induce an immune response directed against malignancy, and expressing essentially the same tumor specific antigens.

Diagnostic and Prognostic Assays

The invention relates in some embodiments to methods for assessing or evaluating the prognosis of a subject afflicted with cancer following allogeneic tumor cell vaccination, and of identifying subjects amenable for treatment with allogeneic tumor cell vaccination. The methods according to this aspect comprise assessing the presence of the B35 HLA phenotype in the subject, wherein the presence of the B35 HLA phenotype indicates a favorable disease outcome following allogeneic tumor cell vaccination.

According to some embodiments there is provided a method for predicting the likelihood a subject will respond therapeutically to a method of treating cancer comprising administering a therapeutic composition comprising as an active ingredient one or more allogeneic cell lines, wherein the method for predicting comprises determining the expression of the B35 HLA allele in said subject, wherein expression of the B35 HLA allele in said subject indicates an increased likelihood said subject will respond therapeutically to said method of treating cancer.

The invention is further directed to an in vitro method for predicting the likelihood a subject will respond therapeutically to a method of treating cancer comprising immunization with allogeneic tumor cells, which method for predicting comprises: determining the presence of the B35 Human Leukocyte Antigen (HLA) allele in a biological sample of said subject, wherein the presence of the B35 HLA allele indicates an increased likelihood said subject will respond therapeutically to the method of treating cancer.

In other embodiments, there is provided a method for identifying a subject that will respond therapeutically to a method of treating cancer comprising administering a therapeutic composition comprising as an active ingredient one or more allogeneic cell lines, wherein the method for identifying comprises determining the presence of the B35 HLA allele in said subject (e.g. in a biological sample of said subject), wherein the presence of the B35 HLA allele in said subject indicates that said subject will respond therapeutically to the method of treating cancer.

In another embodiment, the invention provides a method for selecting a cancer therapy, comprising determining in vitro the presence of HLA B35 in a sample (e.g. a cell-containing fluid sample obtained non-invasively), and if the sample comprises HLA B35, selecting a cancer therapy comprising immunization with a partially HLA matched tumor cell vaccine.

In another embodiment, there is provided a method for treating, preventing, ameliorating, reducing or delaying the onset of a proliferative disease in a mammalian subject, comprising:

a) assessing the presence of the B35 HLA phenotype in the subject, and b) if said subject displays the B35 HLA phenotype, administering to said subject one or more allogeneic cell lines or a composition comprising same, thereby preventing, ameliorating, reducing or delaying the onset of a proliferative disease in said subject.

According to some embodiments, the subject is afflicted with cancer such as a carcinoma, e.g. metastatic carcinomas including but not limited to melanoma, ovarian carcinoma, colon carcinoma and lung carcinoma, wherein each possibility represents a separate embodiment of the invention. In a particular embodiment, the subject is afflicted with melanoma.

In one embodiment, the method of treating cancer, cancer therapy, immunization or allogeneic tumor cell vaccination comprises administering to said subject a partially HLA-matched allogeneic epithelial cell vaccine. In a particular embodiment, the vaccine is a partially HLA-matched allogeneic melanoma vaccine. In another particular embodiment, the vaccine is a partially HLA-matched metastatic carcinoma vaccine, e.g. lung or ovary carcinoma. In another embodiment, the method of treating cancer, cancer therapy, immunization or allogeneic tumor cell vaccination comprises administering to said subject one or more allogeneic cell lines. In another embodiment, the method of treating cancer, cancer therapy, immunization or allogeneic tumor cell vaccination comprises administering to said subject a therapeutic composition comprising as an active ingredient at least two allogeneic cell lines, wherein at least one of the cell lines expresses at least one HLA allele identical to the HLA alleles of the subject in need, and at least one of said cell lines endogenously or exogenously express the HLA-B35 allele or any other HLA A or B allele that correlates with improved disease outcome and optionally a pharmaceutically acceptable carrier, diluent, excipient, hapten, adjuvant or additive.

In another embodiment, the one or more cell lines (e.g. the at least two cell lines) express at least one HLA allele identical to the HLA alleles of the subject in need. In another embodiment the one or more cell lines express at least one HLA allele that is not identical to the HLA alleles of the subject in need. In another embodiment the one or more cell lines endogenously or exogenously express the HLA-B35 allele. In another embodiment the one or more cell lines express at least one HLA allele identical to the HLA alleles of the subject in need, and endogenously or exogenously express the HLA-B35 allele. In another embodiment the one or more cell lines endogenously or exogenously express the HLA-B35 and A2 alleles. In an additional embodiment said one or more cell lines endogenously or exogenously express 4-1 BB ligand (4-1BBL). In another embodiment, said one or more cell lines are selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, as defined herein, wherein each possibility represents a separate embodiment of the invention. It is to be understood, that the administered cells are irradiated, chemically attenuated or otherwise incapable of proliferating in the body of the human recipient.

In another embodiment, the method further comprises administering to said subject a therapeutic composition of the invention. In one embodiment the method comprises administering to said subject a therapeutic composition comprising as an active ingredient at least two allogeneic cell lines, wherein at least one of the cell lines expresses at least one HLA allele identical to the HLA alleles of the subject in need, and at least one of said cell lines endogenously or exogenously express the HLA-B35 allele or any other HLA A or B allele that correlates with improved disease outcome and optionally a pharmaceutically acceptable carrier, diluent, excipient, hapten, adjuvant or additive.

In another embodiment, the one or more cell lines (e.g. the at least two cell lines) express at least one HLA allele identical to the HLA alleles of the subject in need. In another embodiment the one or more cell lines express at least one HLA allele that is not identical to the HLA alleles of the subject in need. In another embodiment the one or more cell lines endogenously or exogenously express the HLA-B35 allele. In another embodiment the one or more cell lines express at least one HLA allele identical to the HLA alleles of the subject in need, and endogenously or exogenously express the HLA-B35 allele. In another embodiment the one or more cell lines endogenously or exogenously express the HLA-B35 and A2 alleles. In an additional embodiment said one or more cell lines endogenously or exogenously express 4-1 BB ligand (4-1BBL). In another embodiment, said one or more cell lines are selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, as defined herein, wherein each possibility represents a separate embodiment of the invention. It is to be understood, that the administered cells are irradiated, chemically attenuated or otherwise incapable of proliferating in the body of the human recipient.

In another embodiment, said cell line(s) further expresses at least one tumor antigen or any peptides or fragments thereof. In another embodiment, at least one of said cell lines optionally endogenously or exogenously expresses a co-stimulatory or otherwise enhancing molecule.

Assessing or determining the presence or expression of the B35 HLA phenotype or allele collectively relate to examining HLA types, which may be effected by a variety of methods well known in the art. A genetic allele can be detected by direct detection of regions/nucleotides within the allele using genomic DNAs prepared from biosamples, e.g., blood, saliva, urine or hair. The allele or its product can also be detected by, for example, serological or microcytotoxicity methods. It also can be determined by detecting an equivalent genetic marker of the allele, which can be, e.g., an SNP (single nucleotide polymorphism), a microsatellite marker or other kinds of genetic polymorphisms.

The presence of a genetic marker (e.g., an HLA allele) can be determined by direct detection of that marker or particular regions within it. Genomic DNAs for allele detection can be prepared from a patient by methods well known in the art, e.g., PUREGENE DNA purification system from Gentra Systems, Minn. Detection of a region within a genetic marker of interest includes examining the nucleotide(s) located at either the sense or the anti-sense strand within that region. Methods known in the art can be used to detect a particular region, e.g., Sequence specific oligonucleotides-hybridization, Real-time PCR, or CSSO-ELISA (M. Hiratsuka et al, J. of Biochemical and Biophysic. Methods, 67:87-94, 2006). For example, DNA typing for HLA may be performed by reverse polymerase chain reaction with sequence-specific oligo probe (reverse PCR-SSOP).

There are two parallel systems of nomenclature that are applied to HLA. The, first, and oldest system is based on serological (antibody based) recognition. In this system, antigens were eventually assigned letters and numbers (e.g., HLA-B35 or, shortened, B35). A parallel system that allowed more refined definition of alleles was developed. In this system, a "HLA" is used in conjunction with a letter * and four-or-more-digit number (e.g., HLA-B*08:01, A*68:01, A*24:02:01N N=Null) to designate a specific allele at a given HLA locus. In a particular embodiment, HLA-B35 as used herein may refer to HLA-B*3501.

HLA typing (e.g. serotyping) may be performed on blood or sera samples diluted to optimal sensitivity and used to type cells using specific antibodies. HLA cellular typing may be performed e.g. by the mixed lymphocyte culture (MLC) assay, and is used to determine the HLA class II types. Gene sequencing methods known in the art may also be used to determine the presence of HLA alleles in genomic DNA. Phenotyping or gene typing is different from gene sequencing and serotyping. With this strategy, PCR primers specific to a variant region of DNA are used (called SSP-PCR), a product of the appropriate size indicates that the HLA allele has been identified. For example, SSP-PCR within the clinical situation is often used for identifying HLA phenotypes.

Suitable assays, probes, PCR primers and antibodies for determining HLA types are commercially available, and may also readily designed and manufactured by a skilled artisan, particularly in view of the sequences of the corresponding HLA alleles, gene products and genomic regions provided herein.

Suitable samples for use in the methods of the invention may be obtained from a variety of sources. These samples may be diluted or purified as necessary for the particular assay used. Conveniently, the samples may be obtained by non-invasive methods. For example, suitable DNA samples may be obtained from peripheral blood, saliva, urine, or hair of the patient. Other suitable samples for assessing the presence or expression of HLA alleles are RNA samples, protein samples, cell samples, or serum samples. As used herein a "sample of a subject" refers to a suitable biological sample useful for determining the HLA types of the subject as described herein.

The term "treating" concerns improvement of at least one undesired manifestation of the disease such as: increase in disease free periods, decrease in acute disease periods (in time and severely), decrease in severity of the disease, improvement in life quality, decreased mortality, decrease in the rate of disease progression as well as prophylactic treatment before disease occurs. Accordingly, a favorable disease outcome (or a subject responding therapeutically to a treatment) refers to the outcome of a treatment resulting in an improvement of at least one undesired manifestation of the disease as described above. Improvement refers to a clinically recognized improvement, which may be statistically significant and/or recognized by a person of skill in the art (e.g. physician).

In another aspect there is provided a method for predicting a favorable disease outcome following an allogeneic tumor cell vaccination, which method for predicting comprises assessing the presence of the B35 Human Leukocyte Antigen (HLA) phenotype in a sample of the subject, wherein the presence of the B35 HLA phenotype indicates a favorable disease outcome following vaccination.

In one embodiment said subject is afflicted with melanoma. In another embodiment tumor cell vaccination comprises administering to said subject one or more cell lines endogenously or exogenously expressing the HLA-B35 allele.

In another aspect there is provided a method for identifying a subject that will respond therapeutically to a method of treating cancer comprising administering one or more tumor cell lines allogeneic to the subject, which method for identifying comprises: determining the expression of the B35 HLA allele in a sample obtained from said subject, wherein expression of the B35 HLA allele indicates that said subject will respond therapeutically to the method of treating cancer.

In one embodiment said subject is afflicted with melanoma.

In another embodiment the one or more cell lines express at least one HLA allele identical to the HLA alleles of said subject. In another embodiment the one or more cell lines express at least one HLA allele that is not identical to the HLA alleles of said subject.

In another embodiment the one or more cell lines endogenously or exogenously express the HLA-B35 allele. In another embodiment the one or more cell lines endogenously or exogenously express the HLA-B35 and A2 alleles. In another embodiment said one or more cell lines endogenously or exogenously express 4-1 BB ligand (4-1BBL).

In another embodiment the one or more cell lines is a tumor cell line selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention. In another embodiment the tumor cell line stably expresses an additional exogenous Human Leukocyte Antigen (HLA) and/or co-stimulatory molecule for T cells. In another embodiment the tumor cell line stably expresses at least one of HLA-B35, HLA-A2 and 4-1 BB ligand (4-1BBL), wherein each possibility represents a separate embodiment of the invention.

In another embodiment the invention provides a method of treating cancer in a subject in need thereof, comprising identifying the subject that will respond therapeutically to the method of treating cancer by determining the expression of the B35 HLA allele in a sample obtained from said subject, wherein expression of the B35 HLA allele indicates that said subject will respond therapeutically to the method of treating cancer, and administering to said subject an immunogenic composition comprising one or more tumor cell lines allogeneic to said subject. In another embodiment the one or more cell lines is a tumor cell line selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention. In another embodiment the tumor cell line stably expresses an additional exogenous Human Leukocyte Antigen (HLA) and/or co-stimulatory molecule for T cells. In another embodiment the tumor cell line stably expresses at least one of HLA-B35, HLA-A2 and 4-1 BB ligand (4-1BBL), wherein each possibility represents a separate embodiment of the invention.

Cells

As indicated above three melanoma cell lines (SH-M-20, SH-M-20-A2 and SH-M-21), one lung carcinoma cell line (SH-L-40) and one ovary carcinoma cell line (SH-O-30) were deposited in the European Collection of Cell Cultures (ECACC) Health Protection Agency, (Centre for Emergency Preparedness and Response Porton Down, Salisbury, SP4 0JG, United Kingdom), a Depositary Institution according to the provisions of the Budapest Treaty, as described in Table 1, as follows:

TABLE 1

Deposited cell lines

| Cell line | Date of deposit | Deposit Number |
|---|---|---|
| SH-M-20 | 26 May 2011 | 11052602 |
| SH-M-20-A2 | 26 May 2011 | 11052604 |
| SH-M-21 | 26 May 2011 | 11052601 |
| SH-L-40 | 26 May 2011 | 11052605 |
| SH-O-30 | 26 May 2011 | 11052603 |

The deposits are available as required by foreign patent laws in countries wherein counterparts of the subject application, or its progeny, are filed. However, it should be understood that the availability of the deposits does not constitute a license to practice the subject invention in derogation of patent rights granted by a governmental action.

Further, the cell line deposits were stored and made available to the public in accord with the provisions of the Budapest Treaty for the Deposit of Microorganisms, i.e., they were stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

The invention provides, in another aspect, a tumor cell line selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention.

In one embodiment the tumor cell line stably expresses an additional exogenous Human Leukocyte Antigen (HLA) and/or co-stimulatory molecule for T cells. In another embodiment said tumor cell line expresses at least one of HLA-B35, HLA-A2 and 4-1 BB ligand (4-1BBL), wherein each possibility represents a separate embodiment of the invention. In one embodiment the cells stably express at least one of HLA-B35 and HLA-A2. In another embodiment the cells stably express 4-1BBL and at least one of HLA-B35 and HLA-A2. For example, cells described herein may express HLA-B*35:01, HLA-A*02:01 and 4-1BBL.

According to some embodiments, the use of cell lines of the invention is preferred over other cell lines as they exhibit enhanced immunogenicity, patient compatibility and/or therapeutic efficacy.

The present invention further provides melanoma cell lines expressing different HLA antigens as well as different tumor associated antigens. These cell lines include cell lines designated SH-M-20, SH-M-20-A2 and SH-M-21 that are deposited under the accession numbers 11052602, 11052604 and 11052601 respectively, and cells derived therefrom.

In certain embodiments, the use of SH-M-20 and cells derived therefrom such as SH-M-20-A2 is preferred, as they display enhanced immunogenicity compared to other melanoma cell lines. For example, SH-M-20 was found to be more immunogenic than SH-M-21.

The present invention further provides a lung carcinoma cell line expressing different HLA antigens and tumor associated antigens. A particular embodiment of such cell line is the cell line designated SH-L-40 and deposited under the accession number 11052605.

The SH-L-40 deposited under the accession number 11052605 was further characterized as a carcinoma cell line established from lung metastasis of gastric/colon origin.

The present invention further provides an ovary carcinoma cell line expressing different HLA antigens and tumor associated antigens. A particular embodiment of such cell line is the cell line designated SH-O-30 and deposited under the accession number 11052603.

These cells may further express an additional exogenous Human Leukocyte Antigen (HLA) and/or co-stimulatory molecules.

In one embodiment, the cells stably express HLA-B35.

In another embodiment, the cells stably express HLA-A2.

The term "HLA-B35" may refer to any gene product, defined as HLA-B35 in the 14$^{th}$ International HLA & Immunogenetics Workshop, 2005. The following B-35 alleles are known: B*35:01, B*35:02, B*35:03, B*35:04, B*35:05 (B35-G), B*35:06 (B35-K), B*35:07, B*35:08, B*35:25, B*35:28, B*35:29 (B*KG), B*35:30, B*35:32 (B*TMUL) and B*35:36. The most common allele is the B*35:01 allele, and thus most subjects identified as having HLA-B35 bear the B*35:01 allele.

The term "HLA-A2" may refer to any gene product, defined as HLA-A2 in the 14$^{th}$ International HLA & Immunogenetics Workshop, 2005. The following A-2 alleles are known: A*02:01, A*02:02, A*02:03, A*02:04, A*02:05, A*02:06 (A2.4A), A*02:07, A*02:08, A*02:09, A*02:10, A*02:11 (A2.5), A*02:12, A*02:13 (A*02SLU), A*02:16, A*02:17, A*02:18 (A2K), A*02:19, A*02:20, A*02:21, A*02:31, A*02:34 (A*AAT), A*02:35, A*02:36 and A*02:37. The most common allele is the A*02:01 allele, and thus most subjects identified as having HLA-A2 bear the A*02:01allele.

Thus, cells of the invention which may be used in the compositions and methods described herein may optionally express HLA-B*3501 and/or HLA-A*0201.

A number of molecules have been identified which function to further enhance and extend the activation of T cells. Costimulatory molecules (or co-stimulatory molecules for T cells) including CD28:B7, 4-1BBL, CD40, OX40L and CD70 were identified as being capable in conjunction with the TCR:MHC:Ag stimulus to induce high levels of IL-2 production from T cells. 4-1 BB:4-1BBL are members of the TNF-TNF ligand family, which are expressed on T cells and antigen-presenting cells (APCs), respectively.

The human homologue of 4-1BB (CD137, also designated Tumor necrosis factor ligand superfamily member 9) resides on chromosome 1p36 and contains about 255 amino acids (aa) with two potential N-linked glycosylation sites (Cheuk et al., Cancer Gene Therapy (2004) 11, 215-226). Therapies utilizing the 4-1 BB:4-1BBL signaling pathway have been examined in a number of model systems. Antitumor potential of 4-1BBL was demonstrated in certain systems, particularly in combination with other co-stimulatory molecules such as B7-1 and/or B7-2 (Cheuk et al., 2004).

According to certain embodiments of the present invention 41-BBL was found to have therapeutic advantages in the context of the specific compositions and methods of the invention, as it was found to enhance the immunogenicity of transfected cells expressing HLA-B35 and HLA-A2 to specifically activate their respective T cells, while other co-stimulatory molecules such as CD40 variants did not.

Thus, cells of the invention may optionally express HLA-B*3501, HLA-A*0201 and 41-BBL.

In another embodiment, there is provided a method of producing an immunogenic tumor cell line useful in the preparation of a tumor cell vaccine, the method comprising transfecting the cell with at least one of HLA-B35, HLA-A2 and 41-BBL so as to produce an immunogenic tumor cell line stably expressing HLA-B35, HLA-A2 and 41-BBL.

The cells of the invention may be engineered to express exogenous sequences such as HLA-B35, HLA-A2 and 41-BBL by a variety of transfection methods known in the art. Exemplary methods for producing such cells are provided in the Examples section below. According to particular embodiments as described in the Examples, viral vectors, particularly vectors comprising retroviral long terminal repeats (LTR), were found to be particularly effective in producing epithelial cell lines stably expressing HLA antigens such as HLA-A2.

There is provided a melanoma cell line expressing HLA antigens A24, A33, B35, B49, CW04/12 and the tumor associated antigens GD3, S-100, HMB45, Melan A/MART-I, HMW, MSCA, CD146, MAGE-A1 and MAGE-A3 said cell line designated SH-M-20 and deposited under the accession number 11052602. The cell line may further express the HLA-A2 antigen, said cell line designated SH-M-20-A2 and deposited under the accession number 11052604.

There is provided a melanoma cell line expressing HLA antigens A2/24, B35 and the tumor associated antigens S-100, GD3, MAGE-A1, MAGE-A3 and NY-ESO said cell line designated SH-M-21 and deposited under the accession number 11052601.

There is provided a carcinoma cell line expressing HLA alleles A26, A28, B14, B35, DRB01, DRB104 and the tumor associated antigens CEA, MAGE, and MUC-1 said cell line designated SH-L-40 and deposited under the accession number 11052605.

There is provided an ovary carcinoma cell line expressing HLA antigens A03/25, B08/18, DRB1 and the tumor associated antigens CEA Ca-125-sec and CEA-sec said cell line designated SH-O-30 and deposited under the accession number 11052603.

There is also provided an immunogenic composition comprising as an active ingredient at least one tumor cell line according to any one of the cell lines described herein.

Expression Vectors and Recombinant Methods

The preparation of expression constructs or vectors used for delivering and expressing a desired gene product are known in the art. An isolated nucleic acid sequence can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis (see e.g. Sambrook et al., 2001, Molecular Cloning: A Laboratory Manual, Cold Springs Harbor Laboratory, New York; Ausubel, et al., 1989, Chapters 2 and 4). Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional gene product.

The construct may also comprise other regulatory sequences or selectable markers, as known in the art. The nucleic acid construct (also referred to herein as an "expression vector") may include additional sequences that render this vector suitable for replication and integration in prokaryotes, eukaryotes, or optionally both (e.g., shuttle vectors). In addition, a typical cloning vector may also contain transcription and translation initiation sequences, transcription and translation terminators, and a polyadenylation signal.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives. These may serve as vector backbone for the constructs useful in embodiments described herein.

Expression vectors containing regulatory elements from eukaryotic viruses such as retroviruses can be also used. SV40 vectors include pSVT7 and pMT2, for instance. Vectors derived from bovine papilloma virus include pBV-1 MTHA, and vectors derived from Epstein-Barr virus include pHEBO and p2O5. Other exemplary vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. These may serve as vector backbone for the constructs of the present invention.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (AcMNPV), as described by Liang, C. Y. et al. (2004). High efficiency gene transfer into mammalian kidney cells using baculovirus vectors. Arch Virol 149, 51-60.

Recombinant viral vectors are useful for in vivo expression of the genes of the present invention since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Retroviral-derived vectors include e.g. lentiviral vectors. "Lentiviral vector" and "recombinant lentiviral vector" are derived from the subset of retroviral vectors known as lentiviruses. Lentiviral vectors refer to a nucleic acid construct which carries, and within certain embodiments, is capable of directing the expression of a nucleic acid molecule of interest. The lentiviral vector includes at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the lentiviral vector used (if these are not already present in the retroviral vector). Optionally, the recombinant lentiviral vector may also include a signal which directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof.

"Lentiviral vector particle" may be utilized within the present invention and refers to a lentivirus which carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope.

Pharmaceutical Compositions

According to further aspects, the invention relates to compositions, particularly cell vaccine and immunogenic whole cell compositions, useful in the treatment of proliferative disorders. The compositions of the inventions comprise at least one cell line (e.g. two or more cell lines) that are allogeneic to the subject to which the composition is to be administered.

Cancer cell vaccine may constitute live (but non-replicating), or killed cancer cells from the individual to be treated or from another cancer entirely. The vaccine also may be a cancer cell extract or purified vaccine preparation derived from cancer cells. Cancer cell vaccines are well known in the art and may be prepared in accordance with well-known methods.

Typically, a composition (e.g. a cancer cell vaccine) of the invention is a whole cell preparation, comprising irradiated or otherwise attenuated (non-replicating) cell lines, or killed tumor cell lines. In addition, the composition typically comprises cell lines which are at least partially HLA matched with the recipient subject. Thus, at least one of the cell lines expresses at least one HLA allele identical to the HLA alleles of the subject in need. In certain embodiments, the composition is a partially HLA matched vaccine, i.e. comprises cell line(s) that express at least one HLA allele identical to the HLA alleles of the subject in need and at least one HLA allele not identical to the HLA alleles of the subject in need. Furthermore, typically and advantageously, at least one of the cell lines in the composition endogenously or exogenously expresses the HLA-B35 allele. According to specific embodiments, at least one of said cell lines may endogenously or exogenously express the HLA-A2 allele and/or 4-1 BB ligand (4-1BBL). For example, the composition may contain cells expressing HLA-B*35:01, HLA-A*02:01 and 4-1BBL. The invention refers in particular to cancer treatment comprising the use of these compositions, and to methods of predicting the efficacy of such cancer treatment comprising correlating the presence of the B35 allele with an enhanced therapeutic efficacy, as detailed herein.

In addition to the active ingredient, e.g. the non-proliferating tumor cell line, the composition of the invention optionally further comprises pharmaceutically acceptable carrier, diluent, excipient, hapten, adjuvant and/or additive.

The compositions of the invention may be used for treating, preventing, ameliorating, reducing or delaying the onset of a proliferative disease in a mammalian subject, wherein each possibility represents a separate embodiment of the invention.

According to one aspect there is provided a therapeutic composition for treating, preventing, ameliorating, reducing or delaying the onset of a proliferative disease in a mammalian subject, said therapeutic composition comprising one or more cell lines allogeneic to the subject, wherein at least one of said cell lines expresses at least one Human Leukocyte Antigen (HLA) allele identical to the HLA alleles of said subject, and wherein at least one of said cell lines endogenously or exogenously express the HLA-B35 and HLA-A2 alleles and 4-1 BB ligand (4-1BBL), said composition further comprising one or more pharmaceutically acceptable carrier, diluent, excipient, hapten, adjuvant or additive.

In one embodiment, said composition comprises at least two cell lines allogeneic to said subject.

In another embodiment said at least one of said cell lines expresses at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1.

In another embodiment, at least one of said cell lines is a tumor cell line is selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention. In another embodiment said tumor cell line stably expresses an additional exogenous Human Leukocyte Antigen (HLA) and/or co-stimulatory molecule for T cells. In another embodiment said tumor cell line expresses at least one of HLA-B35, HLA-A2 and 4-1 BB ligand (4-1BBL), wherein each possibility represents a separate embodiment of the invention.

In another aspect there is provided a composition comprising a melanoma cell line expressing HLA antigens A24, A33, B35, B49, CW04/12 and the tumor associated antigens GD3, S-100, HMB45, Melan A/MART-I, HMW, MSCA, CD146, MAGE-A1 and MAGE-A3 said cell line designated SH-M-20 and deposited under the accession number 11052602. Said cells may further express the HLA-A2 antigen said cell line designated SH-M-20-A2 and deposited under the accession number 11052604.

In another aspect there is provided a composition comprising a melanoma cell line expressing HLA antigens A2/24, B35 and the tumor associated antigens S-100, GD3, MAGE-A1, MAGE-A3 and NY-ESO said cell line designated SH-M-21 and deposited under the accession number 11052601.

In another aspect there is provided a composition comprising a carcinoma cell line expressing HLA alleles A26, A28, B14, B35, DRB01, DRB104 and the tumor associated antigens CEA, MAGE, and MUC-1 said cell line designated SH-L-40 and deposited under the accession number 11052605.

In another aspect there is provided a composition comprising an ovary carcinoma cell line expressing HLA antigens A03/25, B08/18, DRB1 and the tumor associated antigens CEA Ca-125-sec and CEA-sec said cell line designated SH-O-30 and deposited under the accession number 11052603.

Yet another aspect of the present invention relates to a therapeutic composition for treating, preventing, ameliorating, reducing or delaying the onset of a proliferative disease in a mammalian subject. The therapeutic composition according to this aspect comprises as an active ingredient at least one allogeneic cell lines. It should be noted that at least one of the cell lines expresses at least one HLA allele identical to the HLA alleles of the subject in need. Furthermore, at least one of said cell lines endogenously or exogenously express the HLA-B35 allele or any other HLA A or B allele that correlates with improved disease outcome. The composition optionally further comprises pharmaceutically acceptable carrier, diluent, excipient, hapten, adjuvant or additive.

Cancer vaccines are a heterogeneous group of treatments attempting to modulate immune response against neoplastic disorders. The type of peptides, proteins, gangliosides and adjuvants in the vaccine determines the nature of antigen processing, presentation and costimulation, and can change immune response from a tolerogenic effect to immunogenic stimulation. The embodiments described herein provide compositions combining tumor cell lines, specifically melanoma cell lines with compatible HLA class I haplotypes, together with dinitrophenyl (DNP) and the powerful adjuvant Bacille Calmete Guerin (BCG) that act together to generate protective immunity, as reflected in the survival data presented in this invention.

Thus, according to one aspect, the present invention relates to a therapeutic composition for treating, preventing, ameliorating, reducing or delaying the onset of a proliferative disease in a mammalian subject. The therapeutic composition of the invention comprises as an active ingredient at least two allogeneic cell lines. It should be noted that at least one of the cell lines expresses at least one HLA allele identical to the HLA alleles of the subject in need. Furthermore, at least one of the cell lines endogenously or exogenously express the HLA-B35 allele or any other HLA A or B allele that correlates with improved disease outcome. The composition further comprises pharmaceutically acceptable carrier, diluent, excipient, hapten, adjuvant or additive.

The composition according to this aspect comprises as an active ingredient a combination of allogeneic cell lines.

The allogeneic cell line comprised in the composition of the invention express at least one HLA-antigen matching the recipient's HLA-A and B loci, with at least one identical allele. In various embodiments, the cell line has 1, 2, 3, 4, 5 or 6 HLA alleles identical to those of the subject.

As mentioned above, at least one of the allogeneic cell lines used for the composition of the invention may endogenously or exogenously express the HLA-B35 allele or any other HLA A or B allele that correlates with improved disease outcome. It should be noted that in certain embodiments, cell lines expressing (endogenously or exogenously) the HLA-B35 allele may be particularly effective in treating patients expressing a matching HLA-B35 allele. In yet further specific embodiments, such patients may be specifically melanoma patients.

However, it should be noted that in other alternative embodiments, cell lines expressing the matching HLA-B35 allele may be used for treating patient that do not express a matching HLA-B35 allele. In other embodiments, cells expressing said allele may be used for treating patients suffering from any proliferative disease, for example, lung carcinoma or ovary carcinoma.

In yet another embodiment, at least one allogeneic cell line used by the composition of the invention may endogenously or exogenously express any other HLA A or B allele that correlates with improved disease outcome.

It should be noted that in certain embodiments, an improved outcome is meant any increase, elevation, enhancement of at least one of the OS (overall survival) and DFS (disease free survival) of the treated subject.

It should be noted that an improvement may include an increase of about 5%, 10%, 15%, 20%, 25%, 30%, 35%, 40%, 45%, 50%, 55%, 60%, 65%, 70%, 75%, 80%, 85%, 90%, 95% or 99% of at least one of, the OS and DFS of the treated subject as compared to untreated control. It should be further noted that improvement of the outcome may also include, in certain embodiments, a decrease in the mortality or in the tumor progression. The terms decrease, reduction, attenuation, include a decrease of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

According to one embodiment, the composition of the invention may comprise at least two allogeneic cell lines. In certain embodiment the composition may comprise between about 2 to 50 different cell lines more specifically, about 2, 3, 4, 5, 6, 7, 8, 9, 10, 20, 30, 40, 50 different cell lines.

According to another embodiment, the said cell lines comprised within the composition of the invention may further express at least one tumor associated antigen (TAA) or any peptides or fragments thereof. Specifically, the cell lines should express at least one TAA known to be associated with the treated disease for the recognition of the antigens by the cytotoxic T cells.

According to one embodiment, at least one of the cell lines used for the composition of the invention optionally endogenously or exogenously expresses the HLA A2 antigen.

In yet another embodiment, at least one of the cell lines optionally endogenously or exogenously expresses a co-stimulatory or otherwise enhancing molecule. Non-limiting examples for such enhancing molecules may include 4-1BBL, OX40L B7-1, B7-2 (Sharpe et al., 2009).

In one specific embodiment, such proliferative disorder may specifically be a malignant disorder for example; melanoma, carcinoma, leukemia, sarcoma, myeloma and lymphoma, wherein each possibility represent a separate embodiment of the invention. According to additional embodiments of particular interest, the disorder is colon or gastric carcinoma.

More specifically, it should be appreciated that in particular embodiments, the composition of the invention may be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as head and neck tumors, tumors in lip and oral cavity, pharynx, larynx, paranasal sinuses, major salivary glands, thyroid gland, esophagus, stomach, small intestine, colon, colorectum, anal canal, liver, gallbladder, extrahepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma. Each possibility represents a separate embodiment of the invention. It should be recognized that melanoma, lung carcinoma and ovary carcinoma are of specific interest.

In yet another particular embodiment, the composition of the invention is specifically applicable for the treatment of melanoma.

The term melanoma includes, but is not limited to, melanoma, metastatic melanoma, melanoma derived from either melanocytes or melanocyte-related nevus cells, melanocarcinoma, melanoepithelioma, melanosarcoma, melanoma in situ, superficial spreading melanoma, nodular melanoma, lentigo maligna melanoma, acral lentiginoous melanoma, invasive melanoma or familial atypical mole and melanoma (FAM-M) syndrome. Such melanomas may be caused by chromosomal abnormalities, degenerative growth and developmental disorders, mitogenic agents, ultraviolet radiation (UV), viral infections, inappropriate tissue gene expression, alterations in gene expression, or carcinogenic agents. The aforementioned melanomas can be treated by the method and the composition described in the present invention.

It should be appreciated that certain embodiments of the invention involve the use of a composition comprising at least one allogeneic cell line that endogenously or exogenously express the HLA-B35 allele. In particular embodiments, such compositions may be specifically efficient in treating patients expressing a matching HLA-B35 allele. In yet further particular embodiments, such compositions may specifically be used for HLA-B35 allele expressing melanoma patients.

According to other specific embodiments of the invention, the allogeneic cell lines used for treating melanoma patients may include any of the tumor cell lines established by the invention. In particular embodiment, such cell lines may include for example the following melanoma cell lines of the invention: SH-M-20, SH-M-20-A2 or SH-M-21, or any cell line derived therefrom.

In yet another specific embodiment, the composition of the invention may be specifically applicable in the treatment of Lung Carcinoma. According to another embodiment, the composition of the invention may be specifically applicable in the treatment of carcinoma lung metastases.

According to such specific embodiment, the allogeneic cell lines used for treating lung carcinoma patients may include any of the tumor cell lines established by the invention. In particular embodiment, such composition may comprise the lung carcinoma cell line, SH-L-40, established by the invention or any cell line derived therefrom.

In yet another specific embodiment, the composition of the invention may be specifically applicable in the treatment of Colon or Gastric Carcinoma. According to another embodiment, the composition of the invention may be specifically applicable in the treatment of metastatic Colon or Gastric Carcinoma, and particularly to colon or gastric carcinoma with lung metastases.

According to such specific embodiment, the allogeneic cell lines used for treating colon or gastric carcinoma patients may include any of the tumor cell lines established by the invention. In particular embodiment, such composition may comprise the carcinoma cell line, SH-L-40, established by the invention or any cell line derived therefrom.

In yet another specific embodiment, the composition of the invention may specifically be applicable for the treatment of Ovary Carcinoma.

According to such specific embodiment, the allogeneic cell lines used for treating ovary carcinoma patients may include any of the tumor cell lines established by the invention. In particular embodiment, such composition may comprise the ovary carcinoma cell line, SH-O-30, established by the invention or any cell line derived therefrom.

As will be described in the Examples of the present invention, the 5-year 75% overall survival of the vaccinated patients in this series is higher than reported for the non-treatment group in melanoma patients (55.7% 4 year OS for resectable AJCC stage III (Eggermont et al., 2008) or a median OS of 64 months for stage IIB, IIC and III patients (Pectasides et al., 2009), compared to mean OS of 70 months in the current invention, as a median was not yet reached. In recent years, some discouraging results from adjuvant melanoma vaccine trials were reported. In the ECOG study 1694, the arm treating with a vaccine against ganglioside GM2 was associated with inferior survival rates compared to the interferon alpha-2b arm (Kirkwood et al., 2001), and a phase III study of polyvalent allogeneic vaccine versus BCG (Canvaxin) closed prematurely after interim analysis.

As indicated above, the composition of the invention comprises at least one allogeneic tumor cell line. In a specific embodiment, the tumor cell lines may be allogeneic cells expressing at least one MHC Class I HLA-A. Such HLA-A antigen may be for example any one of HLA-A01, HLA-A02, HLA-A03 (also designated HLA-A1, HLA-A2 and HLA-A3, respectively), HLA-A24, HLA-25, HLA-A26, HLA-A28, HLA-A29, HLA-A30, HLA-A32, HLA-A33, HLA-A33/2, and HLA-A66, wherein each possibility represents a separate embodiment of the invention. In specific embodiments, the cells express an MHC Class I HLA species selected from the group consisting of HLA-A2, HLA-A24, HLA-A33/2, HLA-A03, HLA-A25, HLA-A26, and HLA-A28. In specific embodiment, cell lines of the invention may express the HLA-A2.

In further useful embodiments, the tumor cell lines used by the composition of the invention may be allogeneic cells expressing at least one MHC Class I HLA-B molecule. Such HLA-B molecule may be any of the following: HLA-B08, HLA-B08/18, HLA-B3, HLA-B7, HLA-B8, HLA-B14, HLA-B15, HLA-B18, HLA-B35, HLA-B38, HLA-B41, HLA-B49, HLA-B52, HLA-B5 and HLA-B70 wherein each possibility represents a separate embodiment of the invention. In specific embodiments, the allogeneic cells express at least one MHC Class I HLA species selected from the group consisting of HLA-B3, HLA-B35, HLA-B49 and HLA-B08/18. In specific embodiment, the allogeneic cells of the invention may express the MHC class I HLA-B35.

In further useful embodiments, the tumor cell lines are allogeneic cells expressing at least one MHC Class II HLA-DR molecule including any of the following: HLA-DRB1, HLA-DRB01 and HLA-DRB104, wherein each possibility represents a separate embodiment of the invention.

In another embodiment, the tumor cell line expresses one or more tumor associated antigens. Tumor associated antigens (TAA) are known in the art and may be identified by a variety of known methods. Conveniently, TAA expression on a tumor cell may be identified by the designation of the antibodies commonly used for their detection. Table 2 summarizes some of the TAA expressed by tumor cells of the invention:

TABLE 2

Tumor Associated Antigens

| Antigen | Full name/description | Reference/accession number |
| --- | --- | --- |
| GD3 | GD3 ganglioside, identified by the R24 antibody | Nasi et al. Melanoma Res. 1997 Aug.; 7 Suppl 2: S155-62. |
| S-100 | S100 $Ca^{2+}$-binding proteins | Identified by Dako anti-S100 antibody Cat. No. N1573 |
| HMB45 | melanoma-associated antigen gp100 (Melanocyte protein PMEL), identified by monoclonal antibody HMB45 (Invitrogen) | Acc. No. P40967. http://www.uniprot.org/uniprot/P40967 |
| Melan A/MART-I | Melanoma antigen recognized by T-cells 1 (LB39-AA). | Uniprot: Q16655. Identified by Dako antibody clone A103, Cat. No. M7196 |
| HMW | High Molecular Weight - Melanoma-Associated Antigen, also known as Chondroitin sulfate proteoglycan 4 or melanoma-associated chondroitin sulfate proteoglycan | Acc. No. NM_001897 http://www.ncbi.nlm.nih.gov/nuccore/NM_001897.4 |
| MSCA | Melanocyte Cell Surface Antigen | Identified by Serotec mAb clone 60442007 |
| CD146 | Melanoma antigen, also known as melanoma cell adhesion molecule (MCAM) or cell surface glycoprotein MUC18 | Acc. No. P43121 http://www.uniprot.org/uniprot/P43121 |
| MAGE-A1 | Melanoma-associated antigen 1, also known as Cancer/testis antigen 1.1 | Acc. No. P43355 http://www.uniprot.org/uniprot/P43355 |
| MAGE-A3 | Melanoma-associated antigen 3, also known as Cancer/testis antigen 1.3 | Acc. No. P43357 http://www.uniprot.org/uniprot/P43357 |
| NY-ESO-1 | Cancer/testis antigen 1, also known as Autoimmunogenic cancer/testis antigen NY-ESO-1 | Acc. No. P78358 http://www.uniprot.org/uniprot/P78358 |
| CEA | Carcinoembryonic antigen-related cell adhesion molecule 5 (CD66e) | Acc. No. P06731 http://www.uniprot.org/uniprot/P06731 |
| PAN cytokeratin | Cytokeratin filaments of epithelial cells, expressed in epithelial cancers | Recognized by Invitrogen anti-cytokeratin mAb Clone: AE1/AE3 (Cat. No. 08-4132). |
| Ca-125-sec | Ovarian carcinoma antigen CA125, also known as Mucin16, was detected by ELISA in supernatant of cultured tumor cells | Acc. No. Q8WXI7 http://www.uniprot.org/uniprot/Q8WXI7 |
| CEA-sec | The secreted form of CEA (Carcinoembryonic antigen-related cell adhesion molecule 5) was detected by ELISA in supernatant of cultured tumor cells | See CEA above |
| CA15-3-sec | Cancer Antigen 15-3, a tumor marker used to monitor certain cancers, especially breast cancer. | Duffy MJ. Ann Clin Biochem. 1999; 36: 579-86. |

TABLE 2-continued

Tumor Associated Antigens

| Antigen | Full name/description | Reference/accession number |
|---|---|---|
| | Was detected by ELISA in supernatant of cultured tumor cells | |
| MUC-1 | Mucin 1 (MUC1, CD227), expressed in epithelial cancer | Acc. No. P15941 http://www.uniprot.org/uniprot/P15941 |

In a specific embodiment the tumor cell lines are allogeneic cells expressing at least one tumor associated antigens selected from the group consisting of GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1.

In further useful embodiments, the tumor cell lines used by the composition of the invention may be a melanoma cell line expressing HLA antigens A24, A33, B35, B49, CW04/12 and the tumor associated antigens GD3, S-100, HMB45, Melan A/MART-I, HMW, MSCA, CD146, MAGE-A1 and MAGE-A3.

In further useful embodiments, the tumor cell lines used by the composition of the invention may be a melanoma cell line expressing HLA antigens A2/24, B35 and the tumor associated antigens S-100, GD3, MAGE-A1, MAGE-A3 and NY-ESO.

In further useful embodiments, the tumor cell lines used by the composition of the invention may be a carcinoma cell line expressing HLA alleles A26, A28, B14, B35, DRB01, DRB104 and the tumor associated antigens CEA, MAGE, and MUC-1.

In further useful embodiments, the tumor cell lines used by the composition of the invention may be an ovary carcinoma cell line expressing HLA antigens A03/25, B08/18, DRB1 and the tumor associated antigens CEA Ca-125-sec and CEA-sec.

These cells may further express an additional exogenous Human Leukocyte Antigen (HLA) and/or co-stimulatory molecules.

In yet another specific embodiment, the cell lines comprised within the composition of the present invention may express at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1, wherein each possibility represents a separate embodiment of the invention.

More specifically, the cell line used in the composition of the present invention, may express the HLA antigens A24, A33, B35, B49, CW04/12 and the tumor associated antigens GD3, S-100, gp 100, Melan A/MART-1, HMW, MSCA, CD146, MAGE-A1 and MAGE-A3. In particular, the cell line provided by the invention may be a melanoma cell line designated SH-M-20 and deposited under the accession number 11052602.

According to another embodiment, the cell line comprised within the composition of the present invention, may further express the HLA-A2 antigen. Such cell line may be a melanoma cell line designated SH-M-20-A2 and deposited under the accession number 11052604.

In a further embodiment, the composition of the invention may comprise a cell line expressing the HLA antigen A2/24, B35 and the tumor associated antigens S-100, GD3, MAGE-A1, MAGE-A3 and NY-ESO. More specifically, the cell line may be a melanoma cell line designated SH-M-21 and deposited under the accession number 11052601.

In yet another embodiment the cell line comprised within the composition of the invention may express the HLA antigens A26, A28, B14, B35, DRB01, DRB104 and the tumor associated antigens, PAN cytokeratin, CEA, MAGE, and MUC-1. In particular, the cell line may be a lung carcinoma cell line designated SH-L-40 and deposited under the accession number 11052605.

In another embodiment, the composition of the invention may comprise the cell line expressing the HLA antigens A03/25, B08/18, DRB1 and the tumor associated antigens CEA Ca-125-sec and CEA-sec. Specifically, the cell line may be an ovary carcinoma cell line designated SH-O-30 and deposited under the accession number 11052603.

The tumor cell lines used by the composition of the invention may be preferably prepared from allogeneic tumor cell lines selected from the group consisting of SH-M-20, SH-M-20-A2, SH-M-21, SH-L-40 and SH-O-30 deposited under ECACC Accession Nos. 11052602, 1105604, 11052601, 11052605 and 11052603, respectively, or any cell lines derived therefrom.

Tumor cell lines for use in preparation of vaccines and immunogenic compositions may be obtained and prepared using well known methods. Established tumor cell lines may be used, e.g. the particularly preferred cell lines described herein, or may be raised from tumor biopsies. For example, cells can be obtained by disrupting biopsies by chemical (enzymatic) or physical methods (such as disruption or filtering). Cells can also be obtained from a cell suspension (fresh or cryopreserved cells). One or more of the components of the media used for expanding cells may be changed, if they are found to improve the growth of cells. In some embodiments, the purified tumor cells are irradiated prior to vaccination. For example, the tumor cells can be washed and irradiated at 5,000-35,000 rads. For instance, for the preparation of an exemplary vaccine, cells may be irradiated (e.g. to 110 Gy or 170 Gy), conjugated with DNP (e.g. as described in the Examples herein), and prepared for subcutaneous administration at $10^6$-$10^9$, typically about 1-3*$10^7$ tumor cells, optionally mixed with BCG or other adjuvants as known in the art. Without limitation, the finished product may contain e.g. 15-20 million irradiated DNP-modified melanoma cells suspended in a volume of 0.6 ml Hank's buffered salt solution (HBSS).

It may be advantageous to store purified tumor cells prior to, during, or after use of the cells for vaccination. For example, the purified tumor cells can be stored upon aquisition to facilitate transport, or to wait for the results of other analyses. In another embodiment, purified tumor cells are provided to physicians for appropriate treatment of cancer. In another embodiment, purified tumor cells are stored while awaiting instructions from a physician or other medical professional. In some cases, a portion of the purified tumor cells are stored while another portion of the purified tumor cells is further manipulated. Such manipulations can include but are not limited, to molecular profiling, cytological staining, gene or gene expression product extraction, fixation, and examination.

The purified tumor cells may be placed in a suitable medium, excipient, solution, or container for short term or long term storage. Said storage may require keeping the cells in a refrigerated or frozen environment. The tumor cells may be quickly frozen prior to storage in a frozen environment. The frozen sample may be contacted with a suitable cryopreservation medium or compound including but not limited to: glycerol, ethylene glycol, sucrose, or glucose. A suitable medium, excipient, or solution may include but is not limited to: hanks salt solution, saline, cellular growth medium, or water. The medium, excipient, or solution may or may not be sterile.

The medium, excipient, or solution may contain preservative agents to maintain the sample in an adequate state for subsequent diagnostics or manipulation, or to prevent coagulation. Said preservatives may include citrate, ethylene diamine tetraacetic acid, sodium azide, or thimersol. The sample may be fixed prior to or during storage by any method known to the art such as using glutaraldehyde, formaldehyde, or methanol. The container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile. In some cases, the sample may be stored in a commercial preparation suitable for storage of cells for subsequent cytological analysis such as but not limited to Cytyc ThinPrep, SurePath, or Monoprep.

In some embodiments, the purified irradiated tumor cells are stimulated with an adjuvant to increase immunogenicity. An adjuvant is an agent that may stimulate the immune system and increase the response to a vaccine, without having any specific antigenic effect in itself. An immunologic adjuvant is defined as any substance that acts to accelerate, prolong, or enhance antigen-specific immune responses when used in combination with specific vaccine antigens, and thus providing increased immunity to a particular disease. Adjuvants accomplish this task by mimicking specific sets of evolutionarily conserved molecules, so called PAMPs, which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA. Because immune systems have evolved to recognize these specific antigenic moieties, the presence of an adjuvant in conjunction with the vaccine can increase the innate immune response to the antigen by augmenting the activities of dendritic cells (DCs), lymphocytes, and macrophages by mimicking a natural infection. Furthermore, because adjuvants are attenuated beyond any function of virulence, they pose little or no independent threat to a host organism.

In another embodiment of the invention, the composition may further comprise an additional therapeutic agent. The term "therapeutic agent" refers to therapeutic protein, molecules, such as a protein, lipid, carbohydrate, nucleic acid and chemical compound or any other anti-inflammatory or anti-cancer drugs which when delivered to a subject, treats, cures, ameliorates, or lessens the symptoms of a given disease or condition (e.g., malignant proliferative disorders) in the subject. Alternatively, prolongs the life of the subject by slowing the progress of a terminal disease or condition. Such agents may be for example antibodies, such as the anti-CTLA-4, anti-PD1, anti-OX40, anti-GITR, anti-CD28, anti-CD40, anti-CD137; cytokines such as IL-2, which activate and stimulate the growth T-cells and natural killer cells (NK Cells), both of which are capable of destroying tumor cells directly; and small molecule compounds inhibiting STAT-3 or RAF activity.

The compositions of the invention can be administered in a variety of ways. By way of non-limiting example, the composition may be delivered intravenously, or into a body cavity adjacent to the location of a solid tumor, such as the intraperitoneal cavity, or injected directly into or adjacent to a solid tumor.

As a preferred route, the composition of the present invention may be administered via subcutaneous or intradermal injections in proximity to the tumor, via intralymphatic or intravenous injection.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be solvent or dispersion medium containing, for example, water, ethanol, polyol (for example, glycerol, propylene glycol, and liquid polyethylen glyol, and the like), suitable mixtures thereof, and vegetable oils. The proper fluidity can be maintained, for example, by the use of a coating, such as lecithin, by the maintenance of the required particle size in the case of dispersion and by the use of surfactants.

Any suitable route of administration can be used. Preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

The composition as described herein, when administered to a mammal preferably produces a result which can include alleviation of the disease (e.g., reduction of at least one symptom or clinical manifestation of the disease), elimination of the disease, reduction of a tumor or lesion associated with the disease, elimination of a tumor or lesion associated with the disease, prevention or alleviation of a secondary disease resulting from the occurrence of a primary disease (e.g., metastatic cancer resulting from a primary cancer), prevention of the disease, and stimulation of effector cell immunity against the disease.

The combined cell lines of the present invention are generally administered in the form of a pharmaceutical composition comprising at least two of the cell lines of this invention together with a pharmaceutically acceptable carrier or diluent, and optionally a further therapeutic agent. Thus, the cell lines used by this invention can be administered either individually in a kit or together in any conventional parenteral or transdermal dosage form.

Since embodiments of the present invention relate to the treatment of diseases and conditions with a combination of active ingredients at least two allogeneic cell lines which may be administered separately, the invention also relates as a further aspect, to combining separate pharmaceutical compositions in a kit form. The kit includes at least two separate pharmaceutical compositions, each comprising at least one allogeneic cell line or any cell line derived therefrom. The kit includes container means for containing all separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It should be appreciated that all components of the kit, may be administered simultaneously. Alternatively, the components can be administered sequentially in either order.

Therapeutic Use

The present invention further provides in additional aspects, methods for treating, preventing, ameliorating, reducing or delaying the onset of a proliferative disease in a mammalian subject, wherein each possibility represents a separate embodiment of the invention. The methods comprise administering to the subject (or vaccinating the subject with) a composition of the invention as defined herein. The method according to one aspect comprises the step of administering to a subject in need a therapeutically effective amount of at least two allogeneic cell lines, or of any composition comprising the same. It should be noted that in certain embodiment at least one of the cell lines expresses at least one HLA allele identical to the HLA alleles of the subject. Furthermore, at least one of the cell lines endogenously or exogenously express the HLA-B35 allele or any other HLA A or B allele that correlates with improved disease outcome.

According to one embodiment, the cell lines administered in the methods of the invention, may further express at least one tumor antigen or any peptides or fragments thereof.

In yet another embodiment of the invention, the cell lines may optionally endogenously or exogenously express the HLA-A2 antigen.

According to one particular embodiment, the method of the invention may be particularly applicable for treating, preventing, ameliorating, reducing or delaying the onset of proliferative disorder. Such disorder may be a malignant disorder. For example, melanoma, carcinoma, leukemia, sarcoma, myeloma and lymphoma. More specifically, the malignant disorder may be melanoma. In yet another embodiment, the malignant disease may be a carcinoma, specifically, lung carcinoma or ovary carcinoma.

In other embodiments, the methods of the invention lead to an increase of at least one of the OS (overall survival) and DFS (disease free survival) of said subject.

It should be noted that an increase, elevation, enhancement in at least one of OS and DFO, include in certain embodiment an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

In another embodiment, the compositions and methods of the present invention may lead to the activation of CD8-mediated cytotoxic response against the proliferative disorder. This is possible since the composition comprises at least one cell line expressing at least one HLA allele identical to the HLA alleles of the subject. The matching HLA class I allow direct activation of CD8-mediated cytotoxic response by the composition, without the need for antigen presenting cell mediation (APC). Antigen presentation by APC may favor CD4 responses, inducing regulatory T cells side by side with helper T cell populations.

According to another embodiment, at least one of the cell lines administered in the method of the invention, may express at least one HLA antigens and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1.

In yet another specific embodiment the cell line administered in the method of the present invention, may express the HLA antigens A24, A33, B35, B49, CW04/12 and the tumor associated antigens GD3, S-100, HMB45, Melan A/MART-I, HMW, MSCA, CD146, MAGE-A1 and MAGE-A3. More specifically, the cell line may be a melanoma cell line designated SH-M-20 and deposited under the accession number 11052602.

In another embodiment the cell line used in the method of the present invention may further express the HLA-A2. In particular, the cell line may be a melanoma cell line designated SH-M-20-A2 and deposited under the accession number 11052604.

According to another embodiment the cell line used in the method of the invention, may express the HLA antigens A2/24, B35 and the tumor associated antigens S-100, GD3, MAGE-A1, MAGE-A3 and NY-ESO. More specifically, the cell line may be a melanoma cell line designated SH-M-21 and deposited under the accession number 11052601.

In a further embodiment, the cell line administered in the method of the present invention may express the HLA antigens A26, A28, B14, B35, DRB01, DRB104 and the tumor associated antigens PAN cytokeratin, CEA, MAGE, and MUC-1. In particular, the cell line may be a lung carcinoma cell line designated SH-L-40 and deposited under the accession number 11052605.

In yet another embodiment, the cell line used in the method of the present invention, may express the HLA antigens A03/25, B08/18, DRB1 and the tumor associated antigens CEA Ca-125-sec and CEA-sec. More specifically, the cell line may be an ovary carcinoma cell line designated SH-O-30 and deposited under the accession number 11052603.

In another embodiment said subject expresses the B35 HLA allele. In another embodiment the method further comprising the step of assessing the presence of the B35 HLA phenotype in the subject, and if said subject displays the B35 HLA phenotype, administering said composition to said subject.

It should be appreciated that in certain embodiments, the method of the invention may use any of the compositions described by the invention.

Another aspect of the present invention relates to the use of a therapeutically effective amount of at least two allogeneic cell lines in the preparation of a composition for treating, preventing, ameliorating, reducing or delaying the onset of proliferative diseases in a subject in need. It should be noted that at least one of the cell lines expresses at least one HLA allele identical to the HLA alleles of the subject. Furthermore, at least one of the cell lines endogenously or exogenously express the HLA-B35 allele or any other HLA A or B allele that correlates with improved disease outcome.

Another aspect of the present invention refers to a method of treating cancer, said method comprising administering to a subject in need thereof a composition comprising non-proliferating whole cells as defined herein, thereby treating cancer in the subject.

There is also provided a method of treating cancer, said method comprising administering to a subject in need thereof an immunogenic composition comprising, a tumor cell line selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention, thereby treating cancer in the subject. In one embodiment the tumor cell line stably expresses an additional exogenous Human Leukocyte Antigen (HLA) and/or co-stimulatory molecule for T cells. In another embodiment said tumor cell line expresses at least one of HLA-B35, HLA-A2 and 4-1 BB ligand (4-1BBL), wherein each possibility represents a separate embodiment of the invention.

Another aspect of the present invention refers to a method of treating cancer, said method comprising administering to a subject in need thereof a therapeutic composition for treating, preventing, ameliorating, reducing or delaying the onset of a proliferative disease in a mammalian subject, said therapeutic composition comprising one or more cell lines allogeneic to the subject, wherein at least one of said cell lines expresses at least one Human Leukocyte Antigen (HLA) allele identical to the HLA alleles of said subject, and wherein at least one of said cell lines endogenously or exogenously express the HLA-B35 and HLA-A2 alleles and 4-1 BB ligand (4-1BBL), said composition further comprising one or more pharmaceutically acceptable carrier, diluent, excipient, hapten, adjuvant or additive, thereby treating cancer in the subject. In one embodiment the composition comprises at least two cell lines allogeneic to said subject. In another embodiment said at least one of said cell lines expresses at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1. In another embodiment, the tumor cell line is selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention. In another embodiment the tumor cell line stably expresses an additional exogenous Human Leukocyte Antigen (HLA) and/or co-stimulatory molecule for T cells. In another embodiment said tumor cell line expresses at least one of HLA-B35, HLA-A2 and 4-1 BB ligand (4-1BBL), wherein each possibility represents a separate embodiment of the invention.

Another aspect of the present invention refers to a method for treating, preventing, ameliorating, reducing or delaying the onset of a proliferative disease in a mammalian subject, comprising:
  a) assessing the presence of the B35 HLA phenotype in the subject, and
  b) if said subject displays the B35 HLA phenotype, administering to said subject one or more allogeneic cell lines or a composition comprising same, thereby preventing, ameliorating, reducing or delaying the onset of a proliferative disease in said subject. In one embodiment the composition comprises at least two cell lines allogeneic to said subject. In another embodiment the at least one of said cell lines expresses at least one Human Leukocyte Antigen (HLA) allele identical to the HLA alleles of said subject. In another embodiment the at least one of said cell lines endogenously or exogenously express HLA-B35. In another embodiment the at least one of said cell lines endogenously or exogenously express HLA-A2. In another embodiment the at least one of said cell lines expresses at least one HLA allele identical to the HLA alleles of said subject, HLA-B35 and HLA-A2. In another embodiment said at least one of said cell lines expresses at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1. In another embodiment, the tumor cell line is selected from the group consisting of human cell lines designated SH-M-20, SH-M-20-A2, SH-M-21, SH-O-30 and SH-L-40 that are deposited under the accession numbers 11052602, 11052604, 11052601, 11052603 and 11052605, respectively, wherein each possibility represents a separate embodiment of the invention. In another embodiment the tumor cell line stably expresses an additional exogenous HLA and/or co-stimulatory molecule for T cells. In another embodiment said tumor cell line expresses at least one of HLA-B35, HLA-A2 and 4-1 BB ligand (4-1BBL), wherein each possibility represents a separate embodiment of the invention. In some embodiments, the cancer may be a carcinoma, e.g. a metastatic carcinoma including, but not limited to melanoma, ovarian carcinoma and lung carcinoma.

As indicated above, the invention described herein encompasses a composition for the treatment of subjects in need thereof. The term "treatment" concerns improvement of at least one undesired manifestation of the disease such as: increase in disease free periods, decrease in acute disease periods (in time and severely), decrease in severity of the disease, improvement in life quality, decreased mortality, decrease in the rate of disease progression as well as prophylactic treatment before disease occurs. In particular, the composition of the invention may increase at least one of the OS (overall survival) and DFS (disease free survival) of the treated subject. Accordingly, a favorable disease outcome (or a subject responding therapeutically) refers to the outcome of a treatment resulting in an improvement of at least one undesired manifestation of the disease as described above.

The term increase may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. The term decrease may be a decrease of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. Improvement refers to a clinically recognized improvement, which may be statistically significant and/or recognized by a person of skill in the art (e.g. physician).

Melanoma as used herein and will be described in more detail hereinafter, is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes.

Carcinoma as used herein, refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges.

Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Leukemia as used herein includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Lung Carcinoma is a disease caused by the rapid growth and division of cells that make up the lungs. Lung cancers are classified according to the type of cell present in the tumor. The majority are referred to as non-small cell carcinomas. These include squamous cell or epidermoid carcinomas (the most common type worldwide), adenocarcinomas, and large cell carcinomas. Small cell carcinoma (which includes the subtypes oat cell and intermediate) comprises approximately 20% to 25% of lung cancers; it often has metastasized by the time it is detected.

Ovarian cancer is a cancerous growth arising from different parts of the ovary. Most (>90%) ovarian cancers are classified as "epithelial" and were believed to arise from the surface (epithelium) of the ovary. However, it was shown that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

Myeloma as mentioned herein, is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma.

Colon cancer (colorectal cancer), commonly known as bowel cancer, is a cancer from uncontrolled cell growth in the colon or rectum (parts of the large intestine), or in the appendix. Symptoms typically include rectal bleeding and anemia which are sometimes associated with weight loss and changes in bowel habits. Overall, 70% of cases occur in the rectum and sigmoid, and 95% are adenocarcinomas. Symptoms include blood in the stool or change in bowel habits. Screening is with fecal occult blood testing, while diagnosis is commonly done by colonoscopy.

Stomach cancer, or gastric cancer, refers to cancer arising from any part of the stomach. Etiology of stomach cancer is multifactorial, but *Helicobacter pylori* plays a significant role. Symptoms include early satiety, obstruction, and bleeding but tend to occur late in the disease. Diagnosis is by endoscopy, followed by CT and endoscopic ultrasound for staging.

In particular embodiments, the methods of the invention may be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as head and neck tumors, tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma. It should be recognized that melanoma, lung carcinoma and ovary carcinoma are of specific interest.

In yet another particular embodiment, the methods of the invention are specifically applicable for the treatment of melanoma.

The term melanoma includes, but is not limited to, melanoma, metastatic melanoma, melanoma derived from either melanocytes or melanocyte-related nevus cells, melanocarcinoma, melanoepithelioma, melanosarcoma, melanoma in situ, superficial spreading melanoma, nodular melanoma, lentigo maligna melanoma, acral lentiginoous melanoma, invasive melanoma or familial atypical mole and melanoma (FAM-M) syndrome. Such melanomas may be caused by chromosomal abnormalities, degenerative growth and developmental disorders, mitogenic agents, ultraviolet radiation (UV), viral infections, inappropriate tissue gene expression, alterations in gene expression, or carcinogenic agents. The aforementioned melanomas can be treated by the method and the composition described in the present invention.

As noted before, the term "treatment" concerns improvement of at least one undesired manifestation of the disease such as: increase in disease-free periods, decrease in acute disease periods (in time and severely), decrease in severity of the disease, improvement in life quality, decreased mortality, decrease in the rate of disease progression as well as prophylactic treatment before disease occurs. More specifically, a decrease in acute disease periods, mortality and severity of the disease, or an increase in disease free period may be of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

As used herein, "disease", "disorder" and the like, as they relate to a subject's health, are used interchangeably and have meanings ascribed to each and all of such terms.

The term "effective amount" as used herein by the composition and methods of the invention is that determined by such considerations as are known to the man of skill in the art. The amount must be sufficient to prevent or ameliorate tissue damage caused by proliferative disorders treated, specifically a malignant proliferative disorder for example, melanoma. Dosing is dependent on the severity of the symptoms and on the responsiveness of the subject to the active drug. Medically trained professionals can easily determine the optimum dosage, dosing methodology and repetition rates. In any case, the attending physician, taking into consideration the age, sex, weight and state of the disease of the subject to be treated, will determine the dose. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the cell lines used by the invention or any composition thereof in bodily fluids or tissues. Following successful treatment, it may be desirable to have the patient undergo maintenance therapy to prevent the recurrence of the disease state, wherein the cell lines used by the method of the invention or any composition thereof are administered in maintenance doses, once or more daily.

In some embodiments, the purified irradiated tumor cells are mixed with adjuvant and injected into a subject for vaccination. In some embodiments, the subject is bearing a tumor. The tumor cells can be obtained from a primary tumor, a disseminated tumor, or a metastatic tumor. In some embodiments, the tumor is a solid tumor. In some embodiments, tumor cells are administered to the subject parenterally, including intramuscular, intraarterial, intrathecal, intradermal, intraperitoneal, intrasplenic, subcutaneous, and intravenous administration. In some embodiments the adjuvant is injected directly into the tumor.

For example, without limitation, a cell vaccine of the invention may comprise about $10^6$-$10^9$, typically about 1-3*$10^7$ tumor cells, e.g. irradiated or otherwise attenuated (non-proliferating) tumor cells. Tumor cells may be treated for example by DNP, e.g. by the method of Miller and Claman (e.g. as described in the Examples). The cells may be administered together with BCG or other adjutants, according to protocols well known in the art.

In another embodiment, treatment using the cell lines or compositions of the invention, may be effected following at least 1, 2, 3, 4, 5, 6, 7, 8, 9, 10, 14, 30, 60, 90 days of treatment, and proceeding on to treatment for life.

For example, without limitation, vaccination may be effected by injection of the vaccine to several (e.g. three) adjacent sites on the upper arm or thigh, avoiding limbs where lymph node dissection has been previously performed. When using DNP-modified vaccines, vaccination may optionally be preceded e.g. two weeks before by sensitizing the recipient subject to DNP. A total of 3-20, typically 5-10, e.g. eight vaccines may be administered at 10-30 day intervals. For example, vaccination protocol may comprise 5 vaccines administered at 21 day intervals followed by three vaccines administered at 28 day intervals. Optionally, initial vaccinations (e.g. the first two vaccinations) may be preceded by intravenous cyclophosphamide administered 1-5 days before vaccination. Prior to vaccination, BCG may added to the vaccine in decreasing concentrations, e.g. as follows: a dilution of 1:50 for vaccines 1-4; a dilution of 1:100 for vaccines 5-6; and a dilution of 1:500 for vaccines 7-8. If a patient shows intense local reactivity (suppurative induration) to the first BCG vaccine, the concentration in the following vaccines is decreased accordingly.

The compositions and methods of the invention are particularly intended for the induction of immune response and treating a mammalian subject, specifically, humans, but other mammals including, but not limited to, monkeys, equines, cattle, canines, felines, mice, rats, pigs, horses, sheep and goats may be treated.

The invention also provides a method of stimulating or enhancing an immune response in a patient having cancer. For example, the invention provides a method of stimulating an immune response in a patient having colon, breast, lung, prostate, pancreas, kidney, endometrium, cervix, ovary, thyroid, or other glandular tissue cancer as well as squamous, melanoma, central nervous system, and lymphomas. For example, the compositions of the invention may be used for enhancement of the immune response in AJCC stage III (metastases to lymph nodes) post-operative patients with high risk of metastatic melanoma recurrence. The method can include the step of administering to the patient one or more allogeneic tumor cells as described herein, wherein the allogeneic cell stimulates or enhances an immune response to an autologous tumor cell in the patient. The administration of allogeneic tumor cells are advantageous for stimulating an immune response against a tumor in a patient without the need for isolating cells from the patient to generate such a tumor vaccine.

Another aspect of the present invention relates to the use of a therapeutically effective amount of at least two allogeneic cell lines in the preparation of a composition for treating, preventing, ameliorating, reducing or delaying the onset of proliferative diseases in a subject in need. It should be noted that in certain embodiments, at least one of the cell lines used by the invention may endogenously or exogenously express the HLA B35 antigen. Moreover, at least one of these cell lines may express at least one HLA allele identical to the HLA alleles of said subject. In yet a further aspect, the invention relates to a combination of at least two allogeneic cell lines for use in treating, preventing, ameliorating, reducing or delaying the onset of proliferative diseases in a subject in need. It should be noted that in certain embodiments at least one of said cell lines expresses at least one HLA allele identical to the HLA alleles of the subject. Furthermore, at least one of said cell lines endogenously or exogenously express the HLA-B35 allele or any other HLA A or B allele that correlates with improved disease outcome.

In another embodiment of the present invention, at least one of the cell lines used by the invention may further express at least one tumor antigen or any peptides or fragments thereof.

In yet another embodiment, the cell lines used by the invention, optionally endogenously or exogenously, expresses the HLA-A2 antigen.

In a further embodiment, the composition provided by the use of cell lines according to the invention, is particularly applicable in treating, preventing, ameliorating, reducing or delaying the onset of proliferative diseases. This disease may be a malignant disorder such as melanoma, carcinoma, leukemia, sarcoma myeloma and lymphoma. More specifically, the malignant disorder may be melanoma.

In yet another embodiment, the use of the invention may be for the preparation of a composition that may increase at least one of the OS (overall survival) and DFS (disease free survival) of said subject. The term increase as used in this connection may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

In a further embodiment, the use of the invention may be for the preparation of a composition that may lead to the activation of CD8-mediated cytotoxic response against the proliferative disorder.

In another embodiment, the invention provides the use of cell lines expressing at least one HLA antigen and/or tumor associated antigens selected from the group consisting of A24, A33, B35, B49, CW04/12, A2/24, A03/25, B08/18, DRB1, A26, A28, B35, DRB01, DRB104, tumor associated antigens selected from the group consisting of GD3, S-100, HMB45, Melan A/MART-I, HMW, MSCA, CD146, MAGE-A1, MAGE-A3, NY-ESO-1, CEA, PAN cytokeratin, Ca-125-sec CEA-sec, CA15-3-sec and MUC-1.

In particular, the cell line used may express the HLA antigen A24 A33, B35, B49, CW04/12 and the tumor associated antigens GD3, S-100, HMB45, Melan A/MART-I, HMW, MSCA, CD146, MAGE-A1 and MAGE-A3. More specifically such cell line may be a melanoma cell line designated SH-M-20 and deposited under the accession number 11052602.

In yet another embodiment, the cell line used by the invention may further express the HLA-A2 antigen. Specifically, the cell line may be a melanoma cell line designated SH-M-20-A2 and deposited under the accession number 11052604.

In another embodiment, the cell line used by the invention may express the HLA antigens A2/24, B35 and the tumor associated antigens S-100, GD3, MAGE-A1, MAGE-A3 and NY-ESO. In particular, the cell line may be a melanoma cell line designated SH-M-21 and deposited under the accession number 11052601.

In a further embodiment, the cell line used by the invention may express the HLA antigens A26, A28, B14, B35, DRB01, DRB104 and the tumor associated antigens PAN cytokeratin, CEA, MAGE, and MUC-1. Specifically, the cell line may be a lung carcinoma cell line designated SH-L-40 and deposited under the accession number 11052605.

In yet another embodiment, the cell line used in the preparation of the composition of the invention may express the HLA antigens A03/25, B08/18, DRB1 and the tumor associated antigens CEA CA-125-sec and CEA-sec.

In particular, the cell line may be an ovary carcinoma cell line designated SH-O-30 and deposited under the accession number 11052603.

In a further embodiment, the use of any of the cell lines described herein may be for the preparation of any of the compositions described by the invention.

Another aspect of the invention provides a combination of at least two allogeneic cell lines for use in treating, preventing, ameliorating, reducing or delaying the onset of proliferative diseases in a subject in need. In which in certain embodiments at least one of said cell lines expresses at least one HLA allele identical to the HLA alleles of the subject. Furthermore, at least one of said cell lines endogenously or exogenously express the HLA-B35 allele or any other HLA A or B allele that correlates with improved disease outcome.

In a further embodiment, the cell lines combined are any one of cell lines described in the present invention.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are presented in order to more fully illustrate some embodiments of the invention. They should, in no way be construed, however, as limiting the broad scope of the invention.

EXAMPLES

Materials
Antibodies
Monoclonal antibody (MoAb or mAb) W6/32 purchased from Dako Cat. No. M0736.
MoAb anti HLA DP, SQ, DR, antigens, purchased from Dako, Cat. No. M0775.
R24 antibody specific for melanoma associated antigen GD3
Monoclonal antibodies specific for S-100, purchased from Dako, Cat No Z0311.
HMB-45, monoclonal antibody specific for gp100, Dako Cat No M0634
Antibody to hepatitis C virus (anti-HCV)
Antibody to HIV 1/2 (anti HIV 1/2)
OKT3 antibody specific for CD3, eBioscience 16-0037-85.
Mouse anti-human HMW antibody (anti-hNG2/MCSP), FAB 2585A and Mabs 225.28 and 763.74 produced by S. Ferrone.
Mouse anti human MCSA antibody (AbD Serotec) Cat. No. 6044-2007.
FITC-conjugated mouse anti-human CD146 antibody (AbD Serotec) Cat. No. MCA2141F
FITC-conjugated HLA-A2-specific BB7.2 monoclonal antibody (mAb; Biolegend) Cat. No. 343304.
FITC-conjugated goat anti mouse secondary antibody (Jackson) Cat. No. 1150-96-146.

Media

Medium used for cultivation of tumor cell lines (referred to as Olga Medium)

For 500 ml "Olga" culture medium:
100 ml RPM11640 (cat #21875 GIBCO)
100 ml F12 HAM (Biological Industries Israel, Cat. 01-095-1A)
150 ml DMEM w/o Pyruvate (cat #41965 GIBCO)
150 ml DMEM w/o Pyruvate with 25 mM Hepes (cat #42430 GIBCO)
10% L-Glutamine 200 mM (cat #25030 GIBCO)
10% Penicillin/Streptomycin (cat #15140 GIBCO)
10% FBS Australia (cat #10099-141 GIBCO)
Mixed and filtered through a 500 ml 0.22 μm filter.
Epithelial Cells Medium (referred to as Anna's Medium)
For 1 liter medium:
10 ml Insulin-Transferin-Selenium 100× (GIBCO Cat. 41400-045)
10 ml Hepes 1M (GIBCO Cat. 15630-056)
10 ml MEM NEAA 100× (GIBCO Cat. 1140-035)
10 ml Sodium Pyruvate 100 mM (GIBCO Cat. 11360-039)
3 ml EGF (10 μg/ml stock)) (SIGMA E9644)
1 ml Hydrocortisone (0.5 μM stock) (SIGMA H6909)
170 ml FBS (GIBCO Australia cat. 10099-141)
11 ml Glutamine 100 mM (GIBCO Cat. 25030-024)
11 ml Penicillin-Streptomycin (GIBCO Cat. 15140-120)
150 ml RPMI 1640 (GIBCO Cat. 21875-034)
150 ml F12 HAM (Beit Haemek, Cat. 01-095-1A)
230 ml DMEM (GIBCO Cat. 41965-039)
230 ml DMEM (GIBCO Cat. 42430-025)
Mixed and filtered through a 500 ml 0.22 μm filter.

Reagents and Kits
TRI reagent (Sigma). Cat No. T9424
Superscript II Reverse Transcriptase (Life Technologies). Cat No. 18064-014
RNase H- (Life Technologies). Cat No. 18021-071
Matrigel (BD bioscience). Cat No. FAL356234
Ciproxin 200 (Bayer). Cat No. 81532266
Collagenase (Sigma, St. Louis, Mo.). Cat No. C1030.
DNAse (Sigma, St. Louis, Mo.). Cat No. D4527.
LiPA HLA kit (Murex Innogenetics, Ghent, Belgium).
SuperPicture HRP Polymer Conjugate Broad Spectrum (AEC) kit (Invitrogen). Cat No. Cat No87-9963.
EZ-Mycoplasma PCR. Biological Industries Cat No 20-700-20.
Lipofectamine reagent (Invitrogen, Cat No 15338).
Human IFN-gamma DuoSet (R&D, Cat No DY285E).

Patients

The patients included in the experiment disclosed by the present invention were diagnosed with cutaneous malignant melanoma with high risk for disease recurrence. Typically, these high risk patients belonged to three AJCC staging categories: (1) thick primary melanoma (>4 mm; AJCC stage IIB; 14 patients); (2) micrometastases to regional lymph nodes (LN) revealed by sentinel LN biopsy (N1a, N2a; 15 patients); and (3) macrometastases to regional LN (N1b-N3b; 13 patients).

To be eligible for the inventors' study, patients had to have undergone wide local excision of their skin melanoma with sentinel lymph node biopsy and therapeutic lymph node dissection of positive sentinel, and palpable nodes. Eligible patients had to be free of metastatic disease based on whole body CT scan or PET scan performed less than 3 weeks prior to surgery. The study was approved by the Institutional Review Board (IRB, Helsinki Committee, Hadassah-Hebrew University Medical Center, #HMO 093-09), and informed consent was obtained before enrollment into the trial.

Experimental Procedures

HLA Phenotypes and Antigen Characterization

HLA phenotyping of melanoma cell lines was performed on donors' melanoma cells using HLA-A and B low resolution molecular typing by REVERSE-SSOP using the LiPA HLA kit (Murex Innogenetics, Ghent, Belgium) according to the manufacturer instructions.

Figure 2:
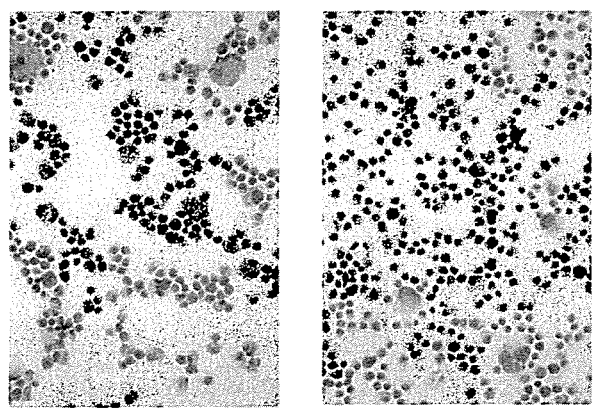
FIG. 2: Melanoma associated antigens in cell line SH-M-20.
Figure 2:
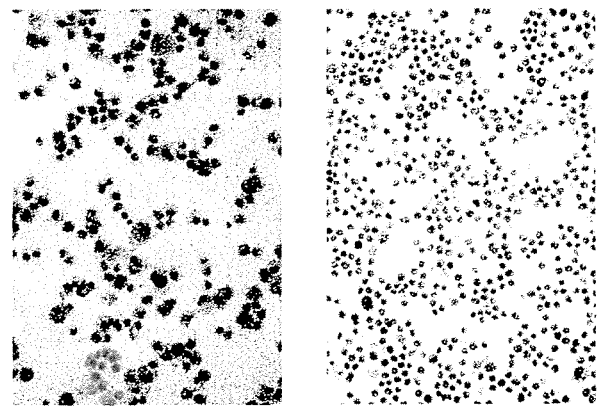

To verify HLA class I molecule expression on cell lines, MoAb W6/32 (Dako) was used. To determine HLA class II molecule expression on cell lines, MoAb anti HLA DP, SQ, DR, antigens (Dako) were used. Melanoma cell lines were stained for the melanoma associated antigens GD3 (R24 antibody), S-100 and HMB-45 (Dako), using the alkaline phosphatase anti-alkaline phosphatase (APAAP) reaction (Zymed), according to the manufacturer's protocol (FIG. 2). The HLA phenotype and antigen characterization of the cell lines used are presented in Table 3.

TABLE 3

HLA phenotype and antigen characterization of the cell lines used for vaccination
The following antibodies were used: W6/32 (for Class I), S100, HMB-45, and R24 (for GD3).

| Line no. | HLA | W6/32 | S100 | HMB-45 | R24 |
|---|---|---|---|---|---|
| 7 | A01 | | + | + | + |
| | B08 | + | | | |
| 10 | A01 | | + | ND | ND |
| | A68 | + | | | |
| 12 | A02 | | + | + | + |
| | A32 | | | | |
| | B18 | | | | |
| | B41 | + | | | |
| 14 | A01 | | + | − | − |
| | A02 | | | | |
| | B35 | | | | |
| | B15 | + | | | |
| 16 | A02 | | + | ND | ND |
| | A25 | | | | |
| | B8 B35 | | | | |
| 21 | A3 A26 | | + | + | + |
| | B18 | + | | | |
| 24 | A26 | | + | + | − |
| | B14 | + | | | |
| 30 | A03 | | + | + | + |
| | A33 | | | | |
| | B14 | | | | |
| | B18 | + | | | |
| 33 | A02 | | + | − | + |
| | A24 | | | | |
| | B15 | | | | |
| | B70 | + | | | |
| 60 | A3 A66 | | + | − | + |
| | B35 | | | | |
| | B52 | + | | | |
| 112 | A24 | | + | + | + |
| | A30 | | | | |
| | B18 | | | | |
| | B38 | + | | | |
| 135 | A1 A29 | | + | + | + |
| | B7 B18 | + | | | |
| 139 | A2 A33 | | + | + | + |
| | B38 | | | | |
| | B58 | + | | | |
| 141 | A2 A29 | | + | + | + |
| | B35 | | | | |
| | B58 | + | | | |
| 163 | A02 | | + | − | ND |
| | A32 | | | | |
| | B35 | | | | |
| | B52 | | | | |

TABLE 3-continued

HLA phenotype and antigen characterization of the
cell lines used for vaccination
The following antibodies were used: W6/32 (for Class I),
S100, HMB-45, and R24 (for GD3).

| Line no. | HLA | W6/32 | S100 | HMB-45 | R24 |
|---|---|---|---|---|---|
| 172 | A24 |  | + | − | − |
|  | A30 |  |  |  |  |
|  | B38 |  |  |  |  |
|  | B41 | + |  |  |  |
| 180 | A03 |  | + | + | + |
|  | A29 |  |  |  |  |
|  | B14 | + |  |  |  |
| 190 | A02 |  | + | − | + |
|  | A24 |  |  |  |  |
|  | B35 | + |  |  |  |
| 279 | A01 |  | + | − | − |
|  | A33 |  |  |  |  |
|  | B8 B17 | + |  |  |  |

Preparation of Tumor Cell Lines

Work was performed under GMP conditions. Tumor specimens were procured fresh and sterile. For large tumor bulks, cells were extracted mechanically or by enzymatic dissociation with collagenase and DNAse (Sigma, St. Louis, Mo.), frozen in a controlled rate freezer, and stored in liquid nitrogen in medium containing 2.5% human albumin and 20% DMSO until needed.

To expand tumor cells, multiple splits of cultures were performed in culture bottles with Dulbecco's Modified Eagle Medium (DMEM, Gibco BRL), 10% fetal calf serum (Gibco BRL), HEPES (1:500), pen-strep (1:100) and glutamine (1:100). Stocks of melanoma cells from low passages were cryopreserved for the establishment of new batches of cells as needed.

Periodical staining to assure melanocytic progeny was performed with monoclonal antibodies specific for S-100, GD3 and HMB-45 as described above. Positive staining of more than 50% of cells with at least one of these antibodies was required. Cell lines were regularly tested for the presence of mycoplasma (EZ-PCR, Biological Industries, Beth Haemek, Israel). Lines that were found contaminated were incubated in the presence of 10 mg/ml Ciproxin 200 (Bayer) for two weeks, with change of medium every three days. The lines were re-tested after treatment, and were used for vaccination only after found mycoplasma-free.

Preparation of Cell Line from Tumor Biopsy

Tumor biopsies were transferred to a sterile Petri dish. A large biopsy (2-10 g) was transferred to a 10 cm sterile Petri dish and a small biopsy (up to 2 g) was transferred to a 3.5 cm sterile Petri dish. The saline from the original container of the biopsy was collected and was centrifuged (1000-1500 rpm for 5-10 min). The cells were suspended in culture medium. The Biopsy was cut in to smaller pieces with a razor blade and was filtered through a 70 μm nylon filter into 50 ml sterile tubes and centrifuged (1000-1500 rpm for 5-10 min). The pellet in each tube was suspended in culture medium containing 10% DMSO (for freezing) and transferred in 1 ml aliquots to freezing ampoules and frozen.

Alternatively, approximately 1-2% of a large biopsy and up to all of a small biopsy was taken and transferred to two 250-ml flasks. Culture medium containing 20% FCS was added. After overnight incubation cells were examined under the microscope; if there was a monolayer, the non-adherent cells were poured into a sterile 50 ml tube, and fresh medium, with 10% FCS was added. If there was no monolayer, the washing was preformed the next day. These cells are PASSAGE 0. When the monolayer was confluent, the medium was collected as "conditioned medium". The conditioned medium was frozen, for mycoplasma testing, or as a growth factor when needed. If the non-adherent cells collected contained many mononuclear cells, they were centrifuged, suspended in culture medium with 10% DMSO, and frozen. PBS was added to the flask, tilted lightly, and discarded. Trypsin was added as follows: To 5 ml flasks, 1 ml were added, to 250 ml flasks, 3 ml were added and to 600 ml flasks, 4 ml were added. The cells were incubate at 37° C. and were Checked every two minutes. When the monolayer was loosened (not more than 5 min), the flask was hit to loosen all the cells, and medium containing FCS was added. The cells were distributed into new flasks. These cells are passage 1.

Freezing of Tumor Cell Line Protocol

Confluent cells from a T25 flask were frozen in one cryo-tube and from a T50 flask in two cryo-tubes. Cryo-tubes were labeled by Patient Name, Line Number, Passage Number and date.

The freezing medium (2 ml per cryo-tube) was prepared with 0.2 ml DMSO, 0.6 ml FCS (Brazil) and 1.2 ml DMEM medium for one cryo-tube. Some PBS was added to the flask, tilted lightly, and discarded. Trypsin was added as follows: to 50 ml flasks, 1 ml was added, to 250 ml flasks, 3 ml was added and to 600 ml flasks, 4 ml was added.

The cells were incubate at 37° C. and were Checked every two minutes. When the monolayer was loosened (not more than 5 min), the flask was hit to loosen all the cells, and DMEM medium containing FCS was added. The cells were transferred to tubes, centrifuged at 1,100 rpm for 7 minutes and re-suspended in freezing medium. The tubes were securely capped, and immediately stored in deep-freeze boxes at −70° C. for at least 2 days (and up to 7 days). The tubes were transferred to a liquid nitrogen container and marked by date of storage.

Thawing of Tumor Cell Line

Cryo-tubes were transferred from liquid nitrogen to a stand in a container with distilled water. After cryo-tubes were completely thawed they were dried and clean with 70% ethanol. The content of the cryo-tubes was transferred to a 12 ml tube containing 10 ml Olga medium (MFI_25) with 10% FCS (Australian) and centrifuged at 1,100 rpm for 7 minutes. The content of the tubes were resuspended in Olga medium and transferred to flasks, as follows: to T25 flask 7 ml was added and to T50 flask 15 ml was added. The Flasks were incubated at 37° C. with 8% CO2.

Mycoplasma Testing

Melanoma cells were set aside for mycoplasma testing every two weeks. The last batch of cells grown was tested first. Previous batches were tested only if the last batch was contaminated.

At least 0.5 ml spent medium was collected into a sterile tube (the cells must have been in the same medium for at least 3 days) as well as, spent medium from at least 20% of the flasks from the same date. The tube was labeled with the patient number, type of cells and date of collection (can be stored up to one week in the refrigerator). Then, the tube with its contact was Centrifuged 250 g (2000 rpm) for 5 minutes, dated and the supernatant was transferred into a fresh sterile tube and centrifuged 14,000 rpm for 15 minutes to sediment mycoplasma. The supernatant was carefully discarded and the pellet was kept (the pellet may not be visible). The pellet was resuspended with 20 μl of the Buffer Solution (EZ-PCR) and mixed thoroughly with a micropipette. Finally, the tube with its content was heated to 95° C. for 3 minutes, a 25G needle was put through the cap of the tube, to avoid excessive pressure and the tubes were stored at −20° C. until PCR is performed.

EZ-Mycoplasma PCR was performed according to the manufacturer's instructions. Tumor cells that were found contaminated were incubated in the presence of 10 mg/ml Ciproxin 200 (Bayer) for two weeks, with change of medium every three days. The cells were re-tested after treatment, and were used only after found mycoplasma-free.

Tests for Viral Infectious Agents

The following viral antigen or antibodies were tested in the Tumor cells (Table 4). For all cell lines the tests were negative.

TABLE 4

Viral infectious agents test

| Viral antigen or antibody | Test | Performance site |
|---|---|---|
| Hepatitis B surface antigen (HBsAg) | HBsAg (V2), Abbott Axsym System, B7P400 | Liver Unit/Division of Medicine, Hadassah |
| Antibody to hepatitis C virus (anti-HCV) | HCV version 3.0, Abbott Axsym System, B3B440 | Liver Unit/Division of Medicine, Hadassah |
| Antibody to HIV 1/2 (anti HIV 1/2) | HIV 1/2 gO, Abbott Axsym System, B3D40 | Clinical Virololgy, Hadassah |

Master Cell Bank

Each ampoule contains between $3 \times 10^6$ and $5 \times 10^6$ cells, cryopreserved as detailed above.

Storage: Few ampoules were stored in a liquid nitrogen container in the Immunotherapy laboratory, Sharett Institute of Oncology, room 57, and a few ampoules were stored in the Cryo-preservation Unit of the Hadassah Hospital. These laboratories are at remote sites. Storage is performed in the liquid phase of liquid nitrogen. All tubes are labeled with blue caps. In order to avoid microbial contamination, the cells are manipulated under aseptic conditions. In addition, the media used for cell growth is filtered through a 0.2 µm filter. The cells in the MCB have been tested and found negative for infectious agents.

Transfection Protocol

The cells were transfected using Lipofectamine reagent, according to the manufacturer's instructions.

FACS Protocol

For FACS analysis, cells were washed twice in FACS buffer consisting of PBS supplemented with 0.5% bovine serum albumin (BSA) and 0.1% sodium azide and resuspended in the same buffer. The cells were stained with the specified antibody for 30 min at 4° C., then washed twice in FACS buffer and analyzed on an LSRII analyzer (Becton Dickinson). Appropriate isotype controls were used. The data were analyzed using "FCS express" software (De Novo Software, Los Angeles, Calif.).

ELISA Protocol

IFN-γ ELISA was done according to the manufacturer's instructions (R&D).

RT PCR Expression of Different Tumor Antigens in the Tumor Cell Lines

Total cytoplasmic RNA was isolated from logarithmically growing cell cultures using TRI REAGENT (Molecular Research Center, Cincinnati, Ohio) according to the manufacturer's instructions. Four micrograms of total RNA were reverse transcribed into cDNA with 200 units of Superscript II RNase H-Reverse Transcriptase (Life Technologies). The cDNA quality was assured by testing the expression of L19. cDNA corresponding to 500 ng of total RNA was subjected to PCR amplification (PTC-100; MJ Research Inc. Watertown, Mass.) for 40 cycles, as follows: 1 min at 92° C.; 1 min at 55° C., 1 min at 72° C. The following primer sequences (5'→3') were used:

For the expression of MAGE-A1 the following primers were used:

```
                         (as denoted by SEQ. ID. NO. 8)
forward (f) ACT ACC ATC AAC TTC ACT CG,
and (as denoted by SEQ. ID. NO. 9)
reverse (r) CTC CCA TCA TAC ACC TCC.
```

For the expression of MAGE-A3 the following primers were used:

```
                         (as denoted by SEQ. ID. NO. 10)
(f) TGG AGG ACC AGA GGC CCC,
and (as denoted by SEQ. ID. NO. 11)
(r) GGA CGA TTA TCA GGA GGC CTG C.
```

For the expression of NY-ESO-1 the following primers were used:

```
                         (as denoted by SEQ. ID. NO. 12)
(f) GTT CTA CCT CGC CAT GCC TTT,
and (as denoted by SEQ. ID. NO. 13)
(r) GCA GTC AGT CGG ATA GTC AGT.
```

Amplification was followed by 10 minutes incubation at 72° C. Products were electrophoresed on 1% agarose gels and monitored under UV.

Establishment of melanoma-specific T lymphocytes from peripheral blood mononuclear cells Cryo-preserved mononuclear cells (MNC-GS-1457) were stimulated in vitro with autologous irradiated melanoma at an effector:target ratio of 10:1.

After five days in culture in the presence of low dose IL-2, the MNC were re-stimulated with autologous melanoma at a 5:1 ratio. Following the second re-stimulation, MNC-GS-1457 cells were incubated in the presence of OKT3 antibody, to induce rapid expansion (REP) of the lymphocytes in order to obtain large numbers of cells. Cell activity was measured in the course of (day 6) and the end (day 13) of the REP procedure. The phenotype of the cells obtained after two stimulations (I) and after REP (II) was determined by FACS analysis, and their activity was measured by IFN-γ secretion in the presence of autologous or irrelevant melanoma cells (ELISA assay).

Vaccine Preparation

The vaccine was tailored for each patient, depending on his HLA type. Three different melanoma lines with a minimum of one allelic identity and preferably 2-3 identical alleles on loci A and B were chosen for each vaccine (Table 5). Ten million cells of each line were administered in every dose of vaccine. On treatment day, the cells were thawed, washed and irradiated to 110 Gy. A sample was stained with trypan blue and counted after irradiation. Conjugation of melanoma cells with DNP was performed by the method of Miller and Claman [Miller, S. D., and H. N. Claman. J Immunol 117:1519-1526 (1976)]. Briefly, melanoma cells were washed with Hanks balanced solution-no HSA, re-suspended to a concentration of 5×10⁶/ml, mixed, incubated for 30 minutes, and washed again. Each cell line was separately injected by the subcutaneous route. Bacille Calmete Guerin (BCG) was mixed with the first two vaccine doses, for its adjuvant effect.

TABLE 5

HLA class I phenotype and list of the lines used to prepare the vaccine for each patient

| Patient no. | Patient HLA A | B | Lines used for vaccine | | |
|---|---|---|---|---|---|
| 234 | A33 A66 | B17 (58) B41 | 139 | 60 | 12 |
| 2019 | A1 A— | B35 B41 | 10 | 12 | 141 |
| 279 | A1 A33(19) | B8 B17 | 7 | 30 | 279 |
| 2026 | A3 A26(10) | B7 B38 (16) | 21 | 30 | 135 |
| 2027 | A11 A30(19) | B13 B52 (5) | 112 | 172 | 163 |
| 2028 | A24 A26 | B07 B38 | 21 | 112 | 172 |
| 306 | A2 A26 | B07 B38 | 16 | 21 | 139 |
| 2031 | A24 A33 | B18 B44 | 30 | 112 | 172 |
| 2034 | A11 A26(10) | B38 B52 | 21 | 112 | 163 |
| 330 | A29(19) A32(19) | B14 B7 | 180 | 135 | 163 |
| 2036 | A—A1 | B41 B7 | 10 | 7 | 172 |
| 2037 | A02 A03 | B07 B13 | 21 | 141 | 190 |
| 2041 | A02 A03 | B44 | 163 | 21 | |
| 2042 | A01 66 | B35 38 | 7 | 60 | 172 |
| 2043 | A02 | B35 B52 | 60 | 141 | |
| 2044 | A01 A26 | B08 B55 | 7 | 10 | 21 |
| 2002 | A2 A3 | B 14 B 38 | 139 | 180 | 33 |
| 2003 | A 26 A 3 | B 44 B 7 | 21 | 135 | |
| 2004 | A 2 A 66 | B 41 | 12 | 60 | 190 |
| 2006 | A1 A3 | B35 B18 | 21 | 60 | 135 |
| 2007 | A29 | B35 B45 | 141 | 16 | 190 |
| 212 | A 124 | B35 B44 | 10 | 14 | 33 |
| 2008 | A24 (9) A3 | B14 B35 | 190 | 112 | 30 |
| 2010 | A2 A28 | B7 B38(16) | 139 | 135 | 190 |
| 2014 | A24 A30 | B18 B41 | 172 | 12 | 112 |
| 2015 | A23 A31 | B38 B50 | 112 | 172 | 139 |
| 2018 | A24 | B35 | 190 | 172 | 16 |
| 2022 | A1 A26(10) | B38(16) B35 | 21 | 10 | 16 |
| 2025 | A1 A32 (19) | B57 (17) B18 | 12 | 10 | 135 |
| 2029 | A01 A33 | B08 B49 | 7 | 139 | 135 |
| 2039 | A01 A25 | B08 B18 | 7 | 10 | 16 |
| 2009 | A28 | B7 B38 | 135 | 139 | 141 |
| 466 | A02 A33 | B08 B50 | 16 | 141 | 190 |
| 2049 | A24 A32 | B07 B40 | 112 | 163 | 172 |
| 463 | A02 A26 | B1517 B27 | 16 | 21 | 190 |
| 2047 | A24 | B35 | 16 | 172 | |
| 2048 | A01 | B08 B18 | 7 | 10 | 21 |
| 453 | A02 A23 | B07 B49 | 16 | 163 | 172 |
| 2046 | A11 A32 | B35 B49 | 163 | 16 | |
| 2045 | A02 A31 | B35 | 16 | 141 | |
| 2016 | A2 A11 | B35 B58 (17) | 141 | 139 | 190 |
| 2017 | A68 | B14 | 24 | 10 | 30 |

Vaccination Procedure

On days 1 and 2 patients were sensitized to DNP by topically applying 0.1 ml of 2% DNP dissolved in acetone-corn oil (Sigma) to the inner aspect of the arm. On day 14 the vaccine was injected into three adjacent sites on the upper arm or thigh, avoiding limbs where lymph node dissection had been previously performed. The first two vaccines were preceded by intravenous cyclophosphamide, 300 mg/m2 given four days earlier. A total of eight vaccine doses were administered at 21—(vaccines 1-5) and 28—(vaccines 6-8) day intervals (Lotem et al., 2002).

DTH Evaluation

Previous clinical studies confirmed that skin reactivity against tumor cells, as measured by delayed type hypersensitivity reaction, is a simple predictor of survival (Lotem et al., 2002). For that reason, 1×10⁶ unmodified melanoma cells of each line chosen for the vaccine were irradiated to a dose of 170 Gy and injected intradermally. DTH was measured by the maximal diameter of erythema 48 hours post injection. A clinically significant DTH response was considered as erythema of 5 mm at the injection site of at least two lines used for vaccination.

Evaluation of Results

Apart of minor inconveniency and grade I itching at the injection site, no systemic toxicity was observed in vaccinated patients. Patients did not report any other side effects.

Statistical Analysis

Statistics were calculated using established methods. Study endpoints included: Disease recurrence—defined as histologically or radiologically proven local or metastatic lesions appearing after enrollment into the trial. Disease related mortality—any event of death as a result of disease progression. Time interval to recurrence was measured from the time of surgery until the first documented event of recurrence.

Overall survival (OS) and disease free survival (DFS) were estimated by the Kaplan-Meier's product limit method. Univariate analysis of treatment impact on survival was calculated by the log rank test. P value<0.05 was considered statistically significant.

Preparation of Viral Particles

Viral particles for transfection/transduction of HLA-A2 expressing vectors were produced by transient co-transfection into 293T-phoenix cells. The TransIT-LT1 transfection reagent (Mirus, Madison, USA) was used as described herein. The components of the transfection were calculated for 10-cm tissue culture dishes.

293T-phoenix cells were routinely cultured in 90% Dulbecco's modified Eagle's medium (DMEM, Gibco-BRL, Gaithersburg, Md.) supplemented with 10% Fetal Calf Serum (Gibco-BRL, Gaithersburg, Md.), 1 mM L-glutamine, 100 u/ml penicillin and 50 g/ml streptomycin.

24 hours prior to transfection, $1.8 \times 10^6$ 293T-phoenix cells were plated on a 10-cm tissue culture dish, in 10 ml 293T-phoenix tissue culture medium. The confluence of the cells on the day of transfection was approximately 70%.

Cells were incubated over-night at 37° C. The next day, transfection was performed in a total volume of 600 l.

Preparation of plasmid mixture: 8 g of the MSGV-1 A2 plasmid and 8 g of VSV-G envelope plasmid were mixed in serum-free medium (Optimem, Gibco).

Transfection reagent solution was prepared in a second eppendorf tube. The volume of Optimem is determined according to the volumes of the other components of the transfection (transfection reagent and plasmid DNA). 55 l of TransIT-LT1 transfection reagent was added directly to the Optimem medium, in a dropwise manner and mixed completely by gently flicking the tube. The mixture was incubated at room temperature for approximately 5 minutes.

Reagent solution was added to the plasmids mixture in a dropwise manner and mixed by gently flicking the tube. The mixture was incubated at room temperature for 15-45 minutes, to enable reagent/DNA complex formation.

The reagent/DNA complex mixture was added dropwise to the 293T-phoenix cells and the tissue culture dish was gently rocked to ensure even distribution of the mixture. The cells were incubated for 16-20 hours at 37° C.

For the collection of recombinant viral particles, 16-20 hours after transfection the culture medium of 293T-phoenix cells was replaced with 10 ml fresh medium. After additional incubation for 24 hours at 37° C., supernatant containing the viral particles was collected. Supernatants were filtered through a 0.45 M filter (Sartorius, Goettingen, Germany). 10 ml of fresh medium was added to the transfected cells for 24 hours incubation.

Example 1

HLA-B35 Correlates with a Favorable Outcome Following Adjuvant Administration of an HLA-Matched Allogeneic Melanoma Vaccine A total of forty two patients were recruited for the inventors study between September 2002 and July 2009. The mean age at initial diagnosis was 50 years (median 51 years). Other demographic and clinical data including gender, stage of disease, and HLA phenotype of the patients are summarized in Table 6. Each patient was vaccinated at least five times. HLA phenotype of the lines used for vaccination is shown in Table 3, and phenotype of each patient, and cell lines used for individual vaccination, are summarized in Table 5.

TABLE 6

Demographic, clinical and HLA phenotype data of the study cohort

|  |  | No. of patients | % of total |
|---|---|---|---|
| Total |  | 42 | 100 |
| Gender | Male | 27 | 64 |
|  | Female | 15 | 36 |
| Age range | 1-78 years (Mean: 50) |  |  |
| Stage* | IIB (T4) | 14 | 33 |
|  | Micrometastases (N1-2a) | 15 | 36 |
|  | Macrometastases (N1-3b) | 13 | 31 |
| Frequent HLA phenotypes | HLA-A02 | 12 | 29 |
|  | HLA-A01 | 11 | 26 |
|  | HLA-B07 | 10 | 24 |
|  | HLA-B35 | 13 | 31 |
|  | HLA-B38 | 10 | 24 |

*T and N classifications according to the American Joint Committee on Cancer (AJCC) Staging System

Disease Free Survival (DFS) and Overall Survival (OS)

Patients were followed up for a period of 4-86 months (mean 49 months). The 5-year overall survival of the entire cohort was 75% and the disease free survival was 67% (Table 7). Overall survival correlated favorably with a DTH response of at least 5 mm (p=0.03, Table 8) to two out of the three cell lines used to vaccinate a patient, whereas DFS did not correlate with DTH response (p=0.38). Patient outcome at the time of the analysis outlined in Table 9 further shows that a majority of the patients (76%) had no evidence of disease (NED) at the time of analysis.

Due to the small study cohort, the inventors elected not to analyze survival breakdown by UICC-AJCC disease stage.

TABLE 7

Disease free survival (DFS) and overall survival (OS) of the patients participating in the study

|  | Median | Mean (months) | 5-year survival rate |
|---|---|---|---|
| DFS | Not reached | 60 (49-71*) | 61% |
| OS | Not reached | 70 (60-79) | 75% |

*Lower bound and higher bound 95% confidence intervals

TABLE 8

Correlation of OS with delayed type hypersensitivity (DTH) to at least two of the lines that composed the vaccine

| DTH | Median (months) | Mean (months) | significance |
|---|---|---|---|
| >5 mm | Not reached | 75 | .03 |
| <5 mm | 66 | 49 |  |

TABLE 9

Status of the patients at the end of the study

| Status | No. of patients | % of total |
|---|---|---|
| NED* | 32 | 76 |
| AWD | 2 | 5 |
| DOD | 8 | 19 |

Correlation of Disease Outcome with HLA Phenotype

Figure 1B:
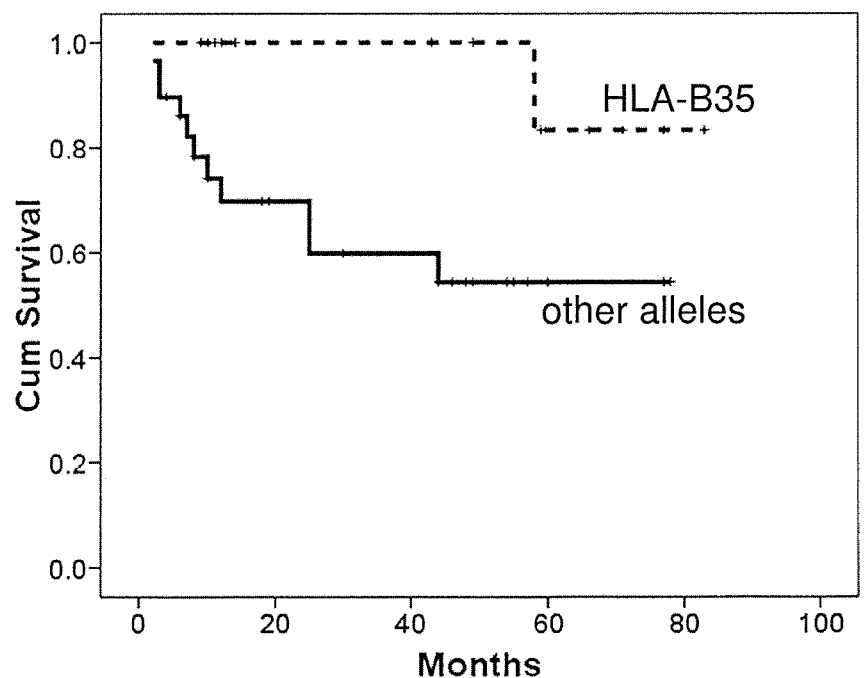
Figure 1C:
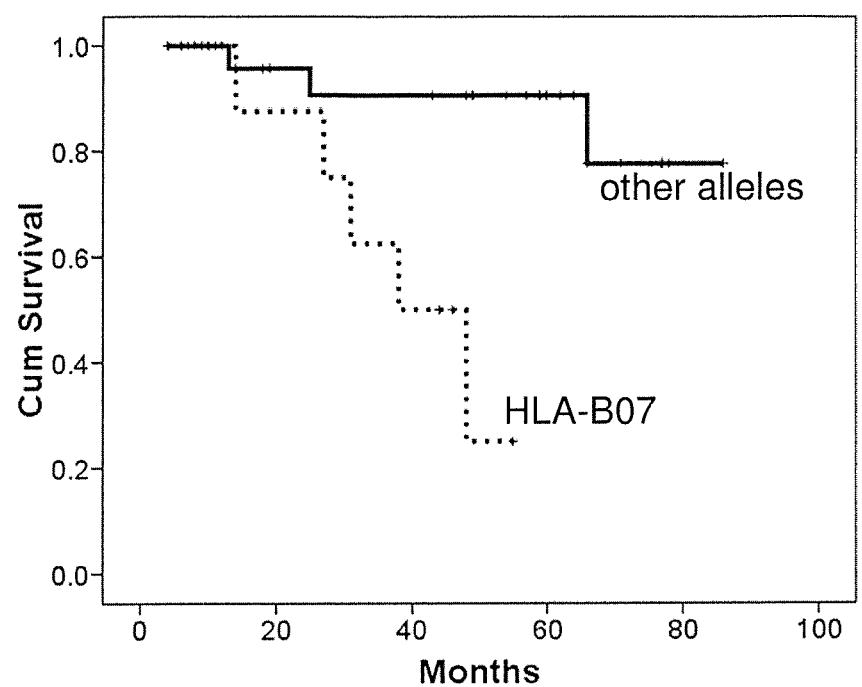

As clearly shown in FIG. 1 correlation was found between two HLA-B phenotypes and disease outcome (Cum Survival indicates cumulative). First, as shown in FIG. 1A, patient's group expressing the HLA-B35 phenotype had a mean DFS time of seventy nine months (with median not reached), compared to forty nine months for the non-HLA-B35 group (p=0.029). Better OS of the HLA-B35 phenotype group was also observed (FIG. 1B, p=0.033, all cases censored). Of the thirteen patients with HLA-B35 phenotype, twelve were vaccinated using at least one line with this phenotype (Table 5). Second, the group with an HLA-B07 phenotype had a significantly shorter OS time interval compared to the non-HLA-B07 group (p=0.003). However, for this phenotype group, DFS was not significantly affected (FIG. 1).

These results clearly show a positive correlation between a favorable disease outcome and the B35 HLA phenotype. This advantage was not due to one particularly immunogenic donor line, as patients were vaccinated with different cell lines with the B35 phenotype (Table 5). Therefore the inventors further present in the following Examples new cell lines expressing the HLA-B35 phenotype, for use as efficient melanoma cell vaccines.

Example 2

Development and Characterization of Cell Line SH-M-20

In attempt to create efficient cell vaccine the inventors developed a melanoma cell line expressing B35 phenotype.

A lymph node was obtained from a 73 year old man diagnosed with metastatic melanoma. To the inventor's knowledge, the patient did not suffer from an infectious disease at the time the biopsy was taken. No known epidemic was prevalent at the time.

Cell line was established as described in Experimental Procedures.

HLA phenotyping was performed on melanoma cells as described above, defining a phenotype of HLA A24; A33, B35; B49, CW04/12(04/08).

The cell line was next assayed for the following melanoma associated antigens GD3, S-100, gp100, Melan A/MART-I, using the alkaline phosphatase anti-alkaline phosphatase (APAAP) reaction (Zymed). As shown by the staining presented by FIG. 2, all examined melanoma associated antigens are expressed by the SH-M-20 cell line.

Figure 3A:
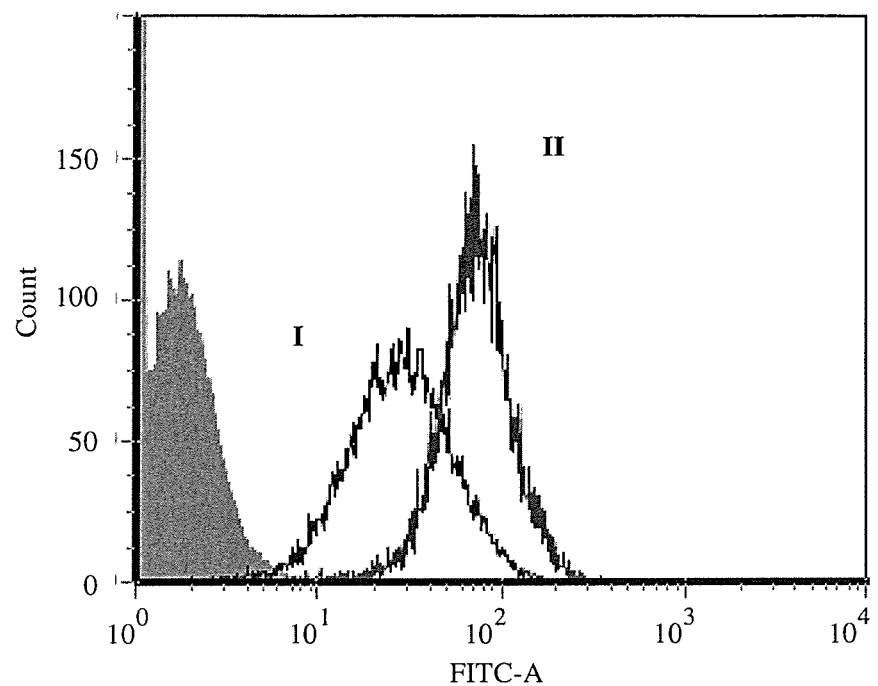
FIG. 3A-3B: Characterization of SH-M-20 melanoma cell line antigen expression.

Expression of High Molecular Weight Melanoma Associated Antigen (HMW-MAA) in SH-M-20 cells, as well as expression of HLA-A, B, C was detected as shown by the FACS analysis of FIG. 3A. As can be seen from the figure, these cells express HMW and to a higher extant also HLA-A, B, C antigens.

Figure 3B:
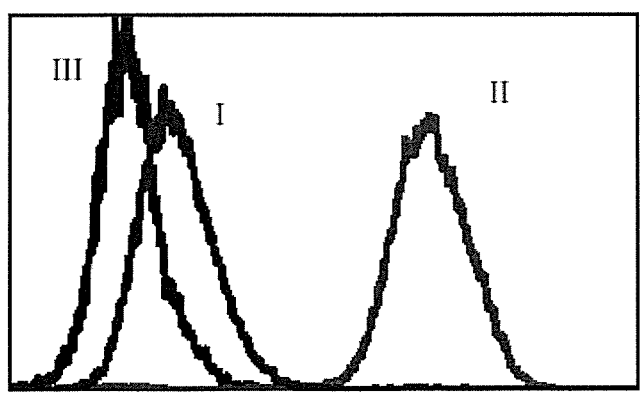

The FACS analysis presented by FIG. 3B clearly indicates that the SH-M-20 cell line highly express CD146 and to a lesser extent, the melanoma cell surface antigen MCSA.

Figure 4:
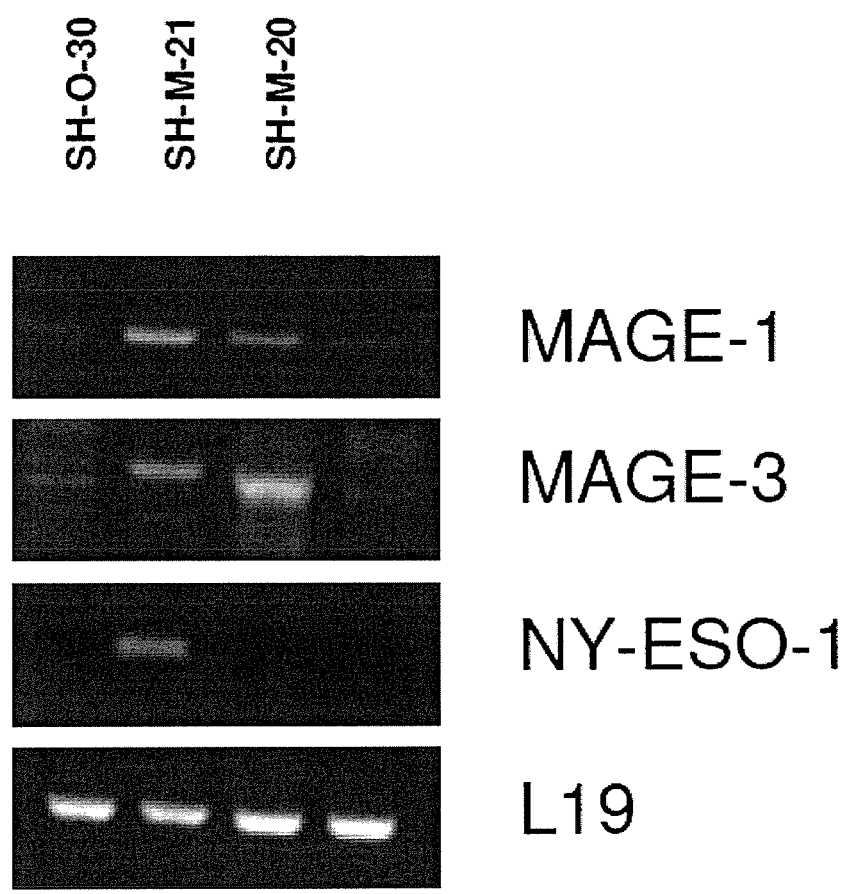
FIG. 4: Characterization of SH-M-20, SH-O-30 and SH-M-21 cell lines. Expression of MAGE-A1, MAGE-A3 and NY-ESO-1 cancer-testis antigens in SH-O-30, SH-M-21 and SH-M-20 cells examined by RT-PCR.

As shown by the RT-PCR analysis of FIG. 4, SH-M-20 cells express MAGE-A3, at a small extant express MAGE-A1, and do not express NY-ESO-1 cancer-testis antigens.

Figure 5:
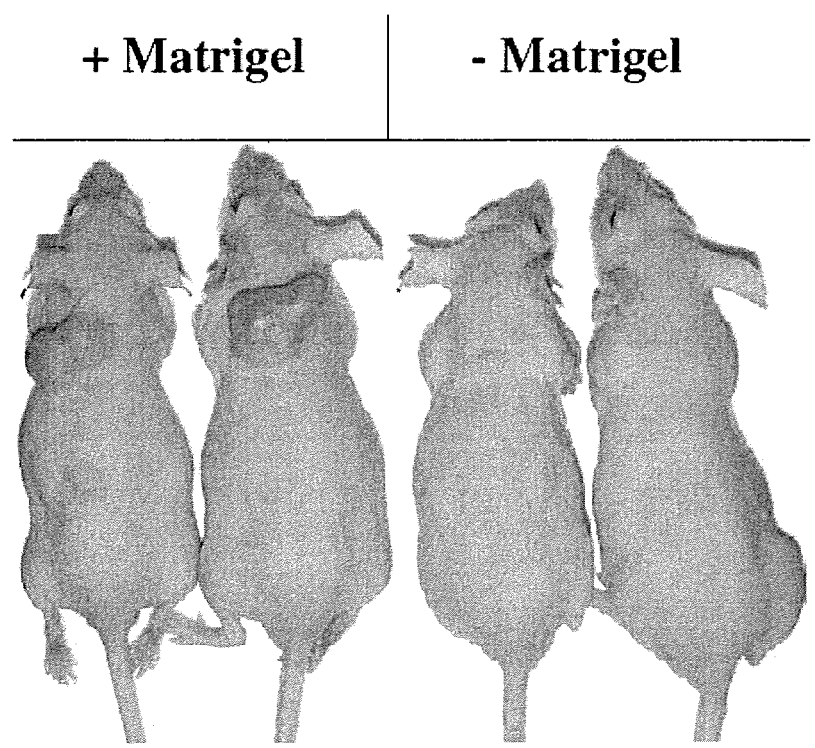
FIG. 5: Characterization of in vivo tumor formation of the SH-M-20 cell line. The Figure shows outcome of mice injected with SH-M-20 cells admixed 1:1 with or without matrigel.

These cells were further characterized by examining the ability to form tumors in vivo. Therefore, Male CD1 nu/nu mice were injected s.c. in the upper back with $1 \times 10^6$ SH-M-20 cells admixed 1:1 with Matrigel (BD Biosciences). As shown by FIG. 5, tumors were seen with mice that were injected with cells in Matrigel.

The SH-M-20 cell line was deposited under the Budapest's treaty under the accession number 11052602.

Example 3

Development and Characterization of Cell Line SH-M-20-A2

The Examiners next examined the possible effect of exogenously expressing an HLA antigen, by the established cell line. Therefore a stable transfection of the HLA A2 antigen was next performed on SH-M-20 cells.

The SH-M-20-A2 clone is a stable HLA-A2 transfectant of SH-M-20 cells, established after transfection with pcDNA3-HLA-A2 plasmid, as described in experimental procedures.

For the generation of the pcDNA3-HLA-A2 plasmid, the HLA-A0201 full-length cDNA containing the HLA-A0201 open reading frame with EcoRI restriction sites in 3'-end and 5'-end was cloned into EcoRI unique restriction site of pcDNA3 expression vector. Following transfection, expression of surface HLA-A2 was confirmed by FACS staining with HLA-A2-specific mAb (clone BB7.2).

Figure 6:
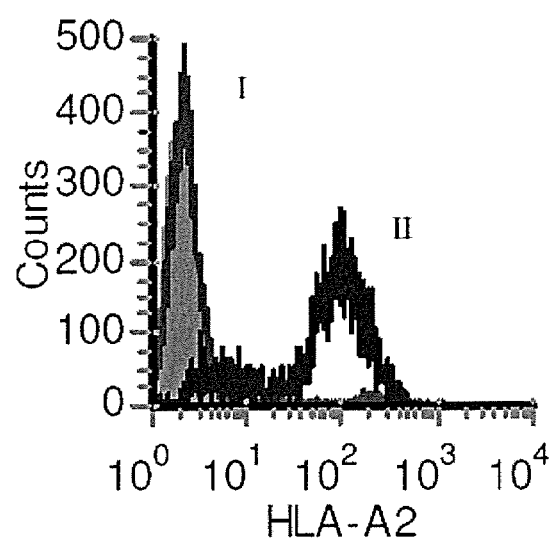
FIG. 6: FACS analysis of HLA A2 expression on SH-M-20-A2 cell lines. Histogram II shows a clear expression of the HLA-A2 antigen and histogram I shows background staining (secondary Ab only).

The expression of HLA-A2 was evaluated by fluorescence-activated cell sorting (FACS) using an HLA-A2 specific BB7.2 monoclonal antibody (mAb; AbD Serotec) as shown by FIG. 6.

The expression of different melanoma associated antigens, MAGE-A1, MAGE-A3 and NY-ESO-1, by the SH-M-20-A2 cells as well as the ability of tumor formation in vivo was found to be identical to the parent SH-M-20 shown in FIG. 4.

SH-M-20-A2 process and present tumor-associated antigens in a HLA-A2-specific manner and stimulate CD8 T cells derived from HLA-A2+ melanoma patients.

The inventors next examined the ability of the SH-M-20-A2 cells that exogenously express HLA-A2 antigen, to induce a direct activation of CD8 cells.

Figure 7:
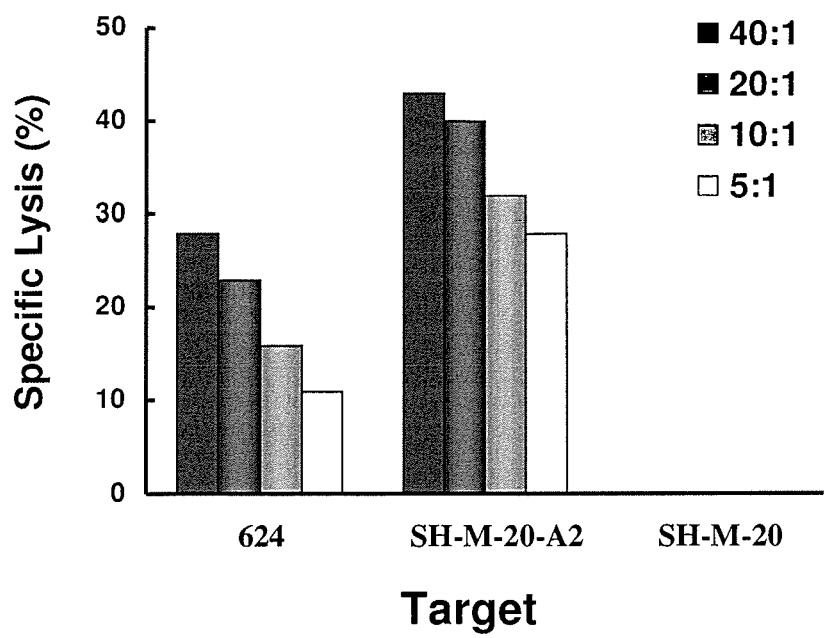
FIG. 7: Specific lysis of cells expressing exogenously the HLA-A2 antigen, by TILs specific for A2. The Figure demonstrates specific lysis of cells which exogenously express HLA-A2 antigen (SH-M-20-A2), by TILs derived from HLA-A*0201 melanoma patients. Cells which do not express the HLA-A2 antigen were not lysed by the specific TILs.

Therefore, tumor-infiltrating lymphocytes (TILs), derived from an HLA-A*0201+ melanoma patient were co-cultured with SH-M-20-A2 melanoma. The 624mel (HLA-A2+) and parental SH-M-20 (HLA-A2−) melanomas were used as positive and negative controls, respectively. In vitro cytotoxicity assays were performed as described earlier [Machlenkin. et al., Clinical Cancer Research 11:4955-4961 (2005)]. Briefly, lymphocytes were washed, resuspended in complete medium consisting of RPMI 1640 supplemented with 10% heat-inactivated human AB serum, 2 mmol/L L-glutamine, 1 mmol/L sodium pyruvate, 1% nonessential amino acids, 25 mmol/L HEPES (pH 7.4), 50 µmol/L β-mercaptoethanol, and combined antibiotics, and admixed at different ratios with 5,000 [35S]L-methionine labeled melanoma. CTL assays were performed in U-shaped microtiter wells at 37° C., 5% CO2 for 5 h. Percentage of specific lysis was calculated as follows: % lysis=(cpm in experimental well−cpm spontaneous release)/(cpm maximal release−cpm spontaneous release)×100. As clearly demonstrated by FIG. 7, there is efficient killing of 624mel and SH-M-20-A2 but not of SH-M-20 cells. These results further demonstrate the feasibility of using an exogenously expressed HLA antigen to stimulate specific presentation of tumor antigens to cognate T cells.

Figure 8:
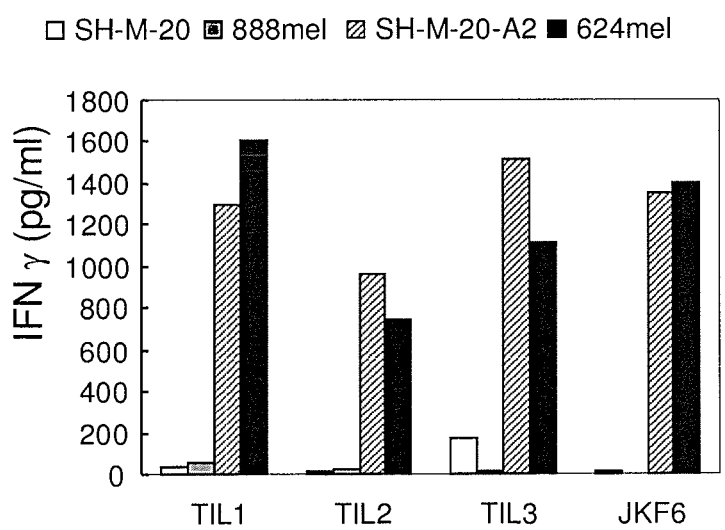
FIG. 8: Analysis of IFN-γ secretion in SH-M-20-A2 cell versus SH-M-20 cells. The Figure shows secretion of IFN-γ by TIL's derived from HLA-A2$^+$ melanoma patients, that were co-cultured with cells which express or with cells which do not express the HLA-A2 antigen.

The inventors next examined the ability of the exogenously expressed HLA-A2 antigen to stimulate specific inflammatory response by measuring IFN-γ secretion. JKF6 is a TIL culture of known specificity (MART 1/Melan A27-35-HLA-A2) that was used in these experiments. Therefore, TILs from HLA-A2+ melanoma patients were co-cultured with SH-M-20-A2 versus parental SH-M-20 cells for 20 h followed by analysis of IFN-γ secretion by ELISA (R&D). FIG. 8 clearly demonstrates that all tested TILs secreted ample amounts of IFN-γ as a result of co-culture with SH-M-20-A2 but not with SH-M-20. 624mel and 888mel melanomas were used as HLA-A2+ and A2− negative controls, respectively.

The SH-M-20-A2 cell line was deposited under the Budapest's treaty under the accession number 11052604.

Example 4

Development And Characterization of Cell Line SH-M-21

In an attempt to provide variety of tumor cell lines for use as allogeneic combined cell vaccine, the SH-M-21 cell line was next established.

A lymph node was obtained from an 88 year old man with metastatic melanoma. Following diagnosis the patient underwent autologous melanoma vaccination, IL-2 treatment and chemotherapy, but died three years later. To the inventor's knowledge, the patient did not suffer from an infectious disease at the time the biopsy was taken. No known epidemic was prevalent at the time.

HLA phenotyping was performed on melanoma cells as described above. The phenotypes found were HLA-A2/24, HLA-B35.

The melanoma cell line was next assayed for expression of melanoma associated antigens using the SuperPicture HRP Polymer Conjugate Broad Spectrum (AEC) kit (Invitrogen) and FACS analysis. As indicated by Table 10, both S-100 and the melanoma associated antigen GD3 are highly expressed by the SH-M-21 cell line, whereas these cells do not express the gp100 TAA.

TABLE 10

Expression of different TAA's by the SH-M-21 cell line

| Cell line | S-100 | HMB-45 | R-24 | Class I | Class II |
|---|---|---|---|---|---|
| SH-M-21 | +4* | 0% | +3 | +4 | +4 |

*The number proceeded by the + sign expresses the strength of staining (+1, weakest; +4, strongest).

Sub Cloning of the Cell Lines

The original cell line SH-M-21 was further sub cloned by limiting dilution. Cloning was performed by distributing two cells/well in 96-well plates using Olga medium. Eight clones were obtained, and Clone #5 was chosen, based on stronger antigen expression and growth. This clone, termed SH-M-21.5, was used to prepare the master cell bank. Clone 14, SH-M-21.14 was also further grown, and 20 vials were frozen as a master cell bank backup. This clone expressed the same markers as SH-M-21.5, differing only in the strength of their expression. Table 11 summarizes the information for these two sub clones.

TABLE 11

Expression of different TAA's by the SH-M-21 sub clones

| | date | Passage no. | MAGE-3 | NY-ESO | # of vials |
|---|---|---|---|---|---|
| SH-M-21.5 | 24-28 Oct. 2010 | 10-11 | 80% +1* | 80% +2 | 25 |
| SH-M-21.14 | 24 Oct. 2010 | 9 | 30% +1 | 10% +1 | 20 |

*the percentage expresses the number of cells stained out of the total number of cells; the number preceded by the + sign expresses the strength of the staining (+1, weakest; +4, strongest).

The SH-M-21 cell line was deposited under the Budapest's treaty under the accession number 11052601.

Example 5

Development and Characterization of Cell Line SH-L-40

To further examine the effect of the HLA B35 antigen in cell vaccines other than melanoma, the inventors next established a lung metastasis carcinoma cell line expressing the B-35 phenotype. Therefore, pleural fluid was obtained from an 88 year old female with Carcinoma of upper lobe, diagnosed in 2009. The patient was also diagnosed for hypothyroidism, insulin dependent diabetes mellitus, hypertension, chronic renal failure, peripheral vascular disease, chronic diplopia. The patient died on Feb. 10, 2010. To the inventor's knowledge, the patient did not suffer from an infectious disease at the time the biopsy was taken. No known epidemic was prevalent at the time.

HLA phenotyping was preformed as described above, defining phenotypes of A*26 A*28 B*14 B*35 DRB*01 DRB1*04.

Epithelial cell markers were measured using the SuperPicture HRP Polymer Conjugate Broad Spectrum (AEC) kit, according to the manufactures instructions. Secreted markers were measured by ELISA using the Immulite system (Cell Marque). These assays were performed in the Laboratory for Cancer Markers, Mount Scopus Campus, Hadassah Medical Organization. The results are summarized in Table 12.

TABLE 12

Expression of different epithelial cell markers by the SH-L-40 cell line

| | Secreted markers | | | Cell markers | | | | |
|---|---|---|---|---|---|---|---|---|
| Cell line | CEA | CA15-3 | CA-125 | PAN cytokeratin | CEA | MAGE | NYESO-1 | MUC-1 |
| SH-L-40 | 25.3 | 47.2 | 28.9 | 80% (+4) | 20%-50% (+2) | 20% (+2) | 0% | 20%(+2) |

As shown by the table, the established cell line highly expresses cytokeratin, and moderately expresses carcinoembryonic antigen (CEA), MAGE and MUC-1, but does not express NYESO-1. In addition, the line secreted CEA, cancer antigen (CA)15-3 and CA-125. Taken together, these results point towards the epithelial source of the tumor.

The SH-L-40 ell line was deposited under the Budapest's treaty under the accession number 11052605.

Example 6

Development and Characterization of Cell Line SH-O-30

In yet another embodiment for a carcinoma cell vaccine, the inventors next established an ovary carcinoma cell line.

Ascetic fluid was obtained from a 57 year old female diagnosed with metastatic papillary cystadenocarcinoma of the ovary stage IV. Following diagnosis, partial debulking was performed and the patient was treated with combination chemotherapy of cytoxan, adriamycin, cis-platinum and 6-hexamethyl melamine for one year. At the time the fluid was obtained, no remission was achieved, and the patient died two months later. To the inventor's knowledge, the patient did not suffer from an infectious disease at the time the biopsy was taken. No known epidemic was prevalent at the time.

HLA phenotyping was performed on melanoma cells as described above. The phenotypes found were A03/25 B08/18 DRB1.

Expression of tumor markers was measured using the SuperPicture HRP Polymer Conjugate Broad Spectrum (AEC) kit. Secreted markers were measured by ELISA using the Immulite system.

Sub Cloning of SH-O-30 Cell Line

The original cell line was sub cloned by limiting dilution (September, 2010). Cloning was performed by distributing 2 cells/well in 96-well plates using Olga medium. Fourteen clones were obtained. Clone 10 was chosen, based on antigen expression and growth. This clone, termed SH-O-30.10, was used to prepare the master cell bank. Clone 2, SH-O-30.2 was also further grown, and 30 vials were frozen as a master cell backup. This clone expressed the same markers as SH-O-30.10, differing only in the strength of their expression.

Table 13 summarizes the expression of different antigens by said sub clones.

TABLE 13

Expression of different epithelial cell markers by the SH-0-30 cell line

| | date | Passage no. | $CEA^1$ | Ca-125-sec | CEA-$sec^2$ | # of vials |
|---|---|---|---|---|---|---|
| SH-O-30.10 | 20 Oct. 2010 | 9 | 40% $+2^3$ | 492 | 9 | 50 |
| SH-O-30.2 | 20 Oct. 2010 | 9 | 20% +3 | 316 | 6.6 | 30 |

$CEA^1$ (carcinoembryonic antigen) cell marker.
CEA-$sec^2$, secreted CEA.
$^3$the percentage expresses the number of cells stained out of the total number of cells; the number preceded by the + sign expresses the strength of the staining (+1, weakest; +4, strongest).

SH-0-30 cell line was deposited under the Budapest's treaty under the accession number 11052603.

Example 7

Establishment of Melanoma Specific T Lymphocytes from Peripheral Blood Mononuclear Cells Analysis of phenotype and function of the cells obtained following two stimulations in the presence or absence of autologous melanoma As indicated in Example 3, the inventors examined the ability of the cell line SH-M-20-A2 to stimulate certain T cell population specific for the HLA antigen presented by the cells. Therefore, specific TIL cell lines were established and characterized.

Figure 9:
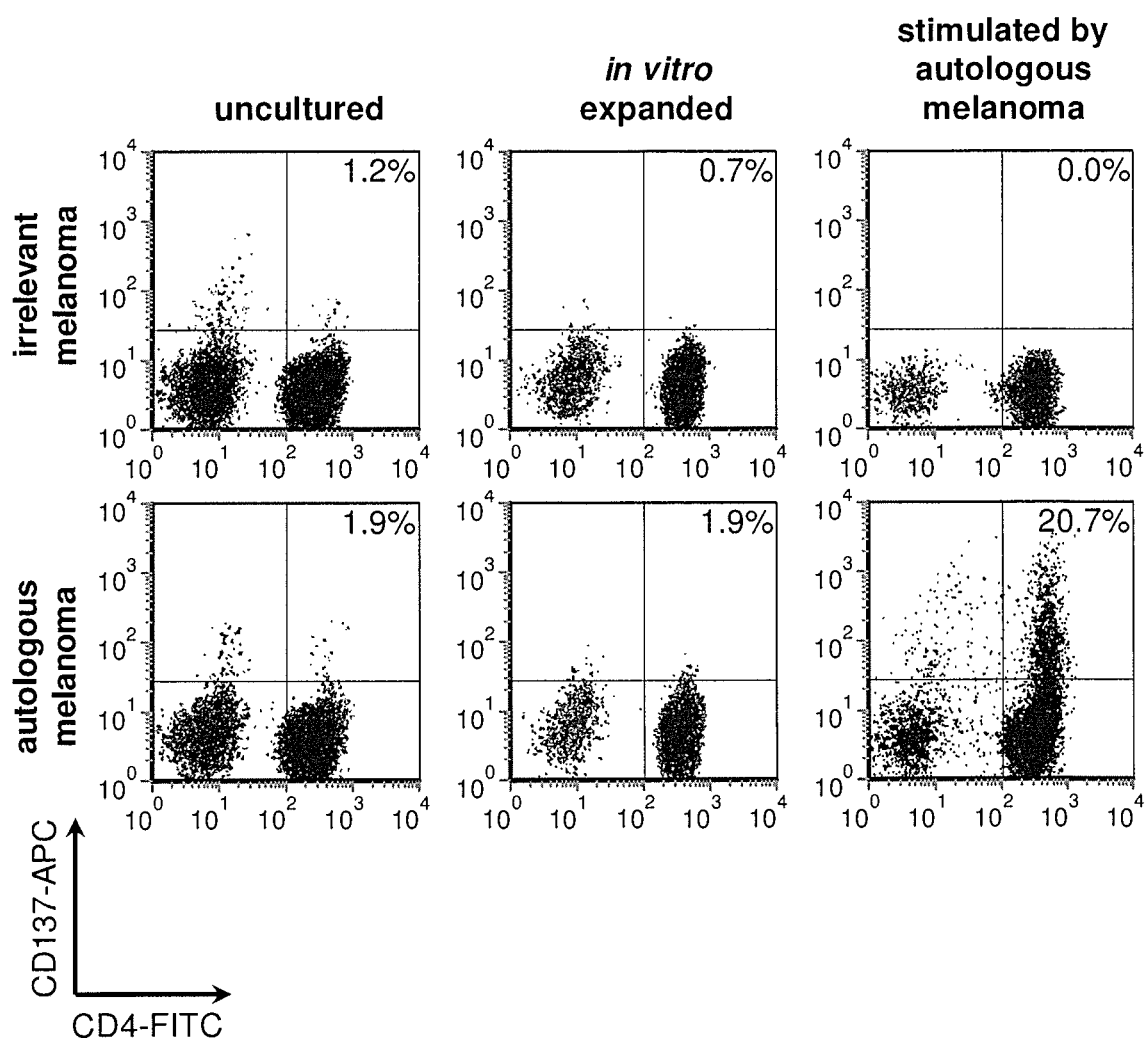
FIG. 9: CD137 expression on CD4 lymphocytes following in vitro simulation with melanoma. The right column presents the phenotype and activity of lymphocytes following stimulation in the presence of autologous (bottom) or irrelevant (top) melanoma. The middle column shows in vitro expanded cells in the absence of melanoma. The left column serves as control. Anti-CD137 antibody is labeled with APC and anti-CD4 antibody is labeled with FITC.
Figure 10:
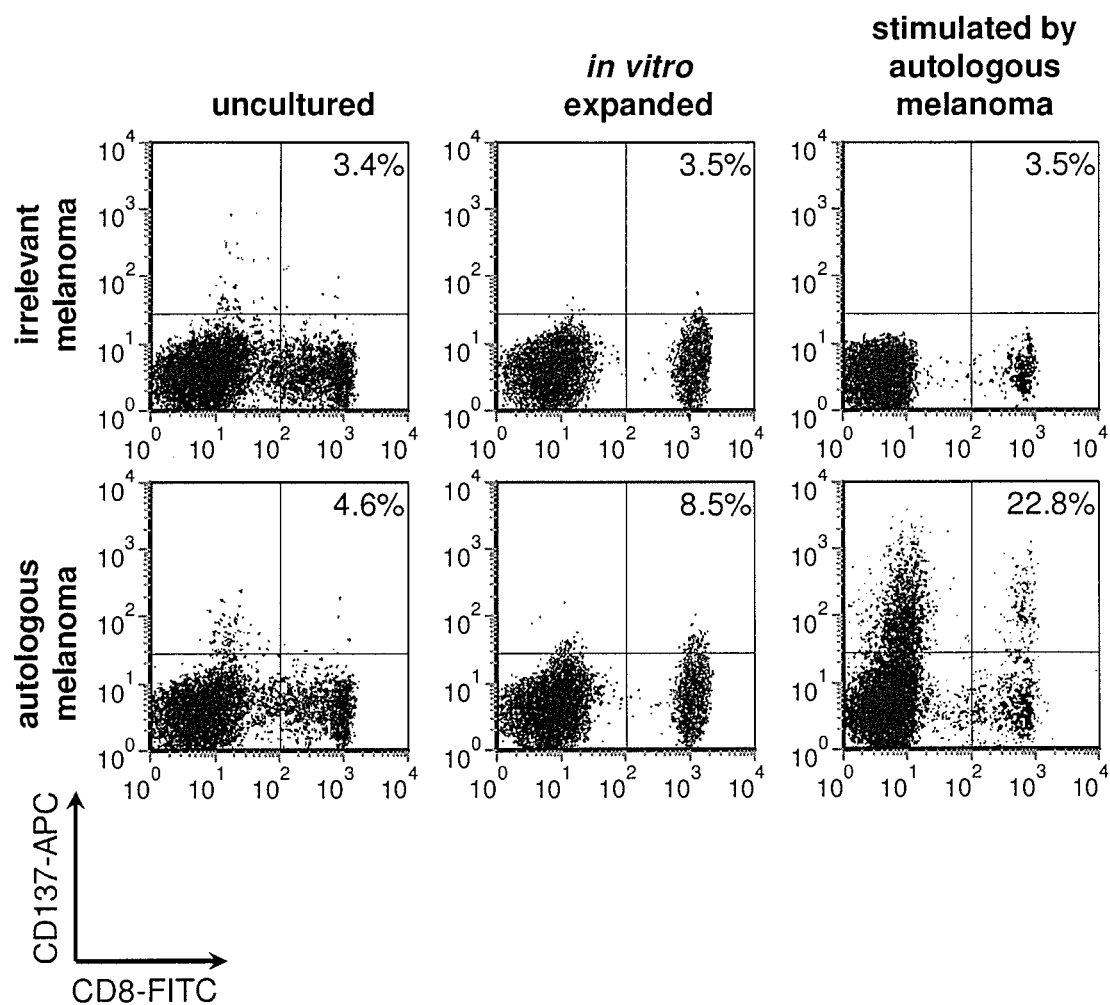
FIG. 10: CD137 expression on CD8 lymphocytes following in vitro simulation with melanoma. Right column is the phenotype and activity of lymphocytes following stimulation in the presence of autologous (bottom) or irrelevant (top) melanoma. Middle column is in vitro expanded cells in the absence of melanoma. Left column serves as control. Anti-CD137 antibody is labeled with APC and anti-CD8 antibody is labeled with FITC.

FIGS. 9 and 10 summarize the phenotype and activity of lymphocytes following stimulation in the presence of autologous melanoma (right columns) or in in vitro expanded cells in the absence of autologous melanoma (middle columns).

Following stimulation, the distribution of CD4+ and CD8+ cells was 85% and 15% respectively. The level of CD137 (also known as 4-1 BB) expression, a surface co-stimulatory glycoprotein present on activated T lymphocytes, was determined on CD4 and CD8 cells. The results show that incubation in the presence of autologous melanoma induced a marked increase in CD137 expression on CD4+ lymphocytes (FIG. 1). Increase of CD137 on CD8+ cells (FIG. 10) was less marked, due to higher levels of non-specific stimulation.

Figure 11:
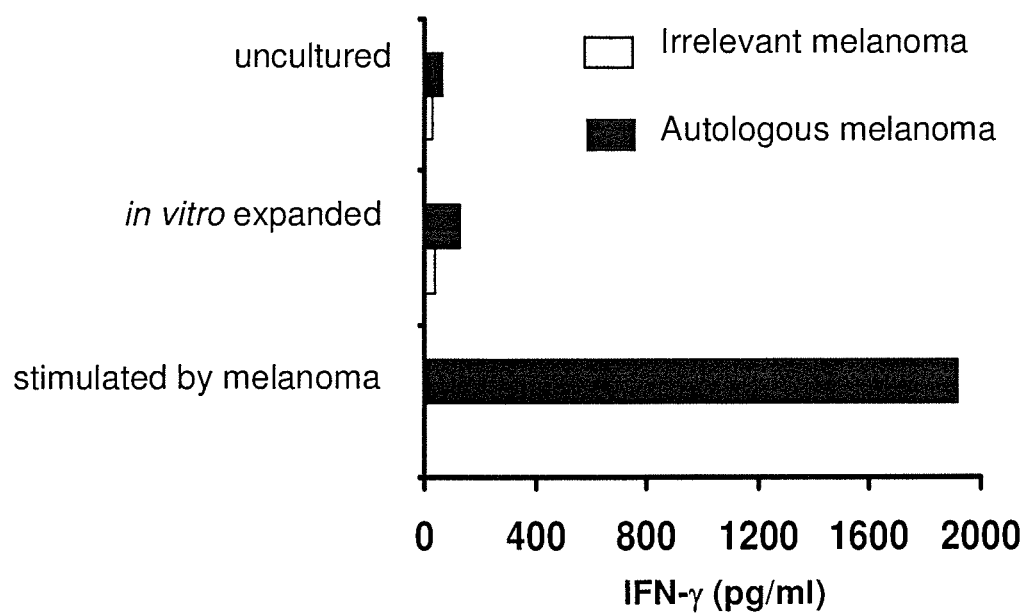
FIG. 11: IFN-γ secretion by patient-derived PBMC following in vitro stimulation with melanoma. Histograms show IFN-γ secretion by lymphocytes stimulated with melanoma (bottom), expanded in vitro in the absence of melanoma (middle) or control uncultured lymphocytes (top). Clear bars indicate irrelevant melanoma and black bars represents autologous melanoma.

FIG. 11 shows IFN-γ secretion of melanoma-stimulated lymphocytes, following a 24 hour re-stimulation in vitro in the presence or absence of autologous melanoma. Autologous melanoma clearly induced highly significant levels of IFN-γ secretion.

Analysis of phenotype and function of lymphocytes following rapid expansion (REP)

Following in vitro stimulation in the presence of autologous melanoma, cells were incubated in the presence of OKT3 for REP. On day 6 of REP, the percentage of CD4+ cells in the cultures increased to 95% of the total number of lymphocytes. At this point, the cultured cells were divided. One part continued the REP as before (bulk), and the other part was separated by magnetic beads to obtain purified CD4+ and CD8+ populations. Both the bulk and the purified cells continued the REP until day 13. On day 13 (end of REP), the percentage of CD4+ lymphocytes in the bulk increased to >95%.

Table 14 summarizes the measurement of IFN-γ secretion during (day 6) and after (day 14) REP, following 24 hours of re-stimulation in vitro in the presence or absence of autologous melanoma. From the data presented, it appears that in these cultures, the major cell population contributing to IFN-γ secretion is CD4+ cells.

In the course of the REP, bulk lymphocyte proliferated ×1,700. A total of $10^9$ bulk cells were cryo-preserved. $10^8$ CD4+ cells were also cryo-preserved.

A population of CD4+ activated melanoma-reactive lymphocytes was obtained from peripheral blood MNC-GS-1457, and cryo-preserved.

TABLE 14

IFN-gamma secretion by patient-derived PBMC following in vitro stimulation with melanoma and in vitro Rapid Expansion Procedure ELISA (pg/ml).

| | Targets | |
|---|---|---|
| | irrelevant melanoma | autologous melanoma |
| day 6 | | |
| CD8 | 0 | 1,800 |
| CD4 | 0 | >10,000 |
| bulk lymphocytes | 60 | >10,000 |
| day 13 | | |
| CD8 | n.d. | n.d. |
| CD4 | 0 | 43,900 |
| bulk lymphocytes | 0 | 45,000 |

Example 8

Generation of HLA-A2-Specific T Cells Against Tumor (Epithelial)-Associated Antigens In this series of experiments, HLA-A2-specific T cells against epithelial tumor-associated antigens, were produced as a tool to measure the functional success of HLA-A2 transfection of epithelial tumor cell lines.

To this end, RNA encoding alpha and beta chains of TCR, specific to HLA-A2-restricted epitope of p53 protein, was electroporated into donor peripheral blood cells. Using this tactic, we took advantage of the fact that p53 is a common antigen overexpressed in many tumors, including ovary, gastric and melanoma. The results from these experiments show that T cells that specifically recognize HLA-A2-restricted epitope of p53 antigen were successfully produced. These T cells could be used as a tool to measure (i) the functionality of the inserted HLA-A2 into epithelial tumor cell lines; (ii) immunogenicity of the epithelial vaccine.

Example 9

HLA-A2 Transgene Expression in Epithelial Cancer Cell Lines

Initially, a number of attempts were performed to transduce SH-O-30 ovary cell line with HLA-A2-encoding DNA plasmid, using pcDNA3-HLA-A2 construct, described above. In contrast to melanoma cell lines, SH-O-30 did not stably express HLA-A2, although transient appearance of the transgene was observed. To circumvent a low efficiency of DNA-based transfection of the cells, transfection by viral vectors, exemplified by retroviral construct MSGV1-HLA-A0201-ires-Neo (SEQ ID NO: 15, described below), was performed.

Transfection/transduction was performed as follows. Viral particles were produced as described in Experimental Procedures above. SH-L-40 and SH-0-30.10 were routinely cultured in 60% Dulbecco's modified Eagle's medium (DMEM), 20% RPMI 1640 medium and 20% F12 medium supplemented with 10% Fetal Calf Serum (all from Gibco-BRL, Gaithersburg, Md.), 1 mM L-glutamine, 100 u/ml penicillin and 50 g/ml streptomycin.

24 hours prior to transfection, 0.4×10⁶ SH-L-40 or SH-0-30.10 cells were plated on a 6 well tissue culture plate. Cells were incubated over-night at 37° C. The next day, transduction was performed.

SH-L-40 and SH-0-30.10 cells were incubated over night with 10 ml of the virus containing medium, in the presence of 4 g/ml polybrene (Sigma, St. Louis, Mo.) at 37° C. This step was repeated, and after 2 days 1.2 mg/ml of selection antibiotics (G-418) was added.

Figure 12A:
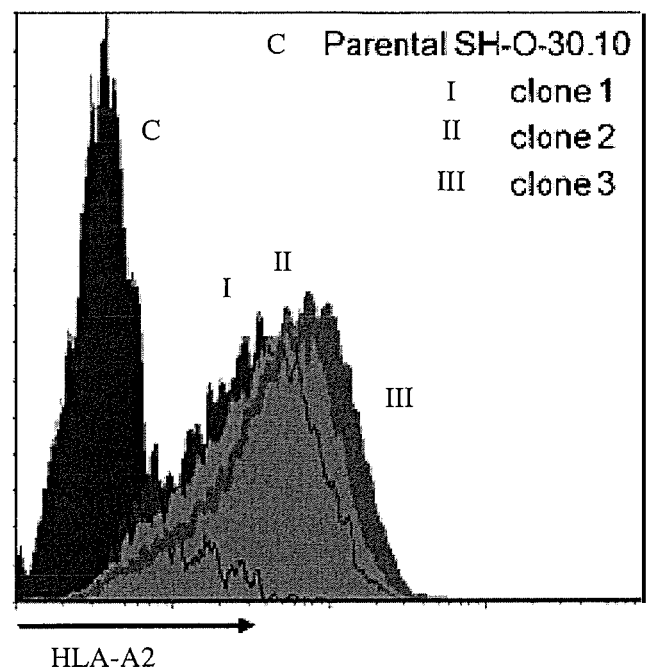
FIGS. 12A-B: Stable expression of HLA-A2 transgene in ovary SH-O-30.10 and gastric SH-L-40 cell lines.
Figure 12B:
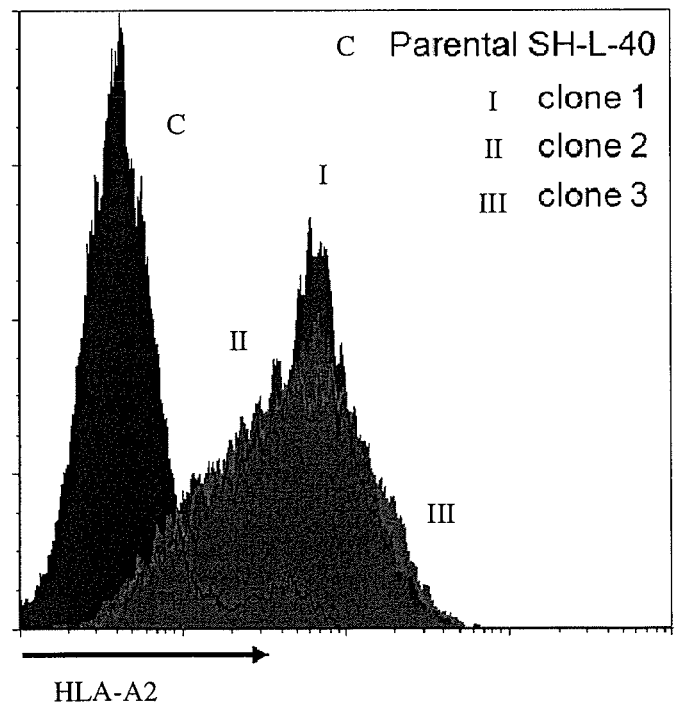

HLA-A2 expression on selected cells was evaluated by flow cytometry. Using this approach, a number of SH-O-30.10 clones with stable expression of surface HLA-A2 were produced (FIG. 12A). In the same way, HLA-A2⁺ clones were established for the gastric SH-L-40 cell line (FIG. 12B).

Figure 13A:
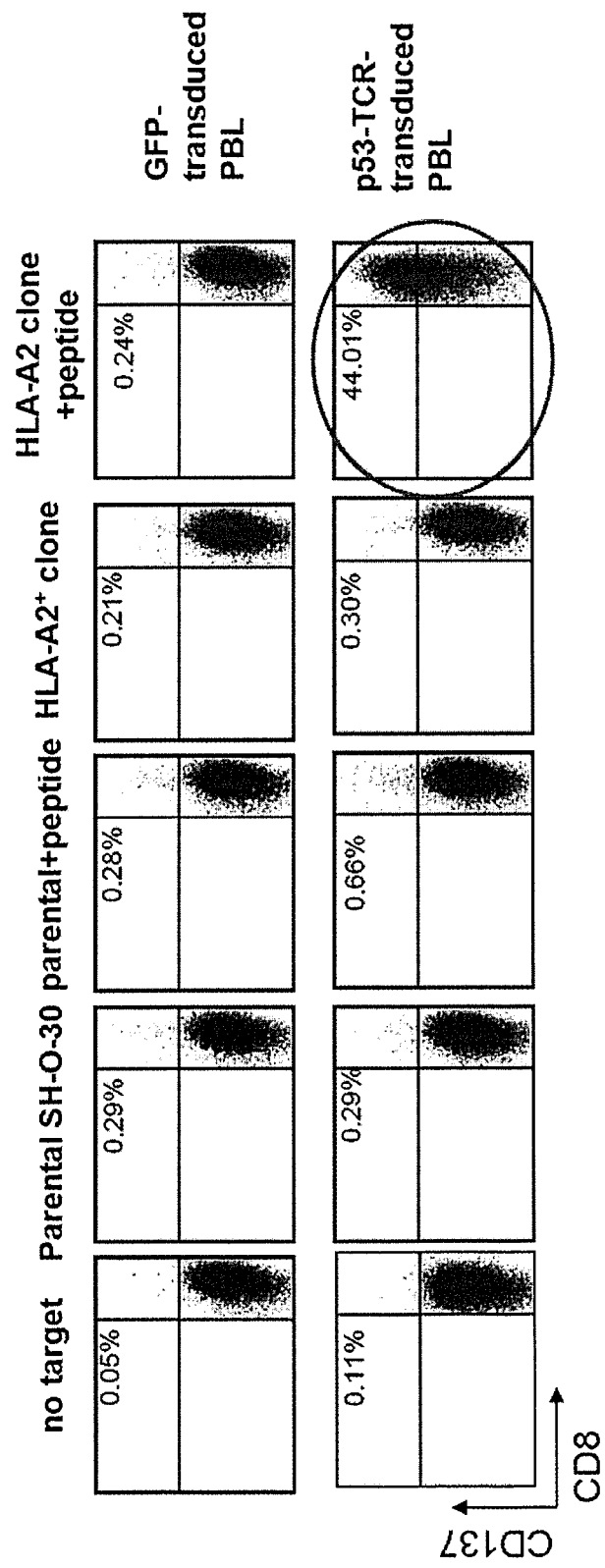
FIGS. 13A-B: Functional assessment of HLA-A2 transgene in SH-O-30.10-A2 (a) and SH-L-40-A2 clones by flow cytometry.
Figure 13B:
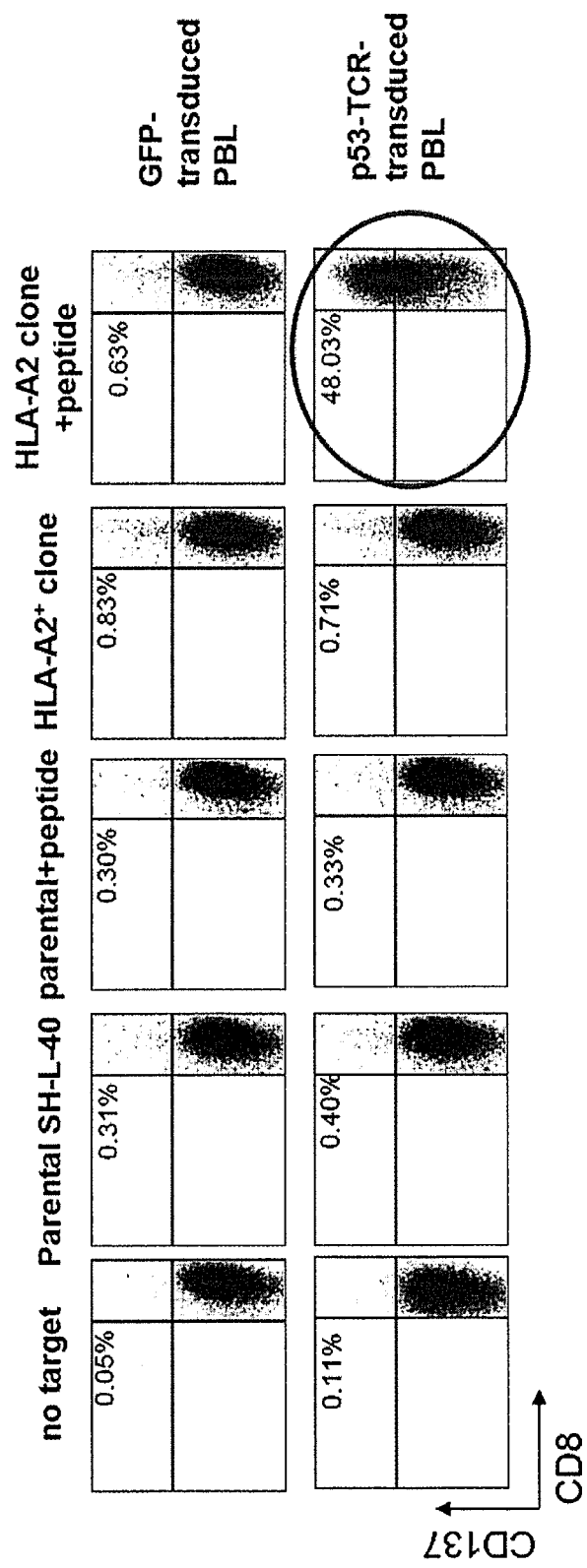
Figure 14:
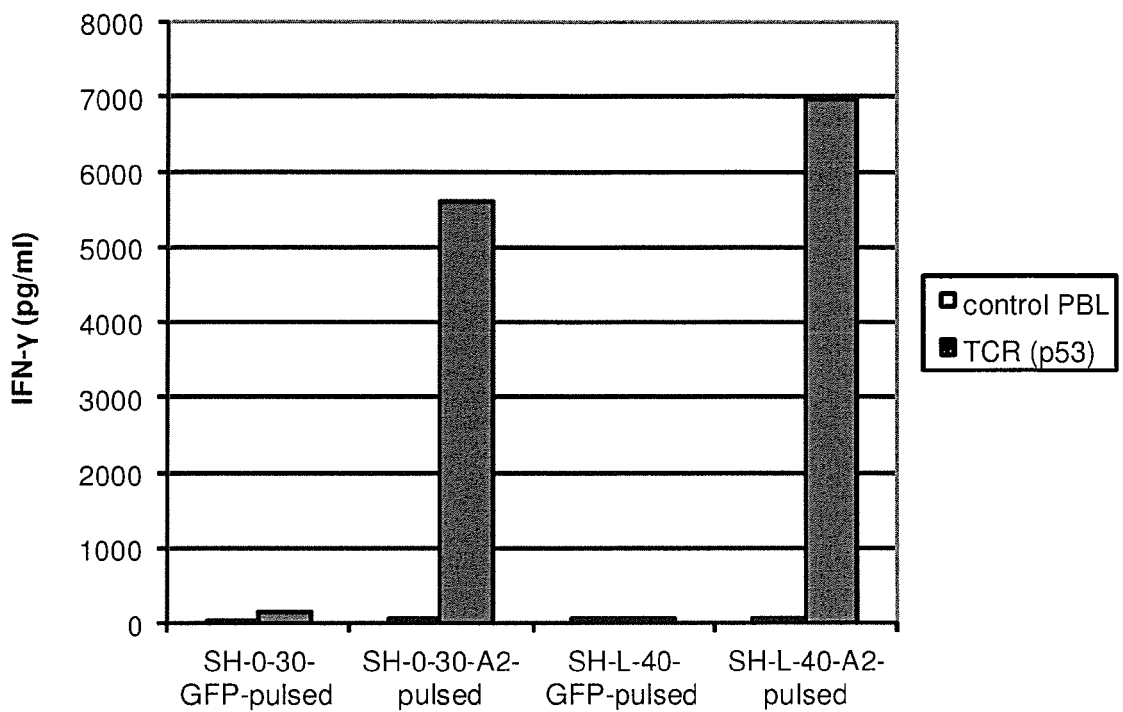
FIG. 14. Functional assessment of HLA-A2 transgene in SH-O-30.10-A2 (a) and SH-L-40-A2 clones by interferon gamma (IFNγ) ELISA.

Functional validation of HLA-A2 molecules on SH-O-30.10-A2 and SH-L-40-A2 clones was performed by co-culture of these clones with p53 αβTCR-transduced lymphocytes. FIG. 13 summarizes the results of flow cytometry experiments in which p53-specific T cells exhibited potent activation, as measured by CD137 up-regulation, against HLA-A2⁺ but not HLA-AZ clones. In line with these results, robust activation of p53 specific T cells against HLA-A2⁺ clones was confirmed by IFNγ ELISA, as shown in FIG. 14.

Full histograms—p53 specific T cells; empty histograms—control cells; SH-O-30-GFP-pulsed—GFP transduced SH-O-30.10 cells pulsed with the p53 derived peptide; SH-O-30-A2-pulsed—HLA-A2 transduced SH-O-30.10 cells pulsed with the p53 derived peptide; SH-L-40-GFP-pulsed—GFP transduced SH-L-40 pulsed with the p53 derived peptide; SH-L-40-A2-pulsed—HLA-A2 transduced SH-L-40 pulsed with the p53 derived peptide.

Example 10

Cloning and Stable Expression of 4-1BBL Transgene in SH-M-20-A2 Cells

Due to the lack of a constitutively active CD40 transgene to affect vaccine immunogenicity, it was decided to examine the vaccine cells' ability of co-stimulation of cognate T cells via 4-1BBL-4-1 BB pair. To this end, SH-M-20-A2 cells were transfected with 4-1BBL-encoding construct (pcDNA3.1-4-1BBL-Hygro$^+$, described below).

Figure 15:
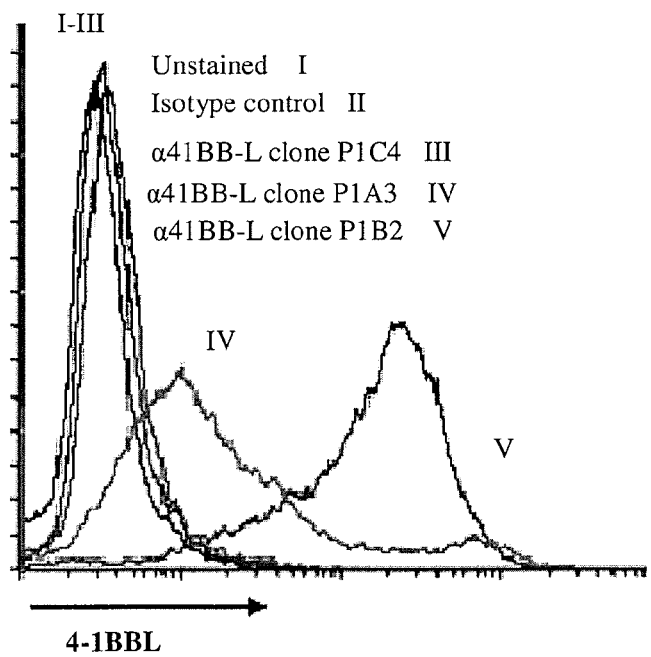
FIG. 15. Improved immunogenicity of SH-M-20-A2 cells with pcDNA3.1-4-1BBL and detection of surface 4-1BBL by flow cytometry.

The double-transfected clones (HLA-A2$^+$4-1BBL$^+$) were established, as shown in FIG. 15 (clones P1A3 and P1B2, histograms IV and V). An improvement of tumor cell ability to stimulate tumor-infiltrating lymphocytes was demonstrated in IFNγ ELISA using 4-1BBL single-transfected clones of 624 (originally HLA-A2+), as targets (Table 15).

Tumor-infiltrated lymphocytes derived from HLA-A2-positive melanoma patients M209 and M431 were co-cultured with HLA-A2+ melanoma cells 624 (624mock_N7—pcDNA3.1-mock transfected) or with 4-1BBL-expressing clones (624_41BBL_H1, 624_41BBL_H6, 624_41BBL_H12, 624_41BBL_N4, and 624_41BBL_N7-pcDNA3.1-4-1BBL-Hygro$^+$ transfected). T cell activity was measured by IFNγ ELISA 20 h after co-culture.

TABLE 15

Improved immunogenicity of tumor cells by de novo expression of 4-1BBL.

| | IFNγ secretion in presence of target cell | |
|---|---|---|
| Clone | TIL 209 (A2+) | TIL 431 (A2+) |
| 624mock_N7 | 4860 | 880 |
| 624_41BBL_H1 | 6900 | 992 |
| 624_41BBL_H6 | 6750 | 1520 |
| 624_41BBL_H12 | 9620 | 3480 |
| 624_41BBL_N4 | 9070 | 2040 |
| 624_41BBL_N7 | 8250 | 2200 |

Example 11

Sequences

The protein sequence of human MHC class I antigen, HLA-B35, (the HLA-B*3501 or B*35:01:01:01 allele) is identified as SEQ ID NO: 1, as follows:

(SEQ ID NO: 1; accession no. Uniprot P30685)
MRVTAPRTVLLLLWGAVALTETWAGSHSMRYFYTAMSRPGRGEPR
FIAVGYVDDTQFVRFDSDAASPRTEPRAPWIEQEGPEYWDRNTQIF
KTNTQTYRESLRNLRGYYNQSEAGSHIIQRMYGCDLGPDGRLLRGH
DQSAYDGKDYIALNEDLSSWTAADTAAQITQRKWEAARVAEQLRAY
LEGLCVEWLRRYLENGKETLQRADPPKTHVTHHPVSDHEATLRCW
ALGFYPAEITLTWQRDGEDQTQDTELVETRPAGDRTFQKWAAVVVP
SGEEQRYTCHVQHEGLPKPLTLRWEPSSQSTIPIVGIVAGLAVLAVV
VIGAVVATVMCRRKSSGGKGGSYSQAASSDSAQGSDVSLTA The nucleic acid sequence of the mRNA encoding human MHC class I antigen, HLA-B35 (HLA-B*3501 allele) is identified as SEQ ID NO: 2, as follows:

(SEQ ID NO: 2)
Atgcgggtcacggcgccccgaaccgtcctcctgctgctctgggggcagt
ggccctgaccgagacctgggccggctcccactccatgaggtatttctaca
ccgccatgtcccggcccggccgcggggagccccgcttcatcgcagtgggc
tacgtggacgacacccagttcgtgaggttcgacagcgacgccgcgagtcc
gaggacggagcccgggcgccatggatagagcaggaggggccggagtatt
gggaccggaacacacagatcttcaagaccaacacacagacttaccgagag
agcctgcggaacctgcgcggctactacaaccagagcgaggccgggtctca
catcatccagaggatgtatggctgcgacctggggcccgacgggcgcctcc
tccgcgggcatgaccagtccgcctacgacggcaaggattacatcgccctg
aacgaggacctgagctcctggaccgcggcggacaccgcggctcagatcac
ccagcgcaagtgggaggcggcccgtgtggcggagcagctgagagcctacc
tggaggcctgtcgtggagtggctccgcagatacctggagaacgggaag
gagacgctgcagcgcgcggaccccccaaagacacacgtgacccaccacc
cgtctctgaccatgaggccaccctgaggtgctgggcccctgggcttctacc
ctgcggagatcacactgacctggcagcgggatggcgaggaccaaactcag
gacactgagcttgtggagaccagaccagcaggagatagaaccttccagaa
gtgggcagctgtggtggtgccttctggagaagagcagagatacacatgcc
atgtacagcatgaggggctgccgaagccctcaccctgagatgggagcca
tcttcccagtccaccatcccatcgtgggcattgttgctggcctggctgt
cctagcagttgtggtcatcggagctgtggtcgctactgtgatgtgtagga
ggaagagctcaggtggaaaaggagggagctactctcaggctgcgtccagc
gacagtgcccagggctctgatgtgtctcacagcttga The nucleic acid sequence of the complete genomic sequence of human MHC class I antigen, HLA-B35 (HLA-B*3501 allele) is identified as SEQ ID NO: 3, as follows:

(SEQ ID NO: 3)
gatcaggacgaagtcccaggccccgggcggggctctcagggtctcaggct
ccgagagccttgtctgcattggggaggcgcagcgttggggattccccact
cccacgagtttcacttcttctcccaacctatgtcgggtccttcttccagg
atactcgtgacgcgtcccccatttcccactcccattgggtgtcggatatct
agagaagccaatcagtgtcgccggggtcccagttctaaagtccccacgca
cccaccccggactcagaatctcctcagacgccgagatgcgggtcacggcgc
cccgaaccgtcctcctgctgctctgggggcagtggccctgaccgagacc -continued

```
tgggccggtgagtgcgggtcgggagggaaatggcctctgtggggaggag
cgaggggaccgcaggcgggggcgcaggacctgaggagccgcgccgggagg
agggtcgggcgggtctcagcccctcctcgccccaggctcccactccatg
aggtatttctacaccgccatgtcccgcccggccgcggggagccccgctt
catcgcagtgggctacgtggacgacacccagttcgtgaggttcgacagcg
acgccgcgagtccgaggacggagccccgggcgccatggatagagcaggag
gggccggagtattgggaccggaacacacagatcttcaagaccaacacaca
gacttaccgagagagcctgcggaacctgcgcggctactacaaccagagcg
aggccggtgagtgaccccggcccggggcgcaggtcacgactcccatccc
ccacgtacggcccgggtcgccccgagtctccgggtccgagatccgcctcc
ctgaggccgcgggacccgcccagaccctcgaccggcgagagccccaggcg
cgtttacccggtttcattttcagttgaggccaaaatccccgcgggttggt
cggggcggggcggggctcggggacggggctgaccgcggggccggggcca
gggtctcacatcatccagaggatgtatggctgcgacctggggcccgacgg
gcgcctcctccgcgggcatgaccagtccgcctacgacggcaaggattaca
tcgccctgaacgaggacctgagctcctggaccgcggcggacaccgcggct
cagatcacccagcgcaagtgggaggcggcccgtgtggcggagcagctgag
agcctacctggagggcctgtgcgtggagtggctccgcagatacctggaga
acgggaaggagacgctgcagcgcgcgggtaccaggggcagtggggagcct
tccccatctcctataggtcgcggggatggcctcccacgagaagaggagg
aaaatgggatcagcgctagaatgtcgccctcccttgaatggagaatggca
tgagttttcctgagttttcctctgagggcccctcttctctctaggacaat
taaggggatgacgtctctgaggaaatggaggggaagacagtccctagaata
ctgatcaggggtcccctttgacccctgcagcagccttgggaaccgtgact
tttcctctcaggccttgttctctgcctcacactcagtgtgtttgggctc
tgattccagcacttctgagtcactttacctccactcagatcaggagcaga
agtccctgttccccgctcagagactcgaactttcaatgaataggagatt
atcccaggtgcctgcgtccaggctggtgtctgggttctgtgcccttccc
cacaccaggtgtcctgtccattctcaggctggtcacatggggtggtcctag
ggtgtcccatgagagatgcaaagcgcctgaattttctgactcttcccatc
agacccccaaagacacacgtgacccaccacccgtctctgaccatgagg
ccaccctgaggtgctgggccctggcttctaccctgcggagatcacactg
acctggcagcgggatggcgaggaccaaactcaggacactgagcttgtgga
gaccagaccagcaggagatagaaccttccagaagtgggcagctgtggtgg
tgccttctggagaagagcagagatacacatgccatgtacagcatgagggg
ctgccgaagcccctcacctgagatggggtaaggaggggatgagggtc
atatctcttctcagggaaagcaggagcccttctggagcccttcagcaggg
tcaggggcccctcgtcttccctccttcccagagccatcttcccagtccca
ccatccccatcgtgggcattgttgctggcctggctgtcctagcagttgtg
gtcatcggagctgtggtcgctactgtgatgtgtaggaggaagagctcagg
```

```
tagggaaggggtgaggggtgggtctgggttttcttgtcccactgggggt
ttcaagccccaggtagaagtgttccctgcctcattactgggaagcagcat
ccacacaggggctaacgcagcctgggaccctgtgtgccagcacttactct
tttgtgcagcacatgtgacaatgaaggacggatgtatcaccttgatggtt
gtggtgttggggtcctgatttcagcattcatgagtcaggggaaggtccct
gctaaggacagaccttaggagggcagttggtccaggacccacacttgctt
tcctcgtgtttcctgatcctgccttgggtctgtagtcatacttctggaaa
ttccttttgggtccaagacgaggaggttcctctaagatctcatggccctg
cttcctcccagtcccctcacaggacattttcttcccacaggtggaaaagg
agggagctactctcaggctgcgtgtaagtggtggggtgggagtgtggag
gagctcacccaccccataattcctcctgtcccacgtctcctgcgggctct
gaccaggtcctgttttgttctactccagccagcgacagtgcccagggct
ctgatgtgtctctcacagcttgaaaaggtgagattcttggggtctagagt
gggcggggggcggggaggggcagaggggaaaggcctgggtaatggag
attctttgattgggatgtttcgcgtgtgtcgtgggctgttcagagtgtca
tcacttaccatgactaaccagaatttgttcatgactgttgttttctgtag
cctgagacagctgtcttgtgagggactgagatgcaggatttcttcactcc
tcccctttgtgacttcaagggcctctggcatctcttctgcaaaggcacc
tgaatgtgtctgcgtccctgttagcctaatgtgaggaggtggagagacag
cccaccccgtgtccactgtgacccct.
```

For example, human MHC class I antigen (HLA-A) mRNA, HLA-A*0201 allele may have the following nucleic acid sequence:

```
        (SEQ ID NO: 5; genebank no. AY365426.1)
atggccgtca tggcgccccg aacctcgtc ctgctactct cggggctct ggccctgaccccagacctggg cgggctctca ctccatgagg tatttcttca catccgtgtc ccggcccggc cgcggggagc cccgcttcat cgcagtgggc tacgtggacg acacgcagtt cgtgcggttc gacagcgacg ccgcgagcca gaggatggag ccgcgggcgc cgtggataga gcaggagggt ccggagtatt gggacgggga cacggaaa gtgaaggccc actcacagac tcaccgagtg gacctgggga ccctgcgcgg ctactacaac cagagcgagg ccggttctca ccgtccag aggatgtatg gctgcgacgt ggggtcggac tggcgcttcc tccgcgggta ccaccagtac gcctacgacg gcaaggatta catcgccctg aaagaggacc tgcgctcttg gaccgcggcg gacatggcag ctcagaccac caagcacaag tgggaggcgg cccatgtggc ggagcagttg agagcctacc tggagggcac gtgcgtggag tggctccgca gatacctgga gaacgggaag gagacgctgc agcgcacgga cgccccaaa acgcatatga ctcaccacgc tgtctctgac catgaagcca ccctgaggtg
```

```
ctgggccctg agcttctacc ctgcggagat cacactgacc
tggcagcggg atggggagga ccagacccag gacacggagc
tcgtggagac caggcctgca ggggatggaa ccttccagaa
gtgggcggct gtggtggtgc cttctggaca ggagcagaga
tacacctgcc atgtgcagca tgagggtttg cccaagcccc
tcaccctgag atgggagccg tcttcccagc ccaccatccc
catcgtgggc atcattgctg gcctggttct ctttggagct
gtgatcactg gagctgtggt cgctgctgtg atgtggagga
ggaagagctc agatagaaaa ggagggagct actctcaggc
tgcaagcagt gacagtgccc agggctctga tgtgtctctc
acagcttgta aagtgtga,
``` and the corresponding gene product has the following amino acid sequence:

```
                                          (SEQ ID NO: 4)
MAVMAPRTLVLLLSGALALTQTWAGSHSMRYFFTSVSRPGRGEPR
FIAVGYVDDTQFVRFDSDAASQRMEPRAPWIEQEGPEYWDGETRK
VKAHSQTHRVDLGTLRGYYNQSEAGSHTVQRMYGCDVGSDWRFL
RGYHQYAYDGKDYIALKEDLRSWTAADMAAQTTKHKWEAAHVAEQ
LRAYLEGTCVEWLRRYLENGKETLQRTDAPKTHMTHHAVSDHEATL
RCWALSFYPAEITLTWQRDGEDQTQDTELVETRPAGDGTFQKWAA
VVVPSGQEQRYTCHVQHEGLPKPLTLRWEPSSQPTIPIVGIIAGLVLF
GAVITGAVVAAVMWRRKSSDRKGGSYSQAASSDSAQGSDVSLTAC
KV.
```

Human 41-BBL may have the amino acid sequence:

```
                    (SEQ ID NO: 6; accession no. P41273)
MEYASDASLDPEAPWPPAPRARACRVLPWALVAGLLLLLLLAAACA
VFLACPWAVSGARASPGSAASPRLREGPELSPDDPAGLLDLRQGM
FAQLVAQNVLLIDGPLSWYSDPGLAGVSLTGGLSYKEDTKELVVAKA
GVYYVFFQLELRRVVAGEGSGSVSLALHLQPLRSAAGAAALALTVDL
PPASSEARNSAFGFQGRLLHLSAGQRLGVHLHTEARARHAWQLTQ
GATVLGLFRVTPEIPAGLPSPRSE.
```

A nucleic acid sequence coding for 41-BBL (mRNA) may be represented by SEQ ID NO:7, as follows:

```
                    (SEQ ID NO: 7; accession no. U03398.1)
gtcatggaat acgcctctga cgcttcactg gaccccgaag
ccccgtggcc tcccgcgccc cgcgctcgcg cctgccgcgt
actgccttgg gccctggtcg cggggctgct gctgctgctg
ctgctcgctg ccgcctgcgc cgtcttcctc gcctgcccct
gggccgtgtc cggggctcgc gcctcgcccg gctccgcggc
cagcccgaga ctccgcgagg gtcccgagct tcgcccgac
gatcccgccg gcctcttgga cctgcggcag ggcatgtttg
cgcagctggt ggcccaaaat gttctgctga tcgatgggcc
cctgagctgg tacagtgacc caggcctggc aggcgtgtcc
ctgacggggg gcctgagcta caagaggac acgaaggagc
tggtggtggc caaggctgga gtctactatg tcttctttca
actagagctg cggcgcgtgg tggccggcga gggctcaggc
tccgtttcac ttgcgctgca cctgcagcca ctgcgctctg
ctgctgggc cgccgccctg gctttgaccg tggacctgcc
acccgcctcc tccgaggctc ggaactcggc cttcggtttc
cagggccgct tgctgcacct gagtgccggc cagcgcctgg
gcgtccatct tcacactgag gccagggcac gccatgcctg
gcagcttacc cagggcgcca cagtcttggg actcttccgg
gtgaccccg aaatcccagc cggactccct tcaccgaggt
cggaataacg cccagcctgg gtgcagccca cctggacaga
gtccgaatcc tactccatcc ttcatggaga cccctggtgc
tgggtccctg ctgctttctc tacctcaagg ggcttggcag
gggtccctgc tgctgacctc cccttgagga ccctcctcac
ccactccttc cccaagttgg accttgatat ttattctgag
cctgagctca gataatatat tatatatatt atatatatat
atatatttct atttaaagag gatcctgagt ttgtgaatgg
acttttttag aggagttgtt ttggggggggg ggtcttcgac
attgccgagg ctggtcttga actcctggac ttagacgatc
ctcctgcctc agcctcccaa gcaactggga ttcatccttt
ctattaattc attgtactta tttgcctatt tgtgtgtatt
gagcatctgt aatgtgccag cattgtgccc aggctagggg
gctatagaaa catctagaaa tagactgaaa gaaaatctga
gttatggtaa tacgtgagga atttaaagac tcatcccag
cctccacctc ctgtgtgata cttgggggct agcttttttc
tttctttctt tttttttgaga tggtcttgtt ctgtcaacca
ggctagaatg cagcggtgca atcatgagtc aatgcagcct
ccagcctcga cctcccgagg ctcaggtgat cctcccatct
cagcctctcg agtagctggg accacagttg tgtgccacca
cacttggcta acttttttaat tttttttgcgg agacggtatt
gctatgttgc caaggttgtt tacatgccag tacaatttat
aataaacact cattttttcc.
```

Thus, cells described herein may express SEQ ID NOs: 1 and 4, SEQ ID NOs: 1 and 6, SEQ ID NOs: 4 and 6, or SEQ ID NOs: 1, 4 and 6. Some cells express substantially identical sequences (containing conservative amino acid substitutions with >90% amino acid identity and no apparent or significant functional changes). Without limitation, these sequences may be considered equivalent to a sequence as set forth herein.

For example, the MSGV1-HLA-A0201-ires-Neo expression vector contains an HLA-A2 open reading frame (ORF)

corresponding to nucleotides 3-1100 of SEQ ID NO: 15, encoding an HLA-A2 molecule corresponding to SEQ ID NO: 4, with a conservative substitution of Phe to Tyr at position 33. This ORF is transcriptionally linked via an internal ribosome entry site (IRES) to a neomycin-encoding ORF.

The ORFs are expressed from retroviral LTR sequences, positioned at nucleotides 2572-3086 (3' LTR) and 6259-6772 (5' LTR) of SEQ ID NO: 15.

The nucleic acid sequence of the exemplary retroviral vector MSGV1-HLA-A0201-ires-Neo is set forth below:

```
                                                        (SEQ ID NO: 15)
   1 ccatggccgt catggcgccc cgaaccctcg tcctgctact ctcggggct
  51 ctggccctga cccagacctg ggcgggctct cactccatga ggtatttcta
 101 cacctccgtg tcccggcccg gccgcgggga gccccgcttc atcgcagtgg
 151 gctacgtgga caacacgcag ttcgtgcggt tcgacagcga cgccgcgagc
 201 cagaggatgg agccgcgggc gccgtggata gagcaggagg gtccggagta
 251 ttgggacggg gagacacgga aagtgaaggc ccactcacag actcaccgag
 301 tggacctggg gaccctgcgc ggctactaca accagagcga ggccggttct
 351 cacaccgtcc agaggatgta tggctgcgac gtggggtcgg actggcgctt
 401 cctccgcggg taccaccagt acgcctacga cggcaaggat tacatcgccc
 451 tgaaagagga cctgcgctct tggaccgcgg cggacatggc agctcagacc
 501 accaagcaca gtgggaggc ggcccatgtg gcggagcagt tgagagccta
 551 cctggagggc acgtgcgtgg agtggctccg cagatacctg gagaacggga
 601 aggagacgct gcagcgcacg gacgccccca aaacgcatat gactcaccac
 651 gctgtctctg accatgaagc caccctgagg tgctgggccc tgagcttcta
 701 ccctgcggag atcacactga cctggcagcg ggatggggag accagaccc
 751 aggacacgga gctcgtggag accaggcctg caggggatgg aaccttccag
 801 aagtgggcgg ctgtggtggt gccttctgga caggagcaga gatacacctg
 851 ccatgtgcag catgagggtt tgcccaagcc cctcaccctg agatgggagc
 901 cgtcttccca gcccaccatc cccatcgtgg gcatcattgc tggcctggtt
 951 ctctttggag ctgtgatcac tggagctgtg gtcgctgctg tgatgtggag
1001 gaggaagagc tcagatagaa aaggaggga ctactctcag gctgcaagca
1051 gtgacagtgc ccagggctct gatgtgtctc tcacagcttg taaagtgtga
1101 gcggccgctc gactgcagga attaattccg cccctctccc tccccccccc
1151 ctaacgttac tggccgaagc cgcttggaat aaggccggtg tgtgtttgtc
1201 tatatgtgat tttccaccat attgccgtct tttggcaatg tgagggcccg
1251 gaaacctggc cctgtcttct tgacgagcat tcctaggggt ctttccctc
1301 tcgccaaagg aatgcaaggt ctgttgaatg tcgtgaagga agcagttcct
1351 ctggaagctt cttgaagaca aacaacgtct gtagcgaccc tttgcaggca
1401 gcggaacccc ccacctggcg acaggtgcct ctgcggccaa aagccacgtg
1451 tataagatac acctgcaaag gcggcacaac cccagtgcca cgttgtgagt
1501 tggatagttg tggaaagagt caaatggctc tcctcaagcg tagtcaacaa
1551 ggggctgaag gatgcccaga aggtacccca ttgtatggga atctgatctg
1601 gggcctcggt gcacatgctt tacatgtgtt tagtcgaggt taaaaaagct
1651 ctaggccccc cgaaccacgg ggacgtggtt ttcctttgaa aaacacgatg
1701 ataagcttgc cacaaccatg ggatcggcca ttgaacaaga tggattgcac
1751 gcaggttctc cggccgcttg ggtggagagg ctattcggct atgactgggc
1801 acaacagaca atcggctgct ctgatgccgc cgtgttccgg ctgtcagcgc
```

-continued

```
1851 aggggcgccc ggttctttt gtcaagaccg acctgtccgg tgccctgaat
1901 gaactgcagg acgaggcagc gcggctatcg tggctggcca cgacgggcgt
1951 tccttgcgca gctgtgctcg acgttgtcac tgaagcggga agggactggc
2001 tgctattggg cgaagtgccg gggcaggatc tcctgtcatc tcaccttgct
2051 cctgccgaga aagtatccat catggctgat gcaatgcggc ggctgcatac
2101 gcttgatccg gctacctgcc cattcgacca ccaagcgaaa catcgcatcg
2151 agcgagcacg tactcggatg gaagccggtc ttgtcgatca ggatgatctg
2201 gacgaagagc atcaggggct cgcgccagcc gaactgttcg ccaggctcaa
2251 ggcgcgcatg cccgacggcg aggatctcgt cgtgacccat ggcgatgcct
2301 gcttgccgaa tatcatggtg gaaaatggcc gcttttctgg attcatcgac
2351 tgtggccggc tgggtgtggc ggaccgctat caggacatag cgttggctac
2401 ccgtgatatt gctgaagagc ttggcggcga atgggctgac cgcttcctcg
2451 tgctttacgg tatcgccgct cccgattcgc agcgcatcgc cttctatcgc
2501 cttcttgacg agttcttctg agggatccga taaaataaaa gattttattt
2551 agtctccaga aaaggggggg aatgaaagac cccacctgta ggtttggcaa
2601 gctagcttaa gtaacgccat tttgcaaggc atggaaaata cataactgag
2651 aatagagaag ttcagatcaa ggttaggaac agagagacag cagaatatgg
2701 gccaaacagg atatctgtgg taagcagttc ctgccccggc tcagggccaa
2751 gaacagatgg tccccagatg cggtcccgcc ctcagcagtt tctagagaac
2801 catcagatgt tccaggggtg ccccaaggac ctgaaaatga ccctgtgcct
2851 tatttgaact aaccaatcag ttcgcttctc gcttctgttc gcgcgcttct
2901 gctccccgag ctcaataaaa gagcccacaa cccctcactc ggcgcgccag
2951 tcctccgata gactgcgtcg cccgggtacc cgtgtatcca ataaaccctc
3001 ttgcagttgc atccgacttg tggtctcgct gttccttggg agggtctcct
3051 ctgagtgatt gactacccgt cagcggggt cttcatggg taacagttc
3101 ttgaagttgg agaacaacat tctgagggta ggagtcgaat attaagtaat
3151 cctgactcaa ttagccactg ttttgaatcc acatactcca atactcctga
3201 aatccatcga tggagttcat tatggacagc gcagaaagag ctggggagaa
3251 ttgtgaaatt gttatccgct cacaattcca cacaacatac gagccggaag
3301 cataaagtgt aaagcctggg gtgcctaatg agtgagctaa ctcacattaa
3351 ttgcgttgcg ctcactgccc gctttccagt cgggaaacct gtcgtgccag
3401 ctgcattaat gaatcggcca acgcgcgggg agaggcggtt tgcgtattgg
3451 gcgctcttcc gcttcctcgc tcactgactc gctgcgctcg gtcgttcggc
3501 tgcggcgagc ggtatcagct cactcaaagg cggtaatacg gttatccaca
3551 gaatcagggg ataacgcagg aaagaacatg tgagcaaaag gccagcaaaa
3601 ggccaggaac cgtaaaaagg ccgcgttgct ggcgtttttc cataggctcc
3651 gcccccctga cgagcatcac aaaaatcgac gctcaagtca gaggtggcga
3701 aacccgacag gactataaag ataccaggcg tttccccctg gaagctccct
3751 cgtgcgctct cctgttccga ccctgccgct taccggatac ctgtccgcct
3801 ttctcccttc gggaagcgtg cgctttctc atagctcacg ctgtaggtat
```

-continued

```
3851  ctcagttcgg tgtaggtcgt tcgctccaag ctgggctgtg tgcacgaacc
3901  ccccgttcag cccgaccgct gcgccttatc cggtaactat cgtcttgagt
3951  ccaacccggt aagacacgac ttatcgccac tggcagcagc cactggtaac
4001  aggattagca gagcgaggta tgtaggcggt gctacagagt tcttgaagtg
4051  gtggcctaac tacggctaca ctagaaggac agtatttggt atctgcgctc
4101  tgctgaagcc agttaccttc ggaaaaagag ttggtagctc ttgatccggc
4151  aaacaaacca ccgctggtag cggtggtttt tttgtttgca agcagcagat
4201  tacgcgcaga aaaaaaggat ctcaagaaga tcctttgatc ttttctacgg
4251  ggtctgacgc tcagtggaac gaaaactcac gttaagggat tttggtcatg
4301  agattatcaa aaaggatctt cacctagatc cttttaaatt aaaaatgaag
4351  ttttaaatca atctaaagta tatatgagta aacttggtct gacagttacc
4401  aatgcttaat cagtgaggca cctatctcag cgatctgtct atttcgttca
4451  tccatagttg cctgactccc cgtcgtgtag ataactacga tacgggaggg
4501  cttaccatct ggccccagtg ctgcaatgat accgcgagac ccacgctcac
4551  cggctccaga tttatcagca ataaaccagc cagccggaag ggccgagcgc
4601  agaagtggtc ctgcaacttt atccgcctcc atccagtcta ttaattgttg
4651  ccgggaagct agagtaagta gttcgccagt taatagtttg cgcaacgttg
4701  ttgccattgc tacaggcatc gtggtgtcac gctcgtcgtt tggtatggct
4751  tcattcagct ccggttccca acgatcaagg cgagttacat gatccccat
4801  gttgtgcaaa aaagcggtta gctccttcgg tcctccgatc gttgtcagaa
4851  gtaagttggc cgcagtgtta tcactcatgg ttatggcagc actgcataat
4901  tctcttactg tcatgccatc cgtaagatgc ttttctgtga ctggtgagta
4951  ctcaaccaag tcattctgag aatagtgtat gcggcgaccg agttgctctt
5001  gcccggcgtc aatacgggat aataccgcgc cacatagcag aactttaaaa
5051  gtgctcatca ttggaaaacg ttcttcgggg cgaaaactct caaggatctt
5101  accgctgttg agatccagtt cgatgtaacc cactcgtgca cccaactgat
5151  cttcagcatc ttttactttc accagcgttt ctgggtgagc aaaaacagga
5201  aggcaaaatg ccgcaaaaaa gggaataagg cgacacgga atgttgaat
5251  actcatactc ttcctttttc aatattattg aagcatttat cagggttatt
5301  gtctcatgag cggatacata tttgaatgta tttagaaaaa taaacaaata
5351  ggggttccgc gcacatttcc ccgaaaagtg ccacctgacg tctaagaaac
5401  cattattatc atgacattaa cctataaaaa taggcgtatc acgaggccct
5451  ttcgtctcgc gcgtttcggt gatgacggtg aaaacctctg acacatgcag
5501  ctcccggaga cggtcacagc ttgtctgtaa gcggatgccg ggagcagaca
5551  agcccgtcag ggcgcgtcag cgggtgttgg cgggtgtcgg ggctggctta
5601  actatgcggc atcagagcag attgtactga gagtgcacca tatgcggtgt
5651  gaaataccgc acagatgcgt aaggagaaaa taccgcatca ggcgccattc
5701  gccattcagg ctgcgcaact gttgggaagg gcgatcggtg cgggcctctt
5751  cgctattacg ccagctggcg aaagggggat gtgctgcaag gcgattaagt
5801  tgggtaacgc cagggttttc ccagtcacga cgttgtaaaa cgacggccag
```

-continued

```
5851 tgccacgctc tcccttatgc gactcctgca ttaggaagca gcccagtagt
5901 aggttgaggc cgttgagcac cgccgccgca aggaatggtg catgcaagga
5951 gatggcgccc aacagtcccc cggccacggg gcctgccacc atacccacgc
6001 cgaaacaagc gctcatgagc ccgaagtggc gagcccgatc ttccccatcg
6051 gtgatgtcgg cgatataggc gccagcaacc gcacctgtgg cgccggtgat
6101 gccggccacg atgcgtccgg cgtagaggcg atttaaagac aggatatcag
6151 tggtccaggc tctagttttg actcaacaat atcaccagct gaagcctata
6201 gagtacgagc catagataaa ataaaagatt ttatttagtc tccagaaaaa
6251 gggggaatg aaagacccca cctgtaggtt tggcaagcta gcttaagtaa
6301 cgccattttg caaggcatgg aaaatacata actgagaata gagaagttca
6351 gatcaaggtt aggaacagag agacagcaga atatgggcca acaggatat
6401 ctgtggtaag cagttcctgc cccggctcag ggccaagaac agatggtccc
6451 cagatgcggt cccgccctca gcagtttcta gagaaccatc agatgtttcc
6501 agggtgcccc aaggacctga aaatgaccct gtgccttatt tgaactaacc
6551 aatcagttcg cttctcgctt ctgttcgcgc gcttctgctc cccgagctca
6601 ataaaagagc ccacaacccc tcactcggcg cgccagtcct ccgatagact
6651 gcgtcgcccg ggtacccgta ttcccaataa agcctcttgc tgtttgcatc
6701 cgaatcgtgg actcgctgat ccttgggagg gtctcctcag attgattgac
6751 tgcccacctc gggggtcttt catttggagg ttccaccgag atttggagac
6801 ccctgcctag ggaccaccga ccccccgcc gggaggtaag ctggccagcg
6851 gtcgtttcgt gtctgtctct gtctttgtgc gtgtttgtgc cggcatctaa
6901 tgtttgcgcc tgcgtctgta ctagttagct aactagctct gtatctggcg
6951 gacccgtggt ggaactgacg agttcggaac acccggccgc aaccctggga
7001 gacgtcccag ggacttcggg ggccgttttt gtggcccgac ctgagtccaa
7051 aaatcccgat cgttttggac tctttggtgc accccccta gaggagggat
7101 atgtggttct ggtaggagac gagaacctaa aacagttccc gcctccgtct
7151 gaattttgc tttcggtttg ggaccgaagc cgcgccgcgc gtcttgtctg
7201 ctgcagcatc gttctgtgtt gtctctgtct gactgtgttt ctgtatttgt
7251 ctgagaatat gggcccgggc tagcctgtta ccactcccctt aagtttgacc
7301 ttaggtcact ggaaagatgt cgagcggatc gctcacaacc agtcggtaga
7351 tgtcaagaag agacgttggg ttaccttctg ctctgcagaa tggccaacct
7401 ttaacgtcgg atggccgcga cacggcacct ttaaccgaga cctcatcacc
7451 caggttaaga tcaaggtctt ttcacctggc ccgcatggac acccagacca
7501 ggtcccctac atcgtgacct gggaagcctt ggcttttgac ccccctccct
7551 gggtcaagcc ctttgtacac cctaagcctc cgcctcctct tcctccatcc
7601 gccccgtctc tcccccttga acctcctcgt tcgacccgc ctcgatcctc
7651 cctttatcca gccctcactc cttctctagg cgccnnnnca tatgagatct
7701 tatatggggc accccgccc cttgtaaact tccctgaccc tgacatgaca
7751 agagttacta acagcccctc tctccaagct cacttacagg ctctctactt
7801 agtccagcac gaagtctgga gacctctggc ggcagcctac caagaacaac
```

-continued

```
7851 tggaccgacc ggtggtacct caccct tacc gagtcggcga cacagtgtgg 7901 gtccgccgac accagactaa gaacctagaa cctcgctgga aaggacctta 7951 cacagtcctg ctgaccaccc ccaccgccct caaagtagac ggcatcgcag 8001 cttggataca cgccgcccac gtgaaggctg ccgacccgg gggtggacca 8051 tcctctagac cg.
```

Thus, cells described herein (which may be used in the compositions and methods of the invention) may express gene products having sequences substantially identical to SEQ ID NOs:1 and 4, SEQ ID NOs:1 and 6, SEQ ID NOs:4 and 6, or SEQ ID NOs:1, 4 and 6, as defined herein.

In addition, it is to be understood, that due to the degeneracy of the genetic code, additional equivalent nucleic acid sequences may be used to express the corresponding polypeptide products.

For example, a nucleic acid sequence encoding a 41-BBL protein of SEQ ID NO: 6 may also be represented by SEQ ID NO: 14, as follows:

```
                                           (SEQ ID NO: 14)
atggaatatgcatccgatgcctcccttgaccctgaagcaccttggcctcc cgccccagagcacgagcttgtagagttctcccttgggcccttgtcgctg gacttctccttctcctccttctcgccgccgctgtgcagtgttccttgca tgtccttgggccgttctggtgccagagcctcacctggaagtgcagcatc tccccgacttcgcgaaggtccagaactttccccgatgatcctgccggac tccttgacttgcgccaaggcatgtttgctcagctcgtagcacagaatgtc ctcctcattgacggtcccctttcatggtattctgatccaggcctcgctgg cgtttccttactggcggtctgtcctataaagaagataccaaagaacttg tcgttgctaaggccggtgtttactacgttttttttcagctcgaactccgc agagtcgtcgccggcgaaggatccggttctgttagtctcgcacttcatct ccagcccctcagatcagccgcaggagctgccgccctcgccctcactgttg acctcccacctgcctcctcagaagctagaaattccgcgtttggttttcag ggaagactccttcatctgtccgctggccaacgattgggtgtccatctcca taccgaagctcgcgcgcgacacgcatggcaactcacacagggcgctactg tacttggcctctttagagtaacacccgaaattcctgccggtttgccctcc ccccgatccgaataa.
```

For the generation of an exemplary pcDNA3.1-4-1BBL-Hygro+ plasmid, the 4-1BBL full-length cDNA containing the 4-1BBL optimized reading frame with HindIII and NotI restriction sites in 3' and 5'-ends (SEQ ID NO: 14) was cloned into HindIII and NotI unique restriction sites of pcDNA3.1+ Hygro (Invitrogen). Following transfection, expression of surface 4-1BBL was confirmed by FACS staining with 4-1BBL-specific mAb (clone 5F4).

REFERENCES

Barth et al. Cancer Res. 1994 Jul. 1; 54(13):3342-5.
Bioley, G., P. Guillaume, I. Luescher, A. Yeh, B. Dupont, N. Bhardwaj, G. Mears, L. J. Old, D. Valmori, and M. Ayyoub. 2009. HLA class I-associated immunodominance affects CTL responsiveness to an ESO recombinant protein tumor antigen vaccine. Clin Cancer Res 15:299-306.
Bystryn, J. C., R. Oratz, D. Roses, M. Harris, M. Henn, and R. Lew. 1992. Relationship between immune response to melanoma vaccine immunization and clinical outcome in stage II malignant melanoma. Cancer 69:1157-1164.
Chapman, P. B. Seminars in oncology 34:516-523 (2007).
Eggermont, A. M. et al., Lancet. 372:117-126 (2008).
Hoon D. S. B. et al., Journal of Clinical Oncology 16: 1430-1437 (1998).
Kirkwood, J. et al., J. Clin. Oncol. 19:2370-2380 (2001)
Kvistborg, P., S. R. Hadrup, I. M. Svane, M. H. Andersen, and P. T. Straten. 2008. Characterization of a single peptide derived from cytochrome P450 1B1 that elicits spontaneous human leukocyte antigen (HLA)-A1 as well as HLA-B35 restricted CD8 T-cell responses in cancer patients. Hum Immunol 69:266-272.
Lotem, M. et al., Clin. Cancer Res. 15:4968-4977, 2009.
Lotem, M., T. et al., Br. J. Cancer. 86:1534-1539 (2002).
Mitchell, M. S. et al., J. Clin. Oncol. 25:2078-2085, 2007.
Morel, S., A. Ooms, A. Van Pel, T. Wolfel, V. G. Brichard, P. van der Bruggen, B. J. Van den Eynde, and G. Degiovanni. 1999. A tyrosinase peptide presented by HLA-B35 is recognized on a human melanoma by autologous cytotoxic T lymphocytes. Int J Cancer 83:755-759.
Morelli, A. E. Am. J. Transplant 6:254-261 (2006).
Morton et al. Ann Surg. 1992 October; 216(4):463-82. Erratum in: Ann Surg 1993 March; 217(3):309.
Morton et al. Ann Surg. 2002 October; 236(4):438-48; discussion 448-9.
Pectasides, D. et al., J. Clin. Oncol. 27:939-944 (2009)
Reker, S., J. C. Becker, I. M. Svane, E. Ralfkiaer, P. T. Straten, and M. H. Andersen. 2004. HLA-B35-restricted immune responses against survivin in cancer patients. Int J Cancer 108:937-941.
Riker et al., Expert Opin. Biol. Ther. (2007) 7(3).
Schultz, E. S., Y. Zhang, R. Knowles, J. Tine, C. Traversari, T. Boon, and P. van der Bruggen. 2001. A MAGE-3 peptide recognized on HLA-B35 and HLA-A1 by cytolytic T lymphocytes. Tissue Antigens 57:103-109.
Sharpe et al., Immunol Rev. 2009 May; 229(1): 5-11.
Vigneron, N., A. Ooms, S. Morel, W. Ma, G. Degiovanni, and B. J. Van den Eynde. 2005. A peptide derived from melanocytic protein gp100 and presented by HLA-B35 is recognized by autologous cytolytic T lymphocytes on melanoma cells. Tissue Antigens 65:156-162.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A tumor cell line selected from the group consisting of human cell lines designated SH-M-20, SH-M-20-A2, SH-M-21, SH-O-30 and SH-L-40 that are deposited in the European Collection of Cell Cultures (ECACC) Health Protection Agency under the accession numbers 11052602, 11052604, 11052601, 11052603 and 11052605, respectively.

2. A cell line obtained from a tumor cell line selected from the group consisting of SH-M-20, SH-M-20-A2, SH-M-21, SH-O-30 and SH-L-40 engineered to stably express an additional exogenous Human Leukocyte Antigen (HLA) and/or co-stimulatory molecule for T cells.

3. The cell line of claim 2, stably expressing at least one of HLA-A2, 4-1BB ligand (4-1BBL) and HLA-B35.

4. A melanoma cell line according to claim 1, said cell line designated SH-M-20 and deposited under the accession number 11052602.

5. The melanoma cell line of claim 1, said cell line designated SH-M-20-A2 and deposited under the accession number 11052604.

6. An immunogenic composition comprising as an active ingredient at least one tumor cell line as defined in claim 1.

7. A method of enhancing an immune response to a tumor in a subject in need thereof, said method comprising administering to the subject an immunogenic composition according to claim 6, thereby enhancing the immune response in said subject.

8. A therapeutic composition for treating, ameliorating or reducing cancer in a mammalian subject, said therapeutic composition made by a method comprising the steps of selecting a subject, and providing a composition comprising one or more cell lines allogeneic to the subject, wherein at least one of said cell lines expresses at least one HLA allele identical to the HLA alleles of said subject, and wherein at least one of said cell lines endogenously or exogenously express the HLA-B35 and HLA-A2 alleles and 4-1BBL, said composition further comprising one or more pharmaceutically acceptable carrier, diluent, excipient, hapten, adjuvant or additive.

9. The composition of claim 8 comprising at least two cell lines allogeneic to said subject, or wherein said at least one of said cell lines expresses at least one HLA antigen and/or tumor associated antigens selected from the group consisting of A24, A33, B35, B49, CW04/12, A2/24, A03/25, B08/18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec, CEA-sec, CA15-3-sec and MUC-1.

10. The composition of claim 8, wherein at least one of said cell lines is a tumor cell line as defined in claim 1.

11. A therapeutic composition for treating, ameliorating, or reducing cancer in a mammalian subject, said therapeutic composition made by a method comprising the steps of selecting a subject and providing a composition comprising at least two cell lines allogeneic to the subject, wherein at least one of said cell lines expresses at least one HLA allele identical to the HLA alleles of said subject, and wherein at least one of said cell lines endogenously or exogenously express the HLA-B35 allele, said composition further comprising a pharmaceutically acceptable carrier, diluent, excipient, hapten, adjuvant or additive, wherein:
at least one of said cell lines expresses the HLA antigens A24, A33, B35, B49 and CW04/12, and the tumor associated antigens GD3, S-100, gp 100, Melan A/MART-I, HMW, MSCA, CD146, MAGE-A1 and MAGE-A3, or
at least one of said cell lines expresses the HLA antigens A2/24, and B35, and the tumor associated antigens S-100, GD3, MAGE-A1, MAGE-A3 and NY-ESO, or
at least one of said cell lines expresses the HLA antigens A26, A28, B14, B35, DRB01 and DRB104, and the tumor associated antigens, PAN cytokeratin, CEA, MAGE, and MUC-1, or
at least one of said cell lines expresses the HLA antigens A03/25, B08/18, and DRB1, and the tumor associated antigens CEA, Ca-125-sec and CEA-sec.

12. The therapeutic composition of claim 11, wherein at least one of said cell lines expresses the HLA antigens A24, A33, B35, B49 and CW04/12, and the tumor associated antigens GD3, S-100, gp 100, Melan A/MART-I, HMW, MSCA, CD146, MAGE-A1 and MAGE-A3.

13. The therapeutic composition of claim 12, wherein said cell line is a melanoma cell line designated SH-M-20 and deposited under the accession number 11052602.

14. The therapeutic composition of claim 12, wherein said cell line is a melanoma cell line designated SH-M-20-A2 and deposited under the accession number 11052604.

15. The therapeutic composition of claim 11, wherein at least one of said cell lines expresses the HLA antigens A2/24 and B35, and the tumor associated antigens S-100, GD3, MAGE-A1, MAGE-A3 and NY-ESO, or
wherein at least one of said cell lines expresses the HLA antigens A26, A28, B14, B35, DRB01 and DRB104 and the tumor associated antigens, PAN cytokeratin, CEA, MAGE, and MUC-1, or
wherein at least one of said cell lines expresses the HLA antigens A03/25, B08/18 and DRB1, and the tumor associated antigens CEA, Ca-125-sec and CEA-sec.

16. The therapeutic composition of claim 15, wherein at least one of said cell lines is a melanoma cell line designated SH-M-21 and deposited under the accession number 11052601, a lung metastasis carcinoma cell line designated SH-L-40 and deposited under the accession number 11052605, or an ovary carcinoma cell line designated SH-O-30 and deposited under the accession number 11052603.

17. A method of treating cancer in a subject in need thereof, comprising:
identifying the subject that will respond therapeutically to the method of treating cancer by determining the expression of the B35 HLA allele in a sample obtained from said subject, wherein expression of the B35 HLA allele indicates that said subject will respond therapeutically to the method of treating cancer, and
administering to said subject an immunogenic composition comprising one or more tumor cell lines allogeneic to said subject.

18. The method of claim 17, wherein the immunogenic composition comprises one or more tumor cell lines selected from the group consisting of human cell lines designated SH-M-20, SH-M-20-A2, SH-M-21, SH-O-30 and SH-L-40 that are deposited in the ECACC under the accession numbers 11052602, 11052604, 11052601, 11052603 and 11052605, respectively.

19. A method for treating, ameliorating, or reducing cancer in a mammalian subject, the method comprising administering to said subject a therapeutically effective amount of a therapeutic composition comprising at least two allogeneic cell lines, wherein:
at least one of said cell lines expresses at least one HLA allele identical to the HLA alleles of said subject,
at least one of said cell lines endogenously or exogenously expresses the HLA-B35 allele,
and wherein said at least one of said cell lines express at least one HLA antigens and/or tumor associated antigens selected from the group consisting of A24, A33, B49, CW04, CW12, A2, A24, A03, A25, B08, B18, DRB1, A26, A28, B35, DRB01, DRB104, GD3, S-100, HMB45, Melan A/MART-I, HMW, MSCA, CD146, MAGE-A1, MAGE-A3, NY-ESO-1, CEA, PAN cytokeratin, Ca-125-sec, CEA-sec, CA15-3-sec and MUC-1,
said composition further comprising a pharmaceutically acceptable carrier, diluent, excipient, hapten, adjuvant or additive.

20. The method of claim 19, wherein said cancer is selected from the group consisting of melanoma, carcinoma, leukemia, sarcoma, myeloma and lymphoma.

21. The method of claim 20, wherein said subject expresses the B35 HLA allele.

22. The method of claim 19, wherein at least one of said cell lines expresses the HLA antigens A24, A33, B35, B49 and CW04/12, and the tumor associated antigens GD3, S-100, HMB45, Melan A/MART-I, HMW, MSCA, CD146, MAGE-A1 and MAGE-A3, or wherein at least one of said cell lines expresses the HLA antigens A24, A33, B35, B49, CW04/12 and HLA-A2, and the tumor associated antigens GD3, S-100, HMB45, Melan A/MART-I, HMW, MSCA, CD146, MAGE-A1 and MAGE-A3, or wherein at least one of said cell lines expresses the HLA antigens A2/24 and B35, and the tumor associated antigens S-100, GD3, MAGE-A1, MAGE-A3 and NY-ESO, or wherein at least one of said cell lines expresses the HLA antigens A26, A28, B14, B35, DRB01 and DRB104, and the tumor associated antigens PAN cytokeratin, CEA, MAGE, and MUC-1, or wherein at least one of said cell lines expresses the HLA antigens A03/25, B08/18, and DRB1, and the tumor associated antigens CEA, Ca-125-sec and CEA-sec.

23. The method of claim 22, wherein at least one of said cell lines is a melanoma cell line designated SH-M-20 deposited under the accession number 11052602, a melanoma cell line designated SH-M-20-A2 deposited under the accession number 11052604, a melanoma cell line designated SH-M-21 deposited under the accession number 11052601, a carcinoma cell line designated SH-L-40 deposited under the accession number 11052605, or an ovary carcinoma cell line designated SH-O-30 deposited under the accession number 11052603.

24. The method of claim 19 further comprising the step of assessing the presence of the B35 HLA phenotype in the subject, and if said subject displays the B35 HLA phenotype, administering said composition to said subject.

* * * * *